US007238675B2

(12) United States Patent
Iversen

(10) Patent No.: US 7,238,675 B2
(45) Date of Patent: Jul. 3, 2007

(54) ANTISENSE ANTIBACTERIAL METHOD AND COMPOSITION

(75) Inventor: Patrick L. Iversen, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 460 days.

(21) Appl. No.: 10/719,633

(22) Filed: Nov. 21, 2003

(65) Prior Publication Data

US 2004/0137485 A1 Jul. 15, 2004

Related U.S. Application Data

(63) Continuation of application No. 09/726,774, filed on Nov. 29, 2000, now Pat. No. 6,677,153.

(60) Provisional application No. 60/168,150, filed on Nov. 29, 1999.

(51) Int. Cl.
*A61K 31/70* (2006.01)
*C07H 21/04* (2006.01)
*C07H 21/02* (2006.01)
*C12Q 1/68* (2006.01)

(52) U.S. Cl. .................... 514/44; 536/23.1; 536/24.1; 536/24.5; 435/375; 435/377

(58) Field of Classification Search .................... None
See application file for complete search history.

(56) References Cited

U.S. PATENT DOCUMENTS

| 5,220,014 | A | 6/1993 | Ackerman et al. |
| 5,821,052 | A | 10/1998 | Chen et al. |
| 5,977,340 | A | 11/1999 | Colote et al. |
| 6,060,456 | A | 5/2000 | Arnold et al. |
| 6,133,246 | A | 10/2000 | McKay et al. |
| 6,228,579 | B1 | 5/2001 | Zyskind et al. |
| 6,239,265 | B1 | 5/2001 | Cook |
| 6,495,663 | B1 | 12/2002 | Rothbard |
| 6,677,153 | B2 | 1/2004 | Iversen |
| 7,049,431 | B2 | 5/2006 | Iversen |

FOREIGN PATENT DOCUMENTS

| EP | 0 894 857 A2 | 7/1998 |
| EP | 0 892 064 A2 | 9/1998 |
| WO | WO 91 09033 | 6/1991 |
| WO | WO 98/03533 | 1/1998 |
| WO | WO 98/32467 | 7/1998 |
| WO | WO 99/02673 | 1/1999 |

OTHER PUBLICATIONS

Agrawal et al., *Tibtech*, 14:376-387 (1996).
Baker, Pamela J. et al., "Subinhibitory Concentrations of Cefpodoxime Alter Membrane Protein Expression of *Actinobacillus actinomycetemcomitans* and Enhance Its Susceptibility to Killing by Neutrophils", Antimicrobial Agents and Chemotherapy, pp. 406-412, Feb. 1995.
Branch et al., *Trends in Biochem. Sci.*, 23:45-50 (1998).
Filadoro, F., "Bacteria, Antibiotics and the Immune System: A Look at a Classic Triad", Igiene Moderna 104(3), pp. 459-465, 1995 (Abstract Only).
Green et al., *J. Am. Coll. Surg., Collective Review*, pp. 93-105.
Good et al., *Nature Biotechnology*, 16:355-358 (1998).
Good et al., *PNAS*, 95:2073-2076 (1998).
Gotfried et al., *Clinical Therapeutics*, 22(1):2-14 (2000).
Iversen, Patrick L., "Phosphorodiamidate Morpholino Oligomers", Antisense Drug Technology, Principles, Strategies and Applications, Copyright 2001 by Marcel Dekker, Inc., pp. 375-389.
Jayaraman et al., *PNAS*, 78(3):1537-1541 (1981).
Jen et al., *Stem Cells*, 18:307-319 (2000).
Rahman et al., *Antisense Research and Development*, 1:319-327 (1991).
Suzuki, I. et al., "In vivo Activity of Cefbuperazone (T-1982) Against Various Experimental Infections in Mice", Journal of Antibiotics (J. Antibiot.) (Japan) 38/2, pp. 249-258, 1985 (Abstract Only).
Summerton et al., *Biochim et. Biophys. ACTA*, 1489:141-158 (1999).
Tornqvist, Inga Odenholt et al., "Pharmacodynamic Effects of Subinhibitory Antibiotic Concentrations", Scand J. Infect Dis, Suppl. 74:94-101, 1991.
Zak, O. et al., "Correlation of Antibacterial Activities of Antibiotics in vitro and in Animal Models of Infection", Journal of Antimicrobial Chemotherapy 15, Suppl. A, pp. 273-282, 1985.

*Primary Examiner*—Sean McGarry
(74) *Attorney, Agent, or Firm*—Perkins Coie LLP

(57) ABSTRACT

The invention relates to compositions comprising oligomers antisense to bacterial 16S or 23S rRNA and capable of selectively modulating the biological activity thereof, and methods for their use. More particularly, the invention relates to antisense oligomers directed to 16S or 23S rRNA found in one or more particular bacteria, or generally conserved among bacteria in general, and to pharmaceutical compositions and methods of treatment comprising the same.

6 Claims, 11 Drawing Sheets

ANTISENSE ANTIBACTERIAL METHOD AND COMPOSITION

This application is a continuation of U.S. Ser. No. 09/726,774, filed Nov. 29, 2000 now U.S. Pat. No. 6,677,153, which claims priority to U.S. Provisional Application No. 60/168,150, filed Nov. 29, 1999, each of which is incorporated in its entirety herein by reference.

FIELD OF THE INVENTION

The present invention relates to oligonucleotide compositions antisense to bacterial 16S and 23S rRNA and methods for use of such compositions in the treatment of bacterial infection in a mammal.

REFERENCES

Agrawal, S. et al., *Proc. Natl. Acad. Sci. USA* 87 (4):1401-5 (1990).
Ardhammar, M. et al., *J. Biomolecular Structure & Dynamics* 17 (1):33-40 (August 1999).
Attia, S. A. et al., *Antisense & Nucleic Acid Drug Dev.* 8 (3):207-14 (1998).
Bennett, M. R. et al., *Circulation* 92 (7):1981-1993 (1995).
Bonham, M. A. et al., *Nucleic Acids Res.* 23 (7):1197-1203 (1995).
Boudvillain, M. et al., *Biochemistry* 36 (10):2925-31 (1997).
Cross, C. W. et al., *Biochemistry* 36 (14):4096-107 (Apr. 8, 1997).
Dagle, J. M. et al., *Nucleic Acids Research* 28 (10):2153-7 (May 15, 2000).
Ding, D. et al., *Nucleic Acids Research* 24 (2):354-60 (Jan. 15, 1996).
Egholm, M. et al., *Nature* 365 (6446):566-8 (Oct. 7, 1993).
Felgner et al., *Proc. Nat. Acad. Sci. USA* 84:7413 (1987).
Gait, M. J.; Jones, A. S. and Walker, R. T., *J. Chem. Soc. Perkin I,* 1684-86 (1974).
Gee, J. E. et al., *Antisense & Nucleic Acid Drug Dev.* 8:103-111 (1998).
Good, L. and Nielsen, P. E., *Proc. Nat. Acad. Sci. USA* 95:2073-2076 (1998).
Huie, E. M. et al., *J. Org. Chem.* 57:4569 (1992).
Jones, A. S., MacCross, M. and Walker, R. T., *Biochem. Biophys. Acta* 365:365-377 (1973).
Lesnikowski, Z. J. et al., *Nucleic Acids Research* 18 (8):2109-15 (Apr. 25, 1990).
Matteucci, M., *Tetrahedron Lett.* 31:2385-88 (1990).
McElroy, E. B. et al., *Bioorg. Med. Chem. Lett.* 4:1071 (1994).
Mertes, M. P. and Coates, E. A., *J. Med. Chem.* 12:154-157 (1969).
Miller, P. S. et al., in: *Antisense Research Applications,* Crooke, S. T. and Lebleu, B., Eds., CRC Press, Boca Raton, Fla., p. 189. (1993).
Olgive, K. K. and Cormier, J. F., *Tetrahedron Lett* 26:4159-4162 (1986).
Rahman, M. A. et al., *Antisense Res Dev* 1 (4):319-27 (1991).
Roughton, A. L. et al., *J. Am. Chem. Soc.* 117:7249 (1995).
Stein, D. et al., *Antisense & Nucleic Acid Drug Dev.* 7 (3):151-7 (June 1997); see also
Summerton, J. et al., *Antisense & Nucleic Acid Drug Dev.* 7 (2):63-70 (April 1997).
Toulme, J. J. et al., *Biochimie* 78 (7):663-73 (1996).
Vasseur, J. J. et al., *J. Am. Chem. Soc.* 114:4006 (1992).

BACKGROUND OF THE INVENTION

Currently, there are several types of antibiotics in use against bacterial pathogens, with a variety of anti-bacterial mechanisms. Beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamycin. These compounds target the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. Where the antibiotic acts by inhibiting a bacterial enzyme, such as for sulfonamides, point mutations in the target enzyme may confer resistance.

The appearance of antibiotic resistance in many pathogenic bacteria, in many cases involving multi-drug resistance, has raised the specter of a pre-antibiotic era in which many bacterial pathogens are simply untreatable by medical intervention. There are two main factors that could contribute to this scenario. The first is the rapid spread of resistance and multi-resistance genes across bacterial strains, species, and genera by conjugative elements, the most important of which are self-transmissible plasmids. The second factor is a lack of current research efforts to find new types of antibiotics, due in part to the perceived investment in time and money needed to find new antibiotic agents and bring them through clinical trials, a process that may require a 20-year research effort in some cases.

In addressing the second of these factors, some drug-discovery approaches that may accelerate the search for new antibiotics have been proposed. For example, efforts to screen for and identify new antibiotic compounds by high-throughput screening have been reported, but to date no important lead compounds have been discovered by this route.

Several approaches that involve antisense agents designed to block the expression of bacterial resistance genes or to target cellular RNA targets, such as the rRNA in the 30S ribosomal subunit, have been proposed (Good et al., 1998; Rahman et al., 1991). In general, these approaches have been marginally successful, presumably because of poor uptake of the antisense agent (e.g., Summerton et al., 1997), or the requirement that the treated cells show high permeability for antibiotics (Good et al., 1998).

There is thus a growing need for new antibiotics that (i) are not subject to the principal types of antibiotic resistance currently hampering antibiotic treatment of bacteria, (ii) can be developed rapidly and with some reasonable degree of predictability as to target-bacteria specificity, (iii) can also be designed for broad-spectrum activity, (iv) are effective at low doses, meaning, in part, that they are efficiently taken up by wild-type bacteria or even bacteria that have reduced permeability for antibiotics, and (v) show few side effects.

SUMMARY OF THE INVENTION

In one aspect, the invention provides an antibacterial compound, consisting of a substantially uncharged antisense oligomer containing from 8 to 40 nucleotide subunits, including a targeting nucleic acid sequence at least 10 nucleotides in length which is complementary to a bacterial 16S or 23S rRNA nucleic acid sequence. Each of the subunits comprises a 5- or 6-membered ring supporting a base-pairing moiety effective to bind by Watson-Crick base pairing to a respective nucleotide base in the bacterial nucleic acid sequence. Adjacent subunits are joined by uncharged linkages selected from the group consisting of: uncharged phosphoramidate, phosphorodiamidate, carbonate, carbamate, amide, phosphotriester, alkyl phosphonate, siloxane, sulfone, sulfonamide, sulfamate, thioformacetyl, and methylene-N-methylhydroxylamino, or by charged linkages selected from the group consisting of phosphate, charged phosphoramidate and phosphorothioate. The ratio of uncharged linkages to charged linkages in the oligomer is at least 4:1, preferably at least 5:1, and more preferably at least 8:1. In one embodiment, the oligomer is fully uncharged.

Preferably, the oligomer is able to hybridize with the bacterial sequence at a Tm substantially greater than the Tm of a duplex composed of a corresponding DNA and the same bacterial sequence. Alternatively, the oligomer is able to hybridize with the bacterial sequence at a $T_m$ substantially greater than 37° C., preferably greater than 50° C., and more preferably in the range of 60-80° C.

In one embodiment, the oligomer is a morpholino oligomer. The uncharged linkages, and, in one embodiment, all of the linkages, in such an oligomer are preferably selected from the group consisting of the structures presented in FIGS. 2A through 2D. Particularly preferred are phosphorodiamidate-linked oligomers, as represented at FIG. 2B, where $X=NR_2$, R being hydrogen or methyl, $Y=O$, and $Z=O$.

The length of the oligomer is preferably 12 to 25 subunits. In one embodiment, the oligomer is a phosphorodiamidate-linked morpholino oligomer having a length of 15 to 20 subunits, and more preferably 17-18 subunits.

In selected embodiments, the targeting sequence is a broad spectrum sequence selected from the group consisting of SEQ ID NOs: 15, 16, and 21-25. In other embodiments, the targeting sequence is complementary to a Gram-positive bacterial 16S rRNA consensus sequence, e.g., SEQ ID NOs: 27-28, or is complementary to a Gram-negative bacterial 16S rRNA consensus sequence, e.g. SEQ ID NOs: 29-30.

Other targeting sequences can be used for treatment of an infection produced by various organisms, for example:

(a) *E. coli*, where the sequence is selected from the group consisting of SEQ ID NO:32 and SEQ ID NO:35;

(b) *Salmonella thyphimurium*, where the sequence is selected from the group consisting of SEQ ID NO:18 and SEQ ID NO:36;

(c) *Pseudomonas aeruginosa*, where the sequence is selected from the group consisting of SEQ ID NO:40, SEQ ID NO:41, SEQ ID NO:42 and SEQ ID NO:43;

(d) *Vibrio cholera*, where the sequence is selected from the group consisting of SEQ ID NO:45, SEQ ID NO:46 and SEQ ID NO:47;

(e) *Neisseria gonorrhoea*, where the sequence is selected from the group consisting of SEQ ID NO:48, SEQ ID NO:49, SEQ ID NO:50 and SEQ ID NO:51;

(f) *Staphylococcus aureus*, where the sequence is selected from the group consisting of SEQ ID NO:53, SEQ ID NO:54 and SEQ ID NO:55;

(g) *Mycobacterium tuberculosis*, where the sequence is selected from the group consisting of SEQ ID NO:56, SEQ ID NO:57, SEQ ID NO:58 and SEQ ID NO:59;

(h) *Helicobacter pylori*, where the sequence is selected from the group consisting of SEQ ID NO:60, SEQ ID NO:61, SEQ ID NO:62 and SEQ ID NO:63;

(i) *Streptococcus pneumoniae*, where the sequence is selected from the group consisting of SEQ ID NO:64, SEQ ID NO:65, SEQ ID NO:66 and SEQ ID NO:67;

(j) *Treponema palladium*, where the sequence is selected from the group consisting of SEQ ID NO:69, SEQ ID NO:70 and SEQ ID NO:71;

(k) *Chlamydia trachomatis*, where the sequence is selected from the group consisting of SEQ ID NO:72, SEQ ID NO:73, SEQ ID NO:74 and SEQ ID NO:75;

(l) *Bartonella henselae*, where the sequence is selected from the group consisting of SEQ ID NO:76, SEQ ID NO:77, SEQ ID NO:78 and SEQ ID NO:79;

(m) *Hemophilis influenza*, where the sequence is selected from the group consisting of SEQ ID NO:81, SEQ ID NO:82 and SEQ ID NO:83;

(n) *Shigella dysenterae*, where the sequence is presented as SEQ ID NO:88; or (o) *Enterococcus faecium*, where the sequence is presented as SEQ ID NO: 92.

In other embodiments, the targeting sequence is an antisense oligomer sequence selected from one of the following groups, for use in treatment of an infection produced by:

(a) *E. coli, Salmonella thyphimurium* and *Shigella dysenterae*, where the sequence is selected from the group consisting of SEQ ID NO:15, SEQ ID NO:16, SEQ ID NO:33, SEQ ID NO:34, SEQ ID NO:38, SEQ ID NO:39 and SEQ ID NO:86 and SEQ ID NO:87;

(b) *E. coli, Salmonella thyphimurium* and *Hemophilis influenza*, where the sequence is presented as SEQ ID NO:31;

(c) *E. coli* and *Shigella dysenterae*, where the sequence is presented as SEQ ID NO:17;

(d) *E. coli, Salmonella thyphimurium, Shigella dysenterae, Hemophilis influenza* and *Vibrio cholera*, where the sequence is presented as SEQ ID NO:44;

(e) *Staphylococcus aureus* and *Bartonella henselae*, where the sequence is presented as SEQ ID NO:52;

(f) *Salmonella thyphimurium, Hemophilis influenza* and *Treponema palladium*, where the sequence is presented as SEQ ID NO:68; or (g) *E. coli, Salmonella thyphimurium, Shigella dysenterae, Hemophilis influenza* and *Neisseria gonorrhoea*, where the sequence is presented as SEQ ID NO:84.

In a related aspect, the invention provides a method of treating a bacterial infection in a human or mammalian animal subject, by administering to the subject, in a pharmaceutically effective amount, a substantially uncharged antisense oligomer as described above. Various selected embodiments of the oligomer and the target sequence are as described above. Preferably, the antisense oligomer is administered in an amount and manner effective to result in a peak blood concentration of at least 200-400 nM antisense oligomer. The method can be used, for example, for treating bacterial infections of the skin, wherein administration is by a topical route, or for use in treating a bacterial respiratory infection, wherein administration is by inhalation.

In a further related aspect, the invention provides a livestock and poultry food composition containing a food grain supplemented with a subtherapeutic amount of an antibacterial compound, said compound consisting of a substantially uncharged antisense oligomer as described above.

Also contemplated is, in a method of feeding livestock and poultry with a food grain supplemented with subtherapeutic levels of an antibiotic, an improvement in which the food grain is supplemented with a subtherapeutic amount of an antibacterial compound of the type described above.

These and other objects and features of the invention will become more fully apparent when the following detailed description is read in conjunction with the accompanying figures and examples.

DETAILED DESCRIPTION OF THE INVENTION

I. Definitions

Figure 1A:
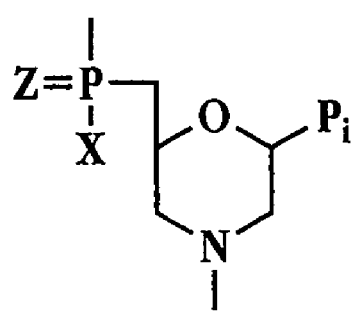
FIG. 1 shows several preferred morpholino-type subunits having 5-atom (A), six-atom (B) and seven-atom (C-D) linking groups suitable for forming polymers.

The terms below, as used herein, have the following meanings, unless indicated otherwise:

As used herein, the term "16S ribosomal RNA", also termed "16S rRNA", refers to RNA which is part of the structure of a ribosome and is involved in the synthesis of proteins.

The term "polynucleotide" as used herein refers to a polymeric molecule having a backbone which supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded RNA, double-stranded RNA, single-stranded DNA or double-stranded DNA). "Polynucleotides" include polymers with nucleotides which are an N- or C-glycoside of a purine or pyrimidine base, and polymers containing non-standard nucleotide backbones, for example, backbones formed using phosphorodiamidate morpholino chemistry, polyamide linkages (e.g., peptide nucleic acids or PNAs) and other synthetic sequence-specific nucleic acid molecules.

As used herein, the terms "antisense oligonucleotide" and "antisense oligomer" are used interchangeably and refer to a sequence of nucleotide bases and a subunit-to-subunit backbone that allows the antisense oligomer to hybridize to a target nucleic acid (e.g., RNA) sequence by Watson-Crick base pairing, to form a nucleic acid:oligomer heteroduplex within the target sequence. The oligomer may have exact sequence complementarity to the target sequence or near complementarity. In one exemplary application, such an antisense oligomer may block or inhibit the function of 16S or 23S rRNA containing a given target sequence, may bind to a double-stranded or single stranded portion of the 16S or 23S rRNA target sequence, may inhibit mRNA translation and/or protein synthesis, and may be said to be "directed to" a sequence with which it specifically hybridizes.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion (i.e., the percentage) of bases in opposing strands that are expected to form hydrogen bonds with each other, according to generally accepted base-pairing rules.

As used herein, the term "consensus sequence", relative to 16S or 23S rRNA sequences, refers to a sequence which is common to or shared by a particular group of organisms. The consensus sequence shows the nucleic acid most commonly found at each position within the polynucleotide. For example, a Gram-negative bacterial 16S or 23S rRNA consensus sequence is common to Gram-negative bacteria and generally not found in bacteria that are not Gram-negative.

As used herein, the term "conserved", relative to 16S or 23S rRNA sequences, also refers to a sequence which is common to or shared by a particular group of organisms (e.g., bacteria).

A "subunit" of an oligonucleotide or oligonucleotide analog refers to one nucleotide (or nucleotide analog) unit of the oligomer. The term may refer to the nucleotide unit with or without the attached intersubunit linkage, although, when referring to a "charged subunit", the charge typically resides within the intersubunit linkage (e.g. a phosphate or phosphorothioate linkage).

As used herein, a "morpholino oligomer" refers to a polymeric molecule having a backbone which supports bases capable of hydrogen bonding to typical polynucleotides, wherein the polymer lacks a pentose sugar backbone moiety, and more specifically lacks a ribose backbone linked by phosphodiester bonds which is typical of nucleotides and nucleosides, but instead contains a ring nitrogen with coupling through the ring nitrogen. A typical "morpholino" oligonucleotide is composed of morpholino subunit structures of the form shown in FIGS. 1A-1D, where (i) the structures are linked together by phosphorous-containing linkages, one to three atoms long, joining the morpholino nitrogen of one subunit to the 5' exocyclic carbon of an adjacent subunit, and (ii) B is a purine or pyrimidine base-pairing moiety effective to bind, by base-specific hydrogen bonding, to a base in a polynucleotide.

As used herein, the term "PMO" refers to a phosphorodiamidate morpholino oligomer, as further described below, wherein the oligomer is a polynucleotide of about 8-40 bases in length, preferably 12-25 bases in length. This preferred aspect of the invention is illustrated in FIG. 2B, where the two subunits are joined by a phosphorodiamidate linkage.

As used herein, a "nuclease-resistant" oligomeric molecule (oligomer) is one whose backbone is not susceptible to nuclease cleavage of a phosphodiester bond. Exemplary nuclease resistant antisense oligomers are oligonucleotide analogs such as phosphorothioate and phosphate-amine DNA (pnDNA), both of which have a charged backbone, and methyl phosphonate and phosphoramidate- or phosphorodiamidate-linked morpholino oligonucleotides, which have uncharged backbones.

A "2'-O-allyl (or alkyl) modified oligonucleotide" is an oligoribonucleotide in which the 2' hydroxyl is converted to an allyl or alkyl ether, respectively. The alkyl ether is typically a methyl ether.

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Lower alkyl" refers to an alkyl radical of one to six carbon atoms, and preferably one to four carbon atoms, as exemplified by methyl, ethyl, isopropyl, n-butyl, isobutyl, and t-butyl.

As used herein, a first sequence is an "antisense sequence" with respect to a second sequence if a polynucleotide with a first sequence specifically binds to, or specifically hybridizes with, a polynucleotide which has a second sequence, under physiological conditions.

As used herein, a "base-specific intracellular binding event involving a target RNA" refers to the specific binding of an oligomer to a target RNA sequence inside a cell. The base specificity of such binding is sequence specific. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, such that the heteroduplex is resistant to in vivo degradation by ubiquitous intracellular and extracellular nucleases.

As used herein, the term "broad spectrum bacterial sequence", with reference to bacterial 16S rRNA, refers to an oligonucleotide of the invention which is antisense to some segment of most if not all of the bacterial 16S rRNA sequences described herein. A corresponding definition applies to bacterial 23S rRNA. Exemplary broad spectrum bacterial sequences described herein include the antisense oligomers presented as SEQ ID NO:21, SEQ ID NO:22 and SEQ ID NO:23, which are antisense to an *Escherichia coli* (*E. coli*), *Salmonella thyphimurium* (*S. thyphi*), *Pseudomonas aeruginosa* (*P. aeruginosa*), *Vibrio cholera*, *Neisseria gonorrhoea* (*N. gonorrhoea*), *Staphylococcus aureus* (*Staph. aureus*), *Mycobacterium tuberculosis* (*Myco. tubercul.*), *Helicobacter pylori* (*H. pylori*), *Streptococcus pneumoniae* (*Strep. pneumoniae*), *Treponema palladium* (*Treponema pallad.*), *Chlamydia trachomatis* (*Chlamydia trach.*), *Bartonella henselae* (*Bartonella hens.*), *Hemophilis influenza* (*H. influenza*) and *Shigella dysenterae* (*Shigella dys.*) 16S rRNA sequence (see Table 5A), and SEQ ID NOs 24-25, which are antisense to the 16s rRNA of the majority of these organisms (see Table 5B).

As used herein, the term "narrow spectrum bacterial sequence", with respect to 16S bacterial rRNA, refers to an oligonucleotide of the invention which is antisense to particular, but not most or all, bacterial 16S rRNA sequences described herein. Again, a corresponding definition applies to bacterial 23S rRNA. A narrow spectrum bacterial sequence may be specific to one or more different bacteria, e.g., an antisense oligomer which is antisense to *E. coli*, *S. thyphi* and *Shigella dys*. 16S rRNA, but not the other bacterial 16S rRNA sequences described herein, as exemplified by SEQ ID NO:31; or an antisense oligomer which is antisense to the *E. coli* 16S rRNA sequence, but not the other bacterial 16S rRNA sequences described herein, as exemplified by SEQ ID NO:32.

As used herein, the term "modulating expression" relative to oligonucleotides refers to the ability of an antisense oligomer to either enhance or reduce the expression of a given protein by interfering with the expression or translation of RNA.

As used herein, "effective amount" relative to an antisense oligomer refers to the amount of antisense oligomer administered to a mammalian subject, either as a single dose or as part of a series of doses, that is effective to inhibit a biological activity, e.g., expression of a selected target nucleic acid sequence.

As used herein, "treatment" of an individual or a cell is any type of intervention provided as a means to alter the natural course of the individual or cell. Treatment includes, but is not limited to, administration of a pharmaceutical composition, and may be performed either prophylactically or subsequent to the initiation of a pathologic event or contact with an etiologic agent.

As used herein, the term "improved therapeutic outcome", relative to a patient diagnosed as infected with a particular bacteria, refers to a slowing or diminution in the growth of the bacteria and/or a decrease in, or elimination of, detectable symptoms typically associated with infection by that particular bacteria.

II. Antisense Oligomers: Selection Criteria

Antisense compounds employed in the invention preferably meet several criteria of structure and properties, considered in the subsections below.

A. Base Sequence and Length

The antisense compound has a base sequence targeted against a selected RNA target sequence. The region of complementarity with the target RNA sequence may be as short as 10-12 bases, but is preferably 13-20 bases, and more preferably 17-20 bases, in order to achieve the requisite binding $T_m$, as discussed below.

In some cases, the target for modulation of the activity of 16S rRNA using the antisense oligomers of the invention is a sequence in a double stranded region of the 16s rRNA, such as the peptidyl transferase center, the alpha-sarcin loop or the mRNA binding region of the 16S rRNA sequence. In other cases, the target for modulation of gene expression is a sequence in a single stranded region of bacterial 16S or 23S rRNA. The target may be a consensus sequence for bacterial 16S or 23S rRNAs in general, a sequence common to the 16s or 23S rRNA of one or more types of bacteria (e.g., Gram positive or Gram negative bacteria), or specific to a particular 16S or 23S rRNA sequence.

The oligomer may be 100% complementary to the bacterial RNA target sequence, or it may include mismatches, e.g., to accommodate variants, as long as the heteroduplex formed between the oligomer and bacterial RNA target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex and the position of the mismatch(es) in the duplex, according to well understood principles of duplex stability. Although such an antisense oligomer is not necessarily 100% complementary to the bacterial RNA target sequence, it is effective to stably and specifically bind to the target sequence such that a biological activity of the nucleic acid target, e.g., expression of bacterial protein(s) is modulated.

Oligomers as long as 40 bases may be suitable, where at least the minimum number of bases, e.g., 10-15 bases, are complementary to the target RNA sequence. In general, however, facilitated or active uptake in cells is optimized at oligomer lengths less than about 30, preferably less than 25, and more preferably 20 or fewer bases. For PMO oligomers, described further below, an optimum balance of binding stability and intake generally occurs at lengths of 17-18 bases.

B. Duplex Stability (Tm)

The oligomer must form a stable hybrid duplex with the target sequence. Preferably, the oligomer is able to hybridize to the target RNA sequence with a Tm substantially greater than the Tm of a duplex composed of a corresponding DNA and the same target RNA sequence. The antisense oligomer will have a binding Tm, with respect to a complementary-sequence RNA, of greater than body temperature and preferably greater than 50° C. Tm's in the range 60-80° C. or greater are preferred. The Tm of an antisense compound with respect to complementary-sequence RNA may be measured by conventional methods, such as those described by Hames et al., Nucleic Acid Hybridization, IRL Press 1985, pp. 107-108. According to well known principles, the Tm of an oligomer compound, with respect to a complementary-base RNA hybrid, can be increased by increasing the length (in basepairs) of the heteroduplex. At the same time, for purposes of optimizing cell transport, it may be advantageous to limit the size of the oligomer. For this reason, compounds that show high Tm (50° C. or greater) at a length of 15-20 bases or less will be preferred over those requiring 20+ bases for high Tm values.

Increasing the ratio of C:G paired bases in the duplex is also known to generally increase in the Tm of an oligomer compound. Studies in support of the invention suggest that maximizing the number of C bases in the antisense oligomer is particularly favorable.

C. Uptake by Cells

In order to achieve adequate intracellular levels, the antisense oligomer must be actively taken up by cells, meaning that the compound is taken up by facilitated or active transport, if administered in free (non-complexed) form, or is taken by an endocytotic mechanism if administered in complexed form.

When the antisense compound is administered in complexed form, the complexing agent typically is a polymer, e.g., a cationic lipid, polypeptide, or non-biological cationic polymer, having an opposite charge to a net charge on the antisense compound. Methods of forming complexes, including bilayer complexes, between anionic oligonucleotides and cationic lipid or other polymer components are well known. For example, the liposomal composition Lipofectin® (Felgner et al., 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies. The ability of the antisense agent to resist cellular nucleases promotes survival and ultimate delivery of the agent to the cell cytoplasm.

In the case where the agent is administered in free form, the agent should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can enhance cell uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages.

An oligomer may also contain both negatively and positively charged backbone linkages, as long as two opposite charges are substantially offsetting, and preferably do not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle). The net charge is preferably neutral or at most 1-2 net charges per oligomer, as above.

In addition to being substantially or fully uncharged, the antisense agent is preferably a substrate for a membrane transporter system (i.e. a membrane protein or proteins) capable of facilitating transport or actively transporting the oligomer across the cell membrane. This feature may be determined by one of a number of tests, as follows, for oligomer interaction or cell uptake.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

A third test relies on the ability of certain antisense compounds to effectively inhibit bacterial growth when targeted against bacterial 16S or 23S rRNA. Studies carried out in support of the present invention show that the inhibition requires active or facilitated transport across bacterial cell membranes. The test compound is prepared with a target 16S sequence that has been demonstrated to be effective in inhibiting bacterial growth. For example, SEQ ID. NOS: 1-3 herein are representative sequences against *E. coli* 16S rRNA. The compound is added to the growing bacterial culture at increasing concentrations, typically between 10 nM and 1 mM. The ability to inhibit bacterial growth is measured from number of cell colonies cell counts at 24-72 hours after addition of the test compound. Compounds which can produce a 50% inhibition at a concentration of between about 100-500 nM or lower are considered to be good candidates for active transport.

Figure 4:
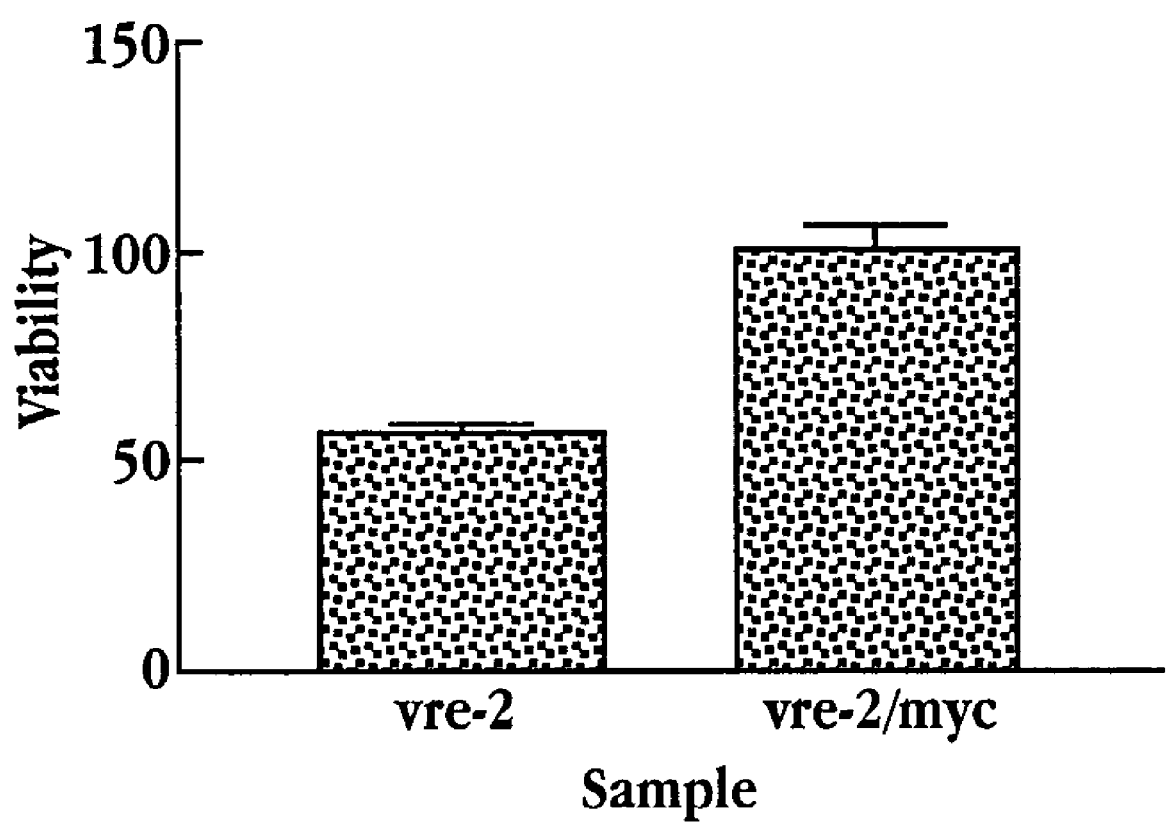
FIG. 4 depicts the results of a study on the effect of a phosphorodiamidate morpholino antisense oligomer (PMO) designated VRE-2 (SEQ ID NO: 92) (see Table 10), targeted against an *Enterococcus faecium* 16S rRNA sequence, alone or in combination with 50 µM of an oligomer antisense to c-myc (SEQ ID NO: 139), on bacterial colony formation in *E. coli*, presented as percent viability.

As shown by the data in FIG. 4, 500 nM of PMO antisense oligomer targeted against VRE (vancomycin-resistant *Enterococcus*) 16s rRNA, having SEQ ID NO: 92, inhibited growth in VRE by about 50%. It was also observed that addition of a comparatively large concentration (50 µM) of a nontarget sequence PMO (antisense to c-myc; SEQ ID NO: 139) essentially nullified this effect, suggesting that the transport mechanism has a finite capacity.

D. mRNA Resistance to RNaseH

Two general mechanisms have been proposed to account for inhibition of expression by antisense oligonucleotides. (See e.g., Agrawal et al., 1990; Bonham et al., 1995; and Boudvillain et al., 1997). In the first, a heteroduplex formed between the oligonucleotide and mRNA is a substrate for RNaseH, leading to cleavage of the mRNA. Oligonucleotides belonging, or proposed to belong, to this class include phosphorothioates, phosphotriesters, and phosphodiesters (unmodified "natural" oligonucleotides). However, because such compounds would expose mRNA in an oligomer:RNA duplex structure to proteolysis by RNaseH, and therefore loss of duplex, they are suboptimal for use in the present invention. A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme et al., 1996), morpholino oligonucleotides, peptide nucleic acids (PNA's), 2'-O-allyl or 2'-O-alkyl modified oligonucleotides (Bonham, 1995), and N3'→P5' phosphoramidates (Gee, 1998; Ding).

A test oligomer can be assayed for its ability to protect mRNA against RNaseH by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

In testing an oligomer for suitability in the present invention, each of the properties detailed above is preferably met. It is recognized that the "substantially uncharged" feature is inherently met where the linkages are uncharged, and the target-sequence complementarity is achieved by base-sequence design. Thus, an oligomer is preferably tested as to its (i) Tm with respect to target RNA at a duplex length preferably between 12-20 basepairs, (ii) ability to be transported across cell membranes by active or facilitated transport, and (iii) ability to prevent RNA proteolysis by RNaseH in duplex form.

The antibacterial effectiveness of a given antisense oligomer may be further evaluated by screening methods known in the art. For example, the oligomer may be incubated with a bacterial culture in vitro and the effect on the target 16S RNA evaluated by monitoring (1) heteroduplex formation with the target sequence and/or non-target sequences, using procedures known to those of skill in the art, e.g., an electrophoretic gel mobility assay; (2) the amount of 16S mRNA, as determined by standard techniques such as RT-PCR or Northern blot; (3) the amount of bacterial protein production, as determined by standard techniques such as ELISA or Western blotting; or (4) the amount of bacterial growth in vitro for both bacteria known to have the 16S rRNA sequence targeted by a particular antisense oligomer and bacteria not predicted to have the target 16S rRNA sequence.

Candidate antisense oligomers may also be evaluated, according to well known methods, for acute and chronic cellular toxicity, such as the effect on protein and DNA synthesis as measured via incorporation of $^3$H-leucine and $^3$H-thymidine, respectively. In addition, various control oligonucleotides, e.g., one or more control oligonucleotides such as sense, nonsense or scrambled antisense sequences, or sequences containing mismatched bases, are generally included in the evaluation process, in order to confirm the specificity of binding of candidate antisense oligomers. The results of such tests allow discrimination of specific effects of antisense inhibition of gene expression from indiscriminate suppression. (See, e.g. Bennett et al., 1995). Sequences may be modified as needed to limit non-specific binding of antisense oligomers to non-target sequences, e.g., by changing the length or the degree of complementarity to the target sequence.

III. Uncharged Oligonucleotide Analogs

Examples of uncharged linkages that may be used in oligonucleotide analogs of the invention are shown in FIGS. 3A-3G. (As noted below, a small number of charged linkages, e.g. charged phosphoramidate or phosphorothioate, may also be incorporated into the oligomers.) The uncharged linkages include carbonate (3A, R=O) and carbamate (3A, R=NH$_2$) linkages, (Mertes; Gait); alkyl phosphonate and phosphotriester linkages (3B, R=alkyl or —O-alkyl) (Miller; Lesnikowski); amide linkages (3C); sulfones (3D, R$_1$, R$_2$=CH$_2$) (Roughten); sulfonamides (3D, R$_1$=NH, R$_2$=CH$_2$ or vice versa) (McElroy); sulfamates (3D, R$_1$, R$_2$=NH) (Huie); and a thioformacetyl linkage (3E) (Matteucci; Cross). The latter is reported to have enhanced duplex and triplex stability with respect to phosphorothioate antisense compounds (Cross). Also reported are the 3'-methylene-N-methylhydroxyamino compounds of structure 3F (Vasseur). In FIGS. 3A-3G, B represents a purine or pyrimidine base-pairing moiety effective to bind, by base-specific hydrogen bonding, to a base in a polynucleotide, preferably selected from adenine, cytosine, guanine and uracil. The linkages join nucleotide subunits, each consisting of a 5- or 6-membered ring supporting a base-pairing moiety effective to bind by Watson-Crick base pairing to a respective nucleotide base in the bacterial nucleic acid sequence. These subunits may comprise, for example, ribose rings, as in native nucleic acids, or morpholino rings, as described further below.

PNAs (peptide nucleic acids) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). However, PNA antisense agents have been observed to display slow membrane penetration in cell cultures, possibly due to poor uptake (transport) into cells. (See, e.g., Ardhammar, M. et al., 1999).

Oligomeric ribonucleotides substituted at the 2'-oxygen show high RNA binding affinities and, in comparison to unsubstituted ribonucleotides, reduced sensitivity to endogenous nucleases. Methyl-substituted ribonucleotides are reported to provide greater binding affinity and cellular uptake than those having larger 2'-oxygen substituents (e.g. ethyl, propyl, allyl, or pentyl).

One preferred oligomer structure employs morpholino-based subunits bearing base-pairing moieties, joined by uncharged linkages as outlined above. Especially preferred is a substantially uncharged morpholino oligomer such as illustrated by the phosphorodiamidate-linked compound shown in FIG. 3G. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein. Desirable chemical properties of the morpholino-based subunits are the ability to be linked in a oligomeric form by stable, uncharged backbone linkages, the ability of the polymer so formed to hybridize with a complementary-base target nucleic acid, including target RNA, with high Tm, even with oligomers as short as 10-14 bases, the ability of the oligomer to be actively transported into mammalian cells, and the ability of the oligomer:RNA heteroduplex to resist RNAse degradation.

Exemplary backbone structures for antisense oligonucleotides of the invention include the morpholino subunit types shown in FIGS. 1A-D, each linked by an uncharged, phosphorous-containing subunit linkage. In these figures, the X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Alkyl, alkoxy and thioalkoxy preferably include 1-6 carbon atoms, and more preferably 14 carbon atoms. Monosubstituted or disubstituted nitrogen preferably refers to lower alkyl substitution, and the cyclic structures are preferably 5- to 7-membered nitrogen heterocycles optionally containing 1-2 additional heteroatoms selected from oxygen, nitrogen, and sulfur. Z is sulfur or oxygen, and is preferably oxygen.

Figure 2A:
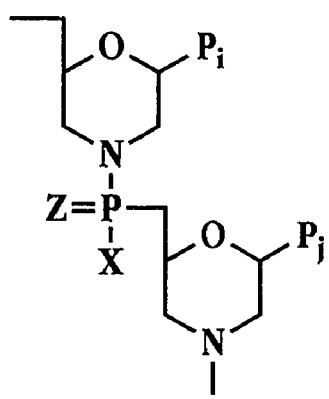
FIGS. 2A-D show the repeating subunit segment of exemplary morpholino oligonucleotides, designated A through D, constructed using subunits A-D, respectively, of FIG. 1.
Figure 2B:
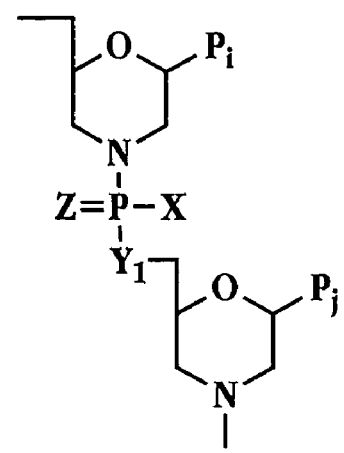

FIG. 1A shows a phosphorous-containing linkage which forms the five atom repeating-unit backbone shown in FIG. 2A, where the morpholino rings are linked by a 1-atom phosphoamide linkage.

Figure 1B:
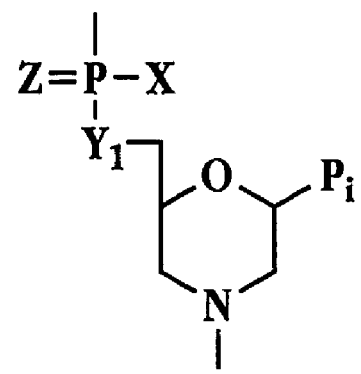

Subunit B in FIG. 1B is designed for 6-atom repeating-unit backbones, as shown in FIG. 2B. In FIG. 1B, the atom Y linking the 5' morpholino carbon to the phosphorous group may be sulfur, nitrogen, carbon or, preferably, oxygen. The X and Z moieties are as defined above. Particularly preferred morpholino oligonucleotides include those composed of morpholino subunit structures of the form shown in FIG. 2B, where X=NH$_2$ or N(CH$_3$)$_2$, Y=O, and Z=O.

Figure 1C:
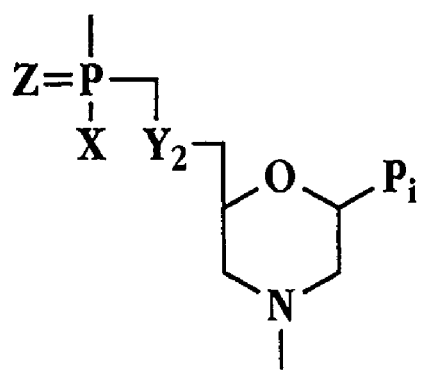
Figure 1D:
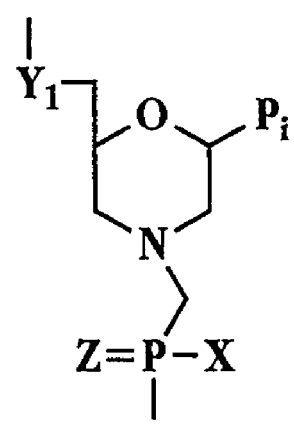
Figure 2C:
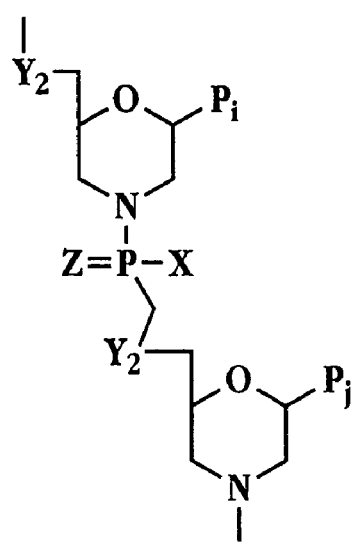
Figure 2D:
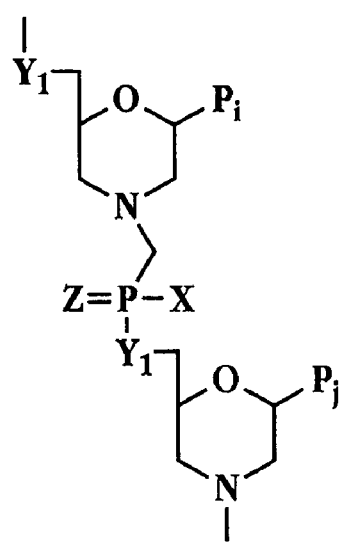
Figure 3A:
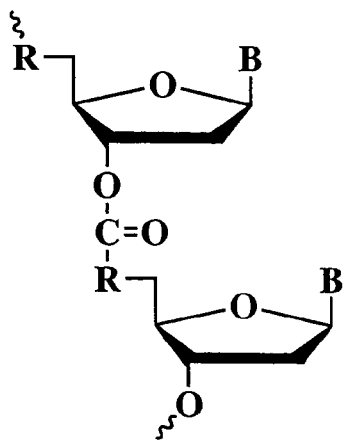
FIGS. 3A-3G show examples of uncharged linkage types in oligonucleotide analogs.
Figure 3B:
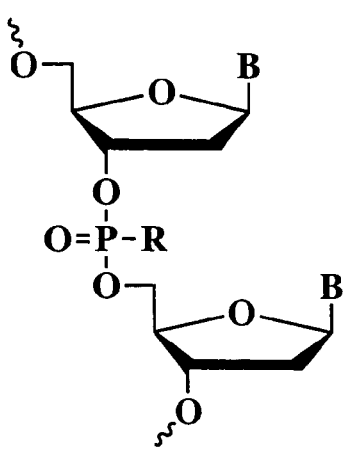
Figure 3C:
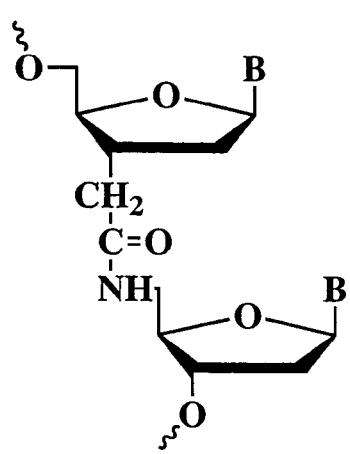
Figure 3D:
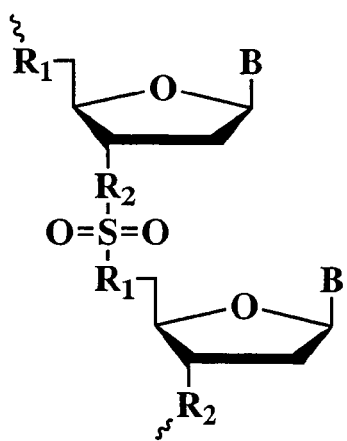
Figure 3E:
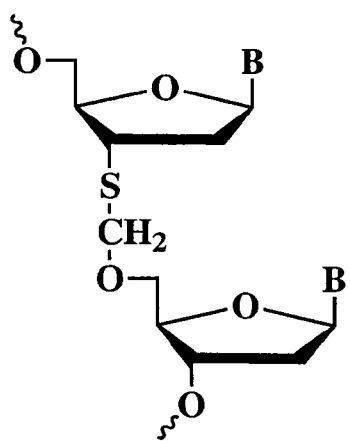
Figure 3F:
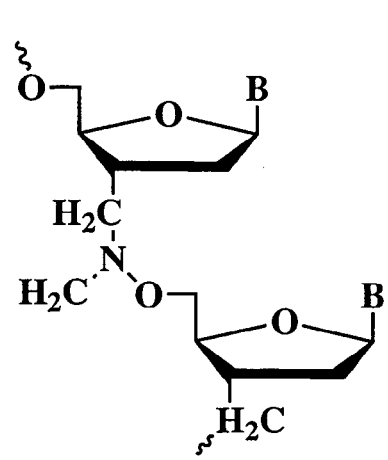
Figure 3G:
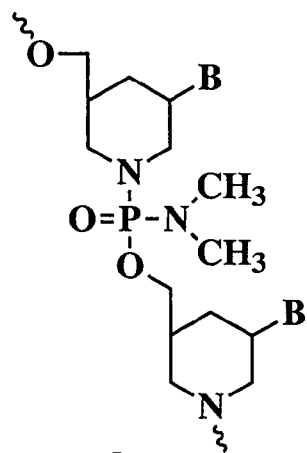

Subunits C-D in FIGS. 1C-D are designed for 7-atom unit-length backbones as shown for structures in FIGS. 2C and D. In Structure C, the X moiety is as in Structure B, and the moiety Y may be methylene, sulfur, or preferably oxygen. In Structure D, the X and Y moieties are as in Structure B. In all subunits depicted in FIGS. 1 and 2, each Pi and Pj is a purine or pyrimidine base-pairing moiety effective to bind, by base-specific hydrogen bonding, to a base in a polynucleotide, and is preferably selected from adenine, cytosine, guanine and uracil.

As noted above, the substantially uncharged oligomer may advantageously include a limited number of charged linkages, e.g. up to about 1 per every 5 uncharged linkages. In the case of the morpholino oligomers, such a charged linkage may be a linkage as represented by any of FIGS. 2A-D, preferably FIG. 2B, where X is oxide (—O$^-$) or sulfide (—S$^-$).

The antisense compounds of the invention can be synthesized by stepwise solid-phase synthesis, employing methods detailed in the references cited above. The sequence of subunit additions will be determined by the selected base sequence (see Sections IID and IV below). In some cases, it may be desirable to add additional chemical moieties to the oligomer compounds, e.g. to enhance the pharmacokinetics of the compound or to facilitate capture or detection of the compound. Such a moiety may be covalently attached, typically to the 5'- or 3'-end of the oligomer, according to standard synthesis methods. For example, addition of a polyethyleneglycol moiety or other hydrophilic polymer, e.g., one having 10-100 polymer subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an oligomer antisense, it is generally of course desirable to select chemical compounds of groups that are biocompatible and likely to be tolerated by a subject without undesirable side effects.

IV. Exemplary Bacterial Targets

*Escherichia coli* (*E. coli*) is a Gram negative bacteria that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain O157:H7 is estimated to cause 10,000 to 20,000 cases of infection in the United States annually (Federal Centers for Disease Control and Prevention). Hemorrhagic colitis is the name of the acute disease caused by *E. coli* O157:H7. Preschool children and the elderly are at the greatest risk of serious complications. *E. coli* strain O157:H7 was recently reported as the cause of death of four children who ate under cooked hamburgers from a fast-food restaurant in the Pacific Northwest.

*Salmonella thyphimurium* are Gram negative bacteria which cause various conditions that range clinically from localized gastrointestinal infections and gastroenterits (diarrhea, abdominal cramps, and fever) to enteric fevers (including typhoid fever) which are serious systemic illnesses. *Salmonella* infection also causes substantial losses of livestock.

Typical of Gram-negative bacilli, the cell wall of *Salmonella* spp. contains a complex lipopolysaccharide (LPS) structure that is liberated upon lysis of the cell and may function as an endotoxin, which contributes to the virulence of the organism.

Contaminated food is the major mode of transmission for non-typhoidal salmonella infection, due to the fact that *Salmonella* survive in meats and animal products that are not thoroughly cooked. The most common animal sources are chickens, turkeys, pigs, and cows, in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal *Salmonella* infection. Non-typhoidal salmonellosis is controlled by hygienic slaughtering practices and thorough cooking and refrigeration of food. Antibiotics are indicated for systemic disease, and Ampicillin has been used with some success. However, in patients under treatment with excessive amounts of antibiotics, patients under treatment with immunosuppressive drugs, following gastric surgery, and in patients with hemolytic anemia, leukemia, lymphoma, or AIDS, *Salmonella* infection remains a medical problem.

*Pseudomonas* spp. are motile, Gram-negative rods which are clinically important because they are resistant to most antibiotics, and are a major cause of hospital acquired (nosocomial) infections. Infection is most common in: immunocompromised individuals, burn victims, individuals on respirators, individuals with indwelling catheters, IV narcotic users and individuals with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Vibrio cholerae* is a Gram negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting; however, death can occur from dehydration and loss of essential electrolytes. Antibiotics such as tetracycline have been demonstrated to shorten the course of the illness, and oral vaccines are currently under development.

*Neisseria gonorrhoeae* is a Gram negative coccus, which is the causative agent of the common sexually transmitted disease, gonorrhea. *Neisseria gonorrhoeae* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram positive coccus which normally colonizes the human nose and is sometimes found on the skin. Staphylococcus can cause bloodstream infections, pneumonia, and surgical-site infections in the hospital setting (i.e., nosocomial infections). *Staph. aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently a vancomycin-resistant *Staph. aureus* isolate has also been identified in Japan.

*Mycobacterium tuberculosis* is a Gram positive bacterium which is the causative agent of tuberculosis, a sometimes crippling and deadly disease. Tuberculosis is on the rise globally and is the leading cause of death from a single infectious disease (with a current death rate of three million people per year). It can affect several organs of the human body, including the brain, the kidneys and the bones; however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin) for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin, which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram positive coccus and one of the most common causes of bacterial pneumonia as well as middle ear infections (otitis media) and meningitis. Each year in the United States, pneumococcal diseases account for approximately 50,000 cases of bacteremia; 3,000 cases of meningitis; 100,000-135,000 hospitalizations; and 7 million cases of otitis media. Pneumococcal infection causes an estimated 40,000 deaths annually in the United States. Children less than 2 years of age, adults over 65 years of age, persons of any age with underlying medical conditions, including, e.g., congestive heart disease, diabetes, emphysema, liver disease, sickle cell, HIV, and those living in special environments, e.g., nursing homes and long-term care facilities, are at highest risk for infection.

Drug-resistant *S. pneumoniae* strains have become common in the United States, with many penicillin-resistant pneumococci also resistant to other antimicrobial drugs, such as erythromycin or trimethoprim-sulfamethoxazole.

*Treponema pallidum* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States, and it is estimated that 4 million new cases occur each year. The highest rates of infection are in 15 to 19 year olds. Chlamydia is a major cause of non-gonococcal urethritis (NGU), cervicitis, bacterial vaginitis, and pelvic inflammatory disease (PID). Chlamydia infections may have very mild symptoms or no symptoms at all; however, if left untreated, *Chlamydia* infections can lead to serious damage to the reproductive organs, particularly in women. Antibiotics such as azithromycin, erythromycin, ofloxacin, amoxicillin or doxycycline are typically prescribed to treat *Chlamydia* infection.

*Bartonella henselae*. Cat Scratch Fever (CSF) or cat scratch disease (CSD) is a disease of humans acquired through exposure to cats, caused by a Gram negative rod originally named *Rochalimaea henselae*, and currently known as *Bartonella henselae*. Symptoms include fever and swollen lymph nodes. CSF is generally a relatively benign, self-limiting disease in people; however, infection with *Bartonella henselae* can produce distinct clinical symptoms in immunocompromised people, including acute febrile illness with bacteremia, bacillary angiomatosis, peliosis hepatis, bacillary splenitis, and other chronic disease manifestations such as AIDS encephalopathy.

The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram negative bacteria; six types of which are known, with most *H. influenza*-related disease caused by type B, or "HIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella dys.*) is a Gram negative rod which causes dysentary. In the colon, the bacteria enter mucosal cells and divide within mucosal cells, resulting in an extensive inflammatory response.*Shigella* infection can cause severe diarrhea which may lead to dehydration and can be dangerous for the very young, very old or chronically ill. *Shigella dys.* forms a potent toxin (shiga toxin), which is cytotoxic, enterotoxic, and neurotoxic and acts as a inhibitor of protein synthesis. Resistance to antibiotics such as ampicillin and TMP-SMX has developed; however, treatment with newer, more expensive antibiotics such as ciprofloxacin, norfloxacin and enoxacin, remains effective.

*Enterococcus faecium*. Enterococci are a component of the normal flora of the gastrointestinal and female urogenital tracts, however, recent studies indicate that pathogenic *Enterococci* can be transmitted directly in the hospital setting. (See, e.g., Boyce, et al., *J Clin Microbiol* 32, 1148-53, 1994) *Enterococci*, have been recognized as a cause of nosocomial infection and some strains are resistant to multiple antimicrobial drugs. The most common *Enterococci*-associated nosocomial infections are urinary tract infections, post-surgical infections and bacteremia (Murray B E, *Clin Microbiol* 3, 46-65, Rev. 1990; Moellering R C Jr., *Clin Infect Dis* 14, 1173-8, 1992; Schaberg D R et al., *Am J Med* 91(Suppl 3B), 72S-75S, 1991).

Vancomycin has been used extensively to treat *Enterococcus* infection since the late 1970s. Recently, a rapid increase in the incidence of infection and colonization with vancomycin-resistant enterococci (VRE) has been reported. The observed resistance is of concern due to (1) the lack of effective antimicrobial therapy for VRE infections because most VRE are also resistant to drugs previously used to treat such infections, i.e., penicillin and aminoglycosides (CDC. MMWR 42:597-9, 1993; Handwerger, et al., *Clin Infect Dis* 16, 750-5, 1993); and (2) the possibility that the vancomycin-resistant genes present in VRE can be transferred to other gram-positive microorganisms.

Resistance to vancomycin and other glycopeptide antibiotics has been associated with the synthesis of a modified cell-wall precursor, terminating in D-lactate which has a lower affinity for antibiotics such as vancomycin.

*Listeria* is a genus of Gram-positive, motile bacteria found in human and animal feces. *Listeria monocytogenes* causes such diseases as meningoencephalitis and meningitis. In cattle and sheep, listeria infection causes encephalitis and spontaneous abortion.

Veterinary applications. A healthy microflora in the gastro-intestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacteria such as *Salmonella, Campylobacter, Enterococci, Tularemia* and *E. coli*. Bacterial infection in these animals often necessitates therapeutic intervention, which has treatment costs as well being frequently associated with a decrease in productivity.

As a result, livestock are routinely treated with antibiotics to maintain the balance of flora in the gastrointestinal tract. The disadvantages of this approach are the development of antibiotic resistant bacteria and the carry over of such antibiotics into resulting food products.

V. Exemplary 16S rRNA Antisense Oligomers

In one embodiment, the antisense oligomers of the invention are designed to hybridize to a region of a bacterial 16S rRNA nucleic acid sequence under physiological conditions, with a $T_m$ substantially greater than 37° C., e.g., at least 50° C. and preferably 60° C.-80° C. The oligomer is designed to have high binding affinity to the nucleic acid and may be 100% complementary to the 16S rRNA nucleic acid target sequence, or it may include mismatches, as further described above.

In various aspects, the invention provides an antisense oligomer having a nucleic acid sequence effective to stably and specifically bind to a target sequence selected from the group consisting of 16S rRNA sequences which have one or more of the following characteristics: (1) a sequence found in a double stranded region of a 16s rRNA, e.g., the peptidyl transferase center, the alpha-sarcin loop and the mRNA binding region of the 16S rRNA sequence; (2) a sequence found in a single stranded region of a bacterial 16s rRNA; (3) a sequence specific to a particular strain of a given species of bacteria, i.e., a strain of *E. coli* associated with food poisoning; (4) a sequence specific to a particular species of bacteria; (5) a sequence common to two or more species of bacteria; (6) a sequence common to two related genera of bacteria (i.e., bacterial genera of similar phylogenetic origin); (7) a sequence generally conserved among Gram-negative bacterial 16S rRNA sequences; (6) a sequence generally conserved among Gram-positive bacterial 16S rRNA sequences; or (7) a consensus sequence for bacterial 16S rRNA sequences in general.

Exemplary bacteria and associated GenBank Accession Nos. for 16S rRNA sequences are provided in Table 1, below.

TABLE 1

| Organism | GenBank Reference for 16S rRNA | SEQ ID NO: |
|---|---|---|
| *Escherichia coli* | X80725 | 1 |
| *Salmonella thyphimurium* | U88545 | 2 |
| *Pseudomonas aeruginosa* | AF170358 | 3 |
| *Vibrio cholera* | AF118021 | 4 |
| *Neisseria gonorrhoea* | X07714 | 5 |
| *Staphylococcus aureus* | Y15856 | 6 |
| *Mycobacterium tuberculosis* | X52917 | 7 |
| *Helicobacter pylori* | M88157 | 8 |
| *Streptococcus pneumoniae* | AF003930 | 9 |
| *Treponema palladium* | AJ010951 | 10 |
| *Chlamydia trachomatis* | D85722 | 11 |
| *Bartonella henselae* | X89208 | 12 |
| *Hemophilis influenza* | M35019 | 13 |
| *Shigella dysenterae* | X96966 | 14 |

It will be understood that one of skill in the art may readily determine appropriate targets for antisense oligomers, and design and synthesize antisense oligomers using techniques known in the art. Targets can be identified by obtaining the sequence of a target 16S or 23S nucleic acid of interest (e.g. from GenBank) and aligning it with other 16S or 23S nucleic acid sequences using, for example, the MacVector 6.0 program, a ClustalW algorithm, the BLOSUM 30 matrix, and default parameters, which include an open gap penalty of 10 and an extended gap penalty of 5.0 for nucleic acid alignments. An alignment may also be carried out using the Lasergene99 MegAlign Multiple Alignment program with a ClustalW algorithm run under default parameters.

For example, given the 16s rRNA sequences provided in Table 1 and other 16s rRNA sequences available in GenBank, one of skill in the art can readily align the 16s rRNA sequences of interest and determine which sequences are conserved among one or more different bacteria, and those which are specific to one or more particular bacteria. A similar alignment can be performed on 23S rRNA sequences.

As an illustration, the 16S rRNA sequences from the organisms shown in Table 1 were aligned using the Lasergene 99 MegAlign Multiple Alignment program, with a ClustalW algorithm and default parameters. Tables 2-5 show exemplary oligomers antisense to 16S rRNA of these bacterial species, including sequences targeting individual bacteria, multiple bacteria, and broad spectrum sequences. These oligomers were derived from the sequences in Table 1 and from the alignment performed as described above. As the Tables show, a number of sequences were conserved among different organisms.

Exemplary oligomers antisense to *E. coli* 16S rRNA (SEQ ID NO:32 and SEQ ID NO:35) were designed based on the sequence found at GenBank Accession No. X80725. Further exemplary oligomers antisense to *E. coli* 16S rRNA and one or more other bacterial 16S rRNA sequences are provided in Table 2A.

Exemplary oligomers antisense to *Salmonella thyphimurium* 16S rRNA (SEQ ID NO:18 and SEQ ID NO:36) were designed based on the sequence found at GenBank Accession No. U88545. Further exemplary oligomers antisense to *S. thyphi.* 16S rRNA and one or more other bacterial 16S rRNA sequences are provided in Table 2A.

Exemplary oligomers antisense to *Pseudomonas aeruginosa* 16S rRNA (SEQ ID NO:40, SEQ ID NO:41, SEQ ID NO:42 and SEQ ID NO:43) were designed based on the sequence found at GenBank Accession No. AF170358.

Exemplary oligomers antisense to *Vibrio cholera* 16S rRNA (SEQ ID NO:45, SEQ ID NO:46 and SEQ ID NO:47) were designed based on the sequence found at GenBank Accession No. AF118021. A further exemplary oligomer, antisense to *Vibrio cholera* 16S rRNA and other bacterial 16S rRNA sequences (SEQ ID NO:44), is provided in Table 2A.

TABLE 2A

BACTERIAL 16s rRNA SEQUENCES AND ANTISENSE OLIGOMERS

| Organism | GenBank Reference | Native sequence | Antisense oligomer |
|---|---|---|---|
| *E. coli* (NS-1) | X80725 nt 446–466 | GAGTAAAGTTAAT GCAAAGGTATTAA | |
| *Shigella dys.* | X96966 nt 436–456 | ACCTTTGC | CTTTACT |
| | | | (SEQ ID NO: 17) |
| *E. coli* (BS-1) | X80725 nt 1270–1290 | TCATAAAGTGCGT GGACTACGACGCA | |
| *S. thyphi* | U88545 nt 1282–1302 | CGTAGTCC | CTTTATGAG |
| *Shigella dys.* | X96966 nt 1263–1283 | | (SEQ ID NO: 15) |
| *E. coli* | X80725 nt 1–21 | AGTTTGATCATGG AATCTGAGCCATG | |
| *S. thyphi* | U88545 nt 10–30 | CTCAGATT | ATCAAACT |
| *H. influenza* | M35019 nt 10–30 | | (SEQ ID NO: 31) |
| *E. coli* | X80725 nt 173–193 | ACGTCGCAAGCAC CCCTCTTTGTGCT | |
| | | AAAGAGGG | TGCGACGT |
| | | | (SEQ ID NO: 32) |
| *E. coli* | X80725 nt 643–663 | TTGAGTCTCGTAG ACCCCCCTCTACG | |
| *S. thyphi* | U88545 nt 652–672 | AGGGGGGT | AGACTCAA |
| *Shigella dys.* | X96966 nt 653–673 | | (SEQ ID NO: 33) |
| *E. coli* | X80725 nt 823–843 | GGTTGTGCCCTTG CCACGCCTCAAGG | |
| *S. thyphi* | U88545 nt 832–852 | AGGCGTGG | GCACAACC |
| *Shigella dys.* | X96966 nt 813–833 | | (SEQ ID NO: 34) |
| *E. coli* | X80725 nt 991–1011 | CGGAAGTTTTCAG TCTCATCTCTGAA | |
| | | AGATGAGA | AACTTCCG |
| | | | (SEQ ID NO: 35) |
| *S. thyphi* (NS-2) | U88545 nt 455–475 | GTTGTGGTTAATA GCTGCGGTTATTA | |
| | | ACCGCAGC | ACCACAAC |
| | | | (SEQ ID NO: 18) |
| *S. thyphi.* (BS-2) | U88545 nt 1261–1281 | CCTCGCGAGAGCA GGTCCGCTTGCTC | |
| *E. coli* | X80725 nt 1252–1272 | AGCGGACC | TCGCGAGG |
| *Shigella dys.* | X96966 nt 1242–1262 | | (SEQ ID NO: 16) |
| *S. thyphi.* | U88545 nt 1–21 | AAATTGAAGAGTT CATGATCAAACTC | |
| | | TGATCATG | TTCAATTT |
| | | | (SEQ ID NO: 36) |
| *S. thyphi.* | U88545 nt 181–201 | ACGTCGCAAGACC CCCTCTTTGGTCT | |
| *Shigella dys.* | X96966 nt 162–182 | AAAGAGGG | TGCGACGT |
| | | | (SEQ ID NO: 37) |
| *S. thyphi.* | U88545 nt 652–672 | TGAGTCTCGTAGA TACCCCCCTCTAC | |
| *E. coli* | X80725 nt 643–663 | GGGGGGTA | GAGACTCA |
| *Shigella dys.* | X96966 nt 633–653 | | (SEQ ID NO: 38) |
| *S. thyphi.* | U88545 nt 832–852 | GTTGTGCCCTTGA GCCACGCCTCAAG | |
| *E. coli* | X80725 nt 823–843 | GGCGTGGC | GGCACAAC |
| *Shigella dys.* | X96966 nt 813–833 | | (SEQ ID NO: 39) |
| *P. aeruginosa* | AF170358 nt 1–21 | ATGAAGAGGGCTT CAGAGAGCAAGC | |
| | | GCTCTCTG | CCTCTTCAT |
| | | | (SEQ ID NO: 40) |
| *P. aeruginosa* | AF170358 nt 107–127 | CGTCCTACGGGAG CCTGCTTTCTCCC | |
| | | AAAGCAGG | GTAGGACG |
| | | | (SEQ ID NO: 41) |

TABLE 2A-continued

BACTERIAL 16s rRNA SEQUENCES AND ANTISENSE OLIGOMERS

| Organism | GenBank Reference | Native sequence | Antisense oligomer |
|---|---|---|---|
| P. aeruginosa | AF170358 nt 578–598 | AGAGTATGGCAGA GGGTGGTG | CACCACCCTCTGC CATACTCT (SEQ ID NO: 42) |
| P. aeruginosa | AF170358 nt 758–778 | TTGGGATCCTTGA CTAAGATCTCAAG GATCTTAG | GATCCCAA (SEQ ID NO: 43) |
| Vibrio cholera | AF118021 nt 1–21 | ATTGAACGCTGGC | GGCCTGCCGCCAG |
| E. coli | X80725 nt 19–39 | GGCAGGCC | CGTTCAAT (SEQ ID NO: 44) |
| H. influenza | M35019 nt 26–46 | | |
| S. thyphi. | U88545 nt 18–48 | | |
| Shigella dys. | X96966 nt 9–29 | | |
| Vibrio cholera | AF118021 nt 157–177 | ATGTTTACGGACC AAAGAGGG | CCCTCTTTGGTCC GTAAACAT (SEQ ID NO: 45) |
| Vibrio cholera | AF118021 nt 625–645 | GCTAGAGTCTTGT AGAGGGGG | CCCCCTCTACAAG ACTCTAGC (SEQ ID NO: 46) |
| Vibrio cholera | AF118021 nt 805–825 | GAGGTTGTGACCT ARAGTCGT | ACGACTYTAGGTC ACAACCTC (SEQ ID NO: 47) |

1: Approximate nucleotide locations

Exemplary oligomers antisense to *Neisseria gonorrhoea* 16S rRNA (SEQ ID NO:48, SEQ ID NO:49, SEQ ID NO:50 and SEQ ID NO:51) were designed based on the sequence found at GenBank Accession No. X07714. These are shown in Table 2B, below.

Exemplary oligomers antisense to *Staphylococcus aureus* 16S rRNA (SEQ ID NO:53, SEQ ID NO:54 and SEQ ID NO:55) were designed based on the sequence found at GenBank Accession No. Y15856. A further exemplary oligomer, antisense to a *Staph. aureus* 16S rRNA and a *Bartonella henselae* 16S rRNA sequence (SEQ ID NO:52), is provided in Table 2B, below.

Exemplary oligomers antisense to *Mycobacterium tuberculosis* 16S rRNA (SEQ ID NO:56, SEQ ID NO:57, SEQ ID NO:58 and SEQ ID NO:59) were designed based on the sequence found at GenBank Accession No. X52917.

Exemplary oligomers antisense to *Helicobacter pylori* 16S rRNA (SEQ ID NO:60, SEQ ID NO:61, SEQ ID NO:62 and SEQ ID NO:63) were designed based on the sequence found at GenBank Accession No. M88157.

Exemplary oligomers antisense to *Streptococcus pneumoniae* 16S rRNA (SEQ ID NO:64, SEQ ID NO:65, SEQ ID NO:66 and SEQ ID NO:67) were designed based on the sequence found at GenBank Accession No. AF003930.

Exemplary oligomers antisense to *Treponema palladium* 16S rRNA (SEQ ID NO:69, SEQ ID NO:70 and SEQ ID NO:71) were designed based on the sequence found at GenBank Accession No. AJ010951. A further exemplary oligomer, antisense to *Treponema palladium* 16S rRNA and other 16S rRNA sequences (SEQ ID NO:68), is provided in Table 2B, below.

TABLE 2B

BACTERIAL 16s rRNA SEQUENCES AND ANTISENSE OLIGOMERS

| Organism | GenBank Reference | Native sequence | Antisense oligomer |
|---|---|---|---|
| N. gonorrhoea | X07714 nt 1–21 | TGAACATAAGAGT TTGATCCT | AGGATCAAACTCTTATGTTCA (SEQ ID NO: 48) |
| N. gonorrhoea | X07714 nt 183–203 | CGTCTTGAGAGGG AAAGCAGG | CCTGCTTTCCCTCTCAAGACG (SEQ ID NO: 49) |
| N. gonorrhoea | X07714 nt 654–674 | CGAGTGTGTCAGA GGGAGGTG | CACCTCCCTCTGACACACTCG (SEQ ID NO: 50) |

TABLE 2B-continued

BACTERIAL 16s rRNA SEQUENCES AND ANTISENSE OLIGOMERS

| Organism | GenBank Reference | Native sequence | Antisense oligomer |
|---|---|---|---|
| N. gonorrhoea | X07714 nt 834–854 | TTGGGCAACTTGA TTGCTTGG | CCAAGCAATCAAGTTGCCCAA (SEQ ID NO: 51) |
| Staph. aureus | Y15856 nt 1–21 | CTGGCTCAGGATG AACGCTGG | CCAGCGTTCATCCTGAGCCAG (SEQ ID NO: 52) |
| Bartonella hens | X89208 nt 3–23 | | |
| Staph. aureus | Y15856 nt 163–183 | ATATTTTGAACCG CATGGTTC | GAACCATGCGGTTCAAAATAT (SEQ ID NO: 53) |
| Staph. aureus | Y15856 nt 640–660 | CTTGAGTGCAGAA GAGGAAAG | CTTTCCTCTTCTGCACTCAAG (SEQ ID NO: 54) |
| Staph. aureus | Y15857 nt 447–466 | | ATGTGCACAGTTACTTACAC avi ref no. 23 |
| Staph. aureus | Y15857 nt 1272–1291 | | CTGAGAACAACTTTATGGGA avi ref no. 24 |
| Staph. aureus | Y15856 nt 819–839 | GTGTTAGGGGGTT TCCGCCCC | GGGGCGGAAACCCCCTAACAC (SEQ ID NO: 55) |
| Myco. tubercul. | X52917 nt 1–21 | GGCGGCGTGCTTA ACACATGC | GCATGTGTTAAGCACGCCGCC (SEQ ID NO: 56) |
| Myco. tubercul. | X52917 nt 138–158 | GGACCACGGGATG CATGTCTT | AAGACATGCATCCCGTGGTCC (SEQ ID NO: 57) |
| Myco. tubercul. | X52917 nt 604–624 | AGAGTACTGCAGG GGAGACTG | CAGTCTCCCCTGCAGTACTCT (SEQ ID NO: 58) |
| Myco. tubercul. | X52917 nt 784–804 | TGGGTTTCCT-TCCT TGGGATC | GATCCCAAGGAAGGAAACCCA (SEQ ID NO: 59) |
| H. pylori | M88157 nt 1–21 | TTTATGGAGAGTT TGATCCTG | CAGGATCAAACTCTCCATAAA (SEQ ID NO: 60) |
| H. pylori | M88157 nt 181–201 | ACTCCTACGGGGG AAAGATTT | AAATCTTTCCCCCGTAGGAGT (SEQ ID NO: 61) |
| H. pylori | M88157 nt 613–633 | AGAGTGTGGGAGA GGTAGGTG | CACCTACCTCTCCCACACTCT (SEQ ID NO: 62) |
| H. pylori | M88157 nt 794–814 | TTGGAGGGCTTAG TCTCTCCA | TGGAGAGACTAAGCCCTCCAA (SEQ ID NO: 63) |
| Strep. pneumoniae | AF003930 nt 1–21 | ATTTGATCCTGGC TCAGGACG | CGTCCTGAGCCAGGATCAAAT (SEQ ID NO: 64) |
| Strep. pneumoniae | AF003930 169–189 | AGAGTGGATGTTG CATGACAT | ATGTCATGCAACATCCACTCT (SEQ ID NO: 65) |

TABLE 2B-continued

BACTERIAL 16s rRNA SEQUENCES AND ANTISENSE OLIGOMERS

| Organism | GenBank Reference | Native sequence | Antisense oligomer |
|---|---|---|---|
| Strep. pneumoniae | AF003930 | | TTGAGTGCAAGAG ACTCTCCCCTCTTGCACTCAA |
| | 646–666 | GGGAGAGT | (SEQ ID NO: 66) |
| Strep. pneumoniae | AF003930 | | GTTAGACCCTTTC AAACCCCGGAAAGGGTCTAAC |
| | 826–846 | CGGGGTTT | (SEQ ID NO: 67) |
| Treponema pallad. | AJ010951 | | AGAGTTTGATCAT TCTGAGCCATGATCAAACTCT |
| | nt 1–21 | GGCTCAGA | (SEQ ID NO: 68) |
| S. thyphi. | U88545 | | |
| | nt 8–28 | | |
| H. influenza | M35019 | | |
| | nt 8–28 | | |
| Treponema pallad. | AJ010951 | | ACTCAGTGCTTCA ACCCCTTATGAAGCACTGAGT |
| | nt 173–193 | TAAGGGGT | (SEQ ID NO: 69) |
| Treponema pallad. | AJ010951 | | TTGAATTACGGAA AGTTTCCCTTCCGTAATTCAA |
| | nt 651–671 | GGGAAACT | (SEQ ID NO: 70) |
| Treponema pallad. | AJ010951 | | GTTGGGGCAAGAG CACTGAAGCTCTTGCCCCAAC |
| | nt 831–851 | CTTCAGTG | (SEQ ID NO: 71) |

2 Approximate nucleotide locations

Exemplary oligomers antisense to *Chlamydia trachomatis* 16S rRNA (SEQ ID NO:72, SEQ ID NO:73, SEQ ID NO:74 and SEQ ID NO:75) were designed based on the sequence found at GenBank Accession No. D85722. These are shown in Table 2C, below.

Exemplary oligomers antisense to *Bartonella henselae* 16S rRNA (SEQ ID NO:76, SEQ ID NO:77, SEQ ID NO:78 and SEQ ID NO:79) were designed based on the sequence found at GenBank Accession No. X89208.

Exemplary oligomers antisense to *Hemophilis influenza* 16S rRNA (SEQ ID NO: 81, SEQ ID NO: 82 and SEQ ID NO: 83) were designed based on the sequence found at GenBank Accession No. M35019. A further exemplary oligomer, antisense to a *H. influenza* 16S rRNA sequence and a *Salmonella thyphimurium* 16S rRNA sequence (SEQ ID NO: 80), is provided in Table 2C, below.

An exemplary oligomer antisense to *Shigella dysenterae* 16S rRNA (SEQ ID NO:88) was designed based on the sequence found at GenBank Accession No. X96966. Further exemplary antisense oligomers antisense to *Shigella dys* 16S rRNA and one or more other bacterial 16S rRNA sequences are provided in Table 2C.

TABLE 2C

BACTERIAL 16s rRNA SEQUENCES AND ANTISENSE OLIGOMERS

| Organism | GenBank Reference | Native sequence | Antisense oligomer |
|---|---|---|---|
| Chlamydia trach. | D85722 | | CTGAGAATTTGA GAACCAAGATCAAATTCTCAG |
| | nt 1–21 | TCTTGGTTC | (SEQ ID NO: 72) |
| Chlamydia trach. | D85722 | | ATATTTGGGCATC GTTACTCGGATGCCCAAATAT |
| | nt 176–196 | CGAGTAAC | (SEQ ID NO: 73) |
| Chlamydia trach. | D85722 | | AGAGGGTAGATG CCTTTTCTCCATCTACCCTCT |
| | nt 658–678 | GAGAAAAGG | (SEQ ID NO: 74) |

TABLE 2C-continued

BACTERIAL 16s rRNA SEQUENCES AND ANTISENSE OLIGOMERS

| Organism | GenBank Reference | Native sequence | Antisense oligomer |
|---|---|---|---|
| Chlamydia trach. | D85722 nt 838-858 | TGGATGGTCTCA ACCCCATCC | GGATGGGGTTGAGACCATCCA (SEQ ID NO: 75) |
| Bartonella hens. | X89208 nt 1-21 | TCCTGGCTCAGG ATGAACGCT | AGCGTTCATCCTGAGCCAGGA (SEQ ID NO: 76) |
| Bartonella hens. | X89208 nt 149-169 | CGTCCTACTGGA GAAAGATTT | AAATCTTTCTCCAGTAGGACG (SEQ ID NO: 77) |
| Bartonella hens. | X89208 nt 581-601 | TGAGTATGGAAG AGGTGAGTG | CACTCACCTCTTCCATACTCA (SEQ ID NO: 78) |
| Bartonella hens. | X89208 nt 761-781 | TTGGGTGGTTTAC TGCTCAGT | ACTGAGCAGTAAACCACCCAA (SEQ ID NO: 79) |
| H. influenza | M35019 nt 2-21 | AATTGAAGAGTT TGATCATG | CATGATCAAACTCTTCAATTN (SEQ ID NO: 80) |
| S. thyphi. | U88545 nt 2-21 | | |
| H. influenza | M35019 nt 180-200 | TATTATCGGAAG ATGAAAGTG | CACTTTCATCTTCCGATAATA (SEQ ID NO: 81) |
| H. influenza | M35019 nt 649-669 | AACTAGAGTACT TTAGGGAGG | CCTCCCTAAAGTACTCTAGTT (SEQ ID NO: 82) |
| H. influenza | M35019 nt 829-849 | GGGGGTTGGGGT TTAACTCTG | CAGAGTTAAACCCCAACCCCC (SEQ ID NO: 83) |
| Shigella dys. | X96966 nt 1-21 | TGGCTCAGATTG AACGCTGGC | GCCAGCGTTCAATCTGAGCCA (SEQ ID NO: 84) |
| E. coli | X80725 nt 11-31 | | |
| S. thyphi. | X96966 nt 20-40 | | |
| N. gonorrhoea | X07714 nt 21-41 | | |
| H. influenza | M35019 nt 20-40 | | |
| Shigella dys. | X96966 nt 162-182 | ACGTCGCAAGAC CAAAGAGGG | CCCTCTTTGGTCTTGCGACGT (SEQ ID NO: 85) |
| S. thyphi. | X96966 nt 181-201 | | |
| Shigella dys. | X96966 nt 633-653 | TGAGTCTCGTAG AGGGGGGTA | TACCCCCCTCTACGAGACTCA (SEQ ID NO: 86) |

TABLE 2C-continued

BACTERIAL 16s rRNA SEQUENCES AND ANTISENSE OLIGOMERS

| Organism | GenBank Reference | Native sequence | Antisense oligomer |
|---|---|---|---|
| E. coli | X80725 | | |
| | nt 644-664 | | |
| S. thyphi. | X96966 | | |
| | nt 652-672 | | |
| Shigella dys. | X96966 | GTTGTGCCCTTGA | GCCACGCCTCAAGGGCACAAC |
| | nt 813-833 | GGCGTGGC | (SEQ ID NO: 87) |
| E. coli | X80725 | | |
| | nt 824-844 | | |
| S. thyphi. | X96966 | | |
| | nt 832-852 | | |
| Shigella dys. | X96966 | GAACCTTGTAGA | CCTCGTATCTCTACAAGGTTC |
| | nt 983-1003 | GATACGAGG | (SEQ ID NO: 88) |

3 Approximate nucleotide locations

Exemplary Gram-positive bacterial targets include, but are not limited to, *Staphylococcus aureus, Mycobacterium tuberculosis* and *Streptococcus pneumoniae*.

Exemplary oligomer sequences antisense to Gram-positive bacterial 16S rRNA sequences are exemplified in Table 3 by the sequences presented as SEQ ID NO:27 and SEQ ID NO:28, with the bacterial 16s rRNAs to which the exemplary antisense oligomers are targeted indicated in Table 3 as "+" and those which are not targeted indicated as "–".

TABLE 3

GRAM POSITIVE 16s rRNA SEQUENCES AND ANTISENSE OLIGOMERS

| Organism | SEQUENCE ANTISENSE | AACTACGTGCCAGC AGCCGCG CGCGGCTGCTGGCA CGTAGTT | TCGTGAGATGTTGG GTTAAGT ACTTAACCCAACATC TCACGA |
|---|---|---|---|
| Staph aureus | Y15856 | + | + |
| Myco. tubercul. | X52917 | + | + |
| Strep. pneumoniae | AF003930 | + | + |
| E. coli | X80725 | – | – |
| S. thyphi | U88545 | – | – |
| P. aeruginosa | AF170358 | – | + |
| Vibrio cholera | AF118021 | – | – |
| N. gonorrhoea | X07714 | + | + |
| H. pylori | M88157 | – | + |

TABLE 3-continued

GRAM POSITIVE 16s rRNA SEQUENCES AND ANTISENSE OLIGOMERS

| Organism | SEQUENCE ANTISENSE | AACTACGTGCCAGC AGCCGCG CGCGGCTGCTGGCA CGTAGTT | TCGTGAGATGTTGG GTTAAGT ACTTAACCCAACATC TCACGA |
|---|---|---|---|
| Treponema pallad. | AJ010951 | – | – |
| Chlamydia trach. | D85722 | – | – |
| Bartonella hens | X89208 | – | + |
| H. influenza | M35019 | – | – |
| Shigella dys. | X96966 | – | – |

4 Based on nucleotides 497-517 of GenBank Y15856, designated SEQ ID NO: 27
5 Based on nucleotides 1064-1084 of GenBank Y15856, designated SEQ ID NO: 28

Exemplary Gram-negative bacterial targets include, but are not limited to, *E. coli, Salmonella thyphimurium, Pseudomonas aeruginosa, Vibrio cholera, Neisseria gonorrhoea, Helicobacter pylori, Bartonella henselae, Hemophilis Influenza* and *Shigella dysenterae*.

Exemplary oligomer sequences antisense to Gram-negative bacterial 16S rRNA sequences are exemplified in Table 4 by the sequences presented as SEQ ID NO:29 and SEQ ID NO:30, with the bacterial 16s rRNAs to which the exemplary antisense oligomers are targeted indicated in Table 4 as "+" and those which are not targeted indicated as "–".

TABLE 4

GRAM NEGATIVE 16s rRNA SEQUENCES AND ANTISENSE OLIGOMERS

| Organism | SEQUENCE<br>ANTISENSE | TCGGAATTACTGGGC<br>GTAAA<br>TTTACGCCCAGTAATT<br>CCGA | CCGCCCGTCACACCAT<br>GGGAGT<br>ACTCCCATGGTGTGACG<br>GGCGG |
|---|---|---|---|
| E. coli | X80725 | + | + |
| S. thyphi | U88545 | + | + |
| P. aeruginosa | AF170358 | + | + |
| Vibrio cholera | AF118021 | + | + |
| N. gonorrhoea | X07714 | + | + |
| Staph aureus | Y15856 | − | − |
| Myco. tubercul. | X52917 | − | − |
| H. pylori | M88157 | − | + |
| Strep. pneumoniae | AF003930 | − | − |
| Treponema pallad. | AJ010951 | − | + |
| Chlamydia trach. | D85722 | − | + |
| Bartonella hens | X89208 | − | + |
| H. influenza | M35019 | − | + |
| Shigella dys. | X96966 | + | + |

6 Based on nucleotides 546–566 of GenBank X80725, designated SEQ ID NO: 29
7 Based on nucleotides 1389–1409 of GenBank X80725, designated SEQ ID NO: 30

Exemplary bacterial targets for broad spectrum antisense oligomers include, but are not limited to, E. coli, Salmonella thyphimurium, Pseudomonas aeruginosa, Vibrio cholera, Neisseria gonorrhoea, Helicobacter pylori, Bartonella henselae, Hemophilis Influenza, Shigella dysenterae, Staphylococcus aureus, Mycobacterium tuberculosis, Streptococcus pneumoniae, Treponema palladium and Chlamydia trachomatis. (See Table 1.)

Exemplary broad spectrum antisense oligomers are presented in Tables 5A and 5B as SEQ ID NOs:21-25, with the bacterial 16s rRNAs to which the exemplary antisense oligomers are targeted indicated in Tables 5A and 5B as "+" and those which are not targeted indicated as "−".

TABLE 5A

BROAD SPECTRUM ANTISENSE OLIGONUCLEOTIDE SEQUENCES

| Organism | SEQUENCE<br>ANTISENSE | AGACTCCTACGG<br>GAGGCAGCA<br>TGCTGCCTCCCGT<br>AGGAGTCT | CGTGCCAGCAGC<br>CGCGGTAAT<br>ATTACCGCGGCT<br>GCTGGCACG | AACAGGATTAG<br>ATACCCTGGT<br>ACCAGGGTATC<br>TAATCCTGTT |
|---|---|---|---|---|
| E. coli | X80725 | + | + | + |
| S. thyphi | U88545 | + | + | + |
| P. aeruginosa | AF170358 | + | + | + |
| Vibrio cholera | AF118021 | + | + | + |
| N. gonorrhoea | X07714 | + | + | + |
| Staph. aureus | Y15856 | + | + | + |
| Myco. tubercul. | X52917 | + | + | + |

TABLE 5A-continued

BROAD SPECTRUM ANTISENSE OLIGONUCLEOTIDE SEQUENCES

| Organism | SEQUENCE ANTISENSE | AGACTCCTACGG GAGGCAGCA TGCTGCCTCCCGT AGGAGTCT | CGTGCCAGCAGC CGCGGTAAT ATTACCGCGGCT GCTGGCACG | AACAGGATTAG ATACCCTGGT ACCAGGGTATC TAATCCTGTT |
|---|---|---|---|---|
| H. pylori | M88157 | + | + | + |
| Strep. pneumoniae | AF003930 | + | + | + |
| Treponema pallad. | AJ010951 | + | + | + |
| Chlamydia trach. | D85722 | + | + | + |
| Bartonella hens | X89208 | + | + | + |
| H. influenza | M35019 | + | + | + |
| Shigella dys. | X96966 | + | + | + |

8: based on nucleotides 327–347 of GenBank No. X80725, designated SEQ ID NO: 21
9: based on nucleotides 504–524 of GenBank No. X80725, designated SEQ ID NO: 22
10: based on nucleotides 781–801 of GenBank No. X80725, designated SEQ ID NO: 23

TABLE 5B

BROAD SPECTRUM ANTISENSE OLIGONUCLEOTIDE SEQUENCES

| Organism | SEQUENCE ANTISENSE | GCACAAGCGGTGGA GCATGTG CACATGCTCCACCG CTTGTGC | ATGTTGGGTTAAGT CCCGCAA TTGCGGGACTTAAC CCAACAT |
|---|---|---|---|
| E. coli | X80725 | + | |
| S. thyphi | U88545 | + | + |
| P. aeruginosa | AF170358 | + | − |
| Vibrio cholera | AF118021 | + | + |
| N. gonorrhoea | X07714 | − | + |
| Staph aureus | Y15856 | + | + |
| Myco. tubercul. | X52917 | − | + |
| H. pylori | M88157 | − | + |
| Strep. pneumoniae | AF003930 | + | + |
| Treponema pallad. | AJ010951 | + | − |
| Chlamydia trach. | D85722 | − | − |
| Bartonella hens | X89208 | + | + |
| H. influenza | M35019 | + | + |
| Shigella dys. | X96966 | + | + |

11: based on nucleotides 924–944 of GenBank No. X80725, designated SEQ ID NO: 24
12: based on nucleotides 1072–1092 of GenBank No. X80725, designated SEQ ID NO: 25.

VI. Inhibitory Activity of Antisense Oligomers

A. Effect of Antisense Oligomers to Bacterial 16S rRNA on Bacterial Growth

The effect of PMO antisense oligomers on bacterial culture viability was tested using the protocol described below; see "Bacterial Cultures" in Materials and Methods. Briefly, test oligonucleotides, diluted in phosphate buffered saline (PBS), are added to the freshly inoculated bacterial cultures; the cultures are incubated at 37° C. overnight, e.g., 6 to 26 hours, diluted, and plated on agar plates; colonies are counted 16-24 hours later. Non-selective bacterial growth media, e.g., agar containing nutrients appropriate to the type of bacteria being cultured, are utilized, as generally known in the art.

The viability of bacteria following overnight culture with a test oligomer is based on the number of bacterial colonies in antisense oligomer-treated cultures relative to untreated or nonsense treated cultures. An exemplary nonsense control is an oligomer antisense to c-myc, having the sequence presented as SEQ ID NO: 139.

A1. Inhibition of *Salmonella thyphimurium* with a Conserved-Sequence Oligomer Antisense to 16S rRNA. Two strains of *Salmonella thyphimurium* (1535 and 1538) were inoculated into broth media, as described in Materials and Methods, below. An oligomer antisense to a 16S rRNA sequence conserved amongst *E. coli, S. thyphimurium* and *S. dysenterae* ("BS-1"; SEQ ID NO:15) was added to a final concentration of 1 µM and the tube placed in an incubator at 37° C. for 6 to 16 hours. At the end of the incubation, the broth was spread onto plates, incubated overnight for 16 to 24 hours and colonies counted. The data, shown in Table 6, provides evidence that *Salmonella thyphimurium* is inhibited by a 16S rRNA antisense oligomer based on a 16S rRNA sequence which is conserved amongst *E. coli, S. thyphimurium* and *S. dysenterae*.

TABLE 6

Effect of Broad Spectrum Antisense on *Salmonella thyphimurium*

| Strain (culture time) | Control (colonies) | 1 µM AS to 16S rRNA (colonies) | % Inhibition |
|---|---|---|---|
| 1535 (6 hours) | 217 | 141 | 35 |
| 1535 (16 hours) | 214 | 52 | 76 |

TABLE 6-continued

Effect of Broad Spectrum Antisense on *Salmonella thyphimurium*

| Strain (culture time) | Control (colonies) | 1 µM AS to 16S rRNA (colonies) | % Inhibition |
|---|---|---|---|
| 1538 (6 hours) | 824 | 664 | 19 |
| 1538 (16 hours) | 670 | 133 | 80 |

A2. Effect of Antisense Oligomers to Bacterial 16S rRNA on Growth Of *E. coli*.

The effect of PMO antisense oligomers on inhibition of *E. coli* was evaluated, using a procedure such as described above, by adding an antisense oligomer targeting particular 20-22 nucleotide portions of the *E. coli* 16S rRNA sequence found at GenBank Accession No. X80725 to individual *E. coli* cultures. Each antisense oligomer was incubated at a 1 µM concentration with *E. coli* bacteria for 16 hours, the cultures were diluted and plated on agar plates, and colonies were counted 16-24 hours later. The results, shown in Table 7, indicate that PMO antisense oligomers targeting *E. coli* 16S rRNA inhibited growth of colonies by up to 60%, with oligomers targeting various regions throughout the 16S rRNA sequence observed to be effective.

TABLE 7

*E. coli* 16s rRNA Targeting Study

| AVI Ref. No. | Location | Antisense sequence (5'→3') | SEQ ID NO. | Percent Inhibition | S.E. | Repeats (n) |
|---|---|---|---|---|---|---|
| 9 | 1263–1283 | GCA CTT TAT GAG GTC CGC TTG | 19 | 59.8 | 3.4 | 8 |
| 15 | 1272–1293 | GGA CTA CGA CGC ACT TTA TGA G | 15 | 19.5 | 7.4 | 9 |
| 16 | 1252–1272 | GGT CCG CTT GCT CTC GCG AGG | 16 | 21.5 | 11 | 9 |
| 17 | 446–466 | GCA AAG GTA TTA ACT TTA CTC | 17 | 66 | 3.3 | 14 |
| 27 | 1–20 | ATC TGA GCC ATG ATC AAA CT | 97 | 55.2 | 9.7 | 5 |
| 28 | 301–320 | TGT CTC AGT TCC AGT GTT GC | 98 | 35 | 7.2 | 8 |
| 29 | 722–741 | GTC TTC GTC CAG GGG GCC GC | 99 | 52.5 | 4 | 7 |
| 30 | 1021–1040 | CAC CTG TCT CAC GGT TCC CG | 100 | 56 | 8.4 | 5 |
| 31 | 1431–1450 | CGC CCT CCC GAA GTT AAG CT | 101 | 43 | 13 | 5 |

Figure 5:
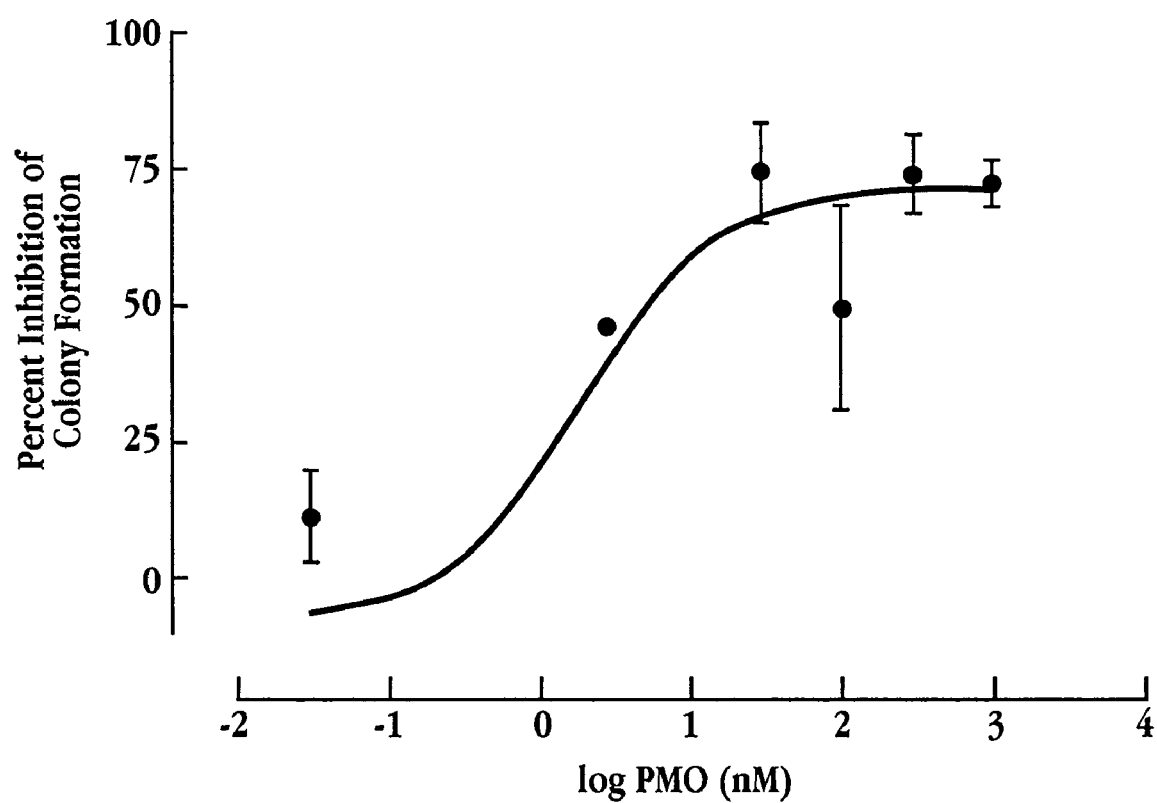
FIG. 5 depicts the results of a study on the effect of various concentrations of a PMO having SEQ ID NO: 15 (broad spectrum; see Table 2A), targeted against a bacterial 16S rRNA consensus sequence, on the bacterial colony formation in *E. coli*, presented as percent inhibition of colony formation.

FIG. 5 depicts the results of a study on the effect of various concentrations of the PMO having SEQ ID NO: 15 (broad spectrum) targeted against a bacterial 16S rRNA consensus sequence on the bacterial colony formation in *E. coli*, presented as percent inhibition of colony formation. As the figure shows, about 70% inhibition was achieved at about 0.1 μM PMO.

A3. Inhibition of *Staphylococcus aureus* and *Pseudomonas aeruginosa* with Oligomers Antisense to 16S rRNA.

Table 8 and 9 show the effect of oligomers targeting 16S rRNA, at a concentration of 1 μM, on bacterial growth in *Staphylococcus aureus* and *Pseudomonas aeruginosa*. In a typical experiment, antisense oligomers targeting particular 22-nucleotide portions of the *Staphylococcus aureus* and *Pseudomonas aeruginosa* 16S rRNA sequences, found at GenBank Accession Nos. Y15857 and Z76651, respectively, were incubated with the respective bacteria at a concentration of 1 μM for 16 hours. Growth of *S. aureus* was inhibited by up to 25%, and growth of *P. aeruginosa* was inhibited by up to about 53%.

TABLE 8

*Staphylococcus aureus* 16s rRNA Targeting Study

| AVI Ref. No. | Location | Antisense sequence (5'→3') | SEQ ID NO | Percent Inhibition | S.E. | n = |
|---|---|---|---|---|---|---|
| 23 | 447–466 | ATG TGC ACA GTT ACT TAC AC | 93 | 2.5 | 8.6 | 2 |
| 24 | 1272–1291 | CTG AGA ACA ACT TTA TGG GA | 94 | 25.3 | 11 | 2 |

TABLE 9

*Pseudomonas aeruginosa* 16s rRNA Targeting Study

| AVI Ref. No. | Location | Antisense sequence (5'→3') | SEQ ID NO | Percent Inhibition | S.E. | n = |
|---|---|---|---|---|---|---|
| 25 | 447–466 | TTA TTC TGT TGG TAA CGT CA | 95 | 37.3 | 9.8 | 3 |
| 26 | 1272–1291 | CG AGT TGC AGA CTG CGA TC | 96 | 52.7 | 7.1 | 3 |

Inhibition of *Listeria* was also demonstrated by a corresponding anti-16S PMO. A very low dose (about 30 nM) of the PMO gave about 40% inhibition.

A4. Effect of Antisense Oligomers to Bacterial rRNA on Growth Of Vancomycin-Resistant *Enterococcus feacium* (VRE)

(a) Bacterial 16S rRNA Targets

The effect of PMO antisense oligomers on the growth of VRE was evaluated, using the method described above, by adding antisense PMO's targeting numerous 16S rRNA sequences to cultures of VRE and incubating at a concentration of 1 μM for 16 hours. The results shown in Table 10 and in FIG. 6 indicate that inhibition ranged from about 48% to about 70%, averaging about 60%, with no significant differences in effectiveness seen among the oligomers tested. (The nucleotide symbol "M" in the sequences represents methyl cytidine.)

Figure 6:
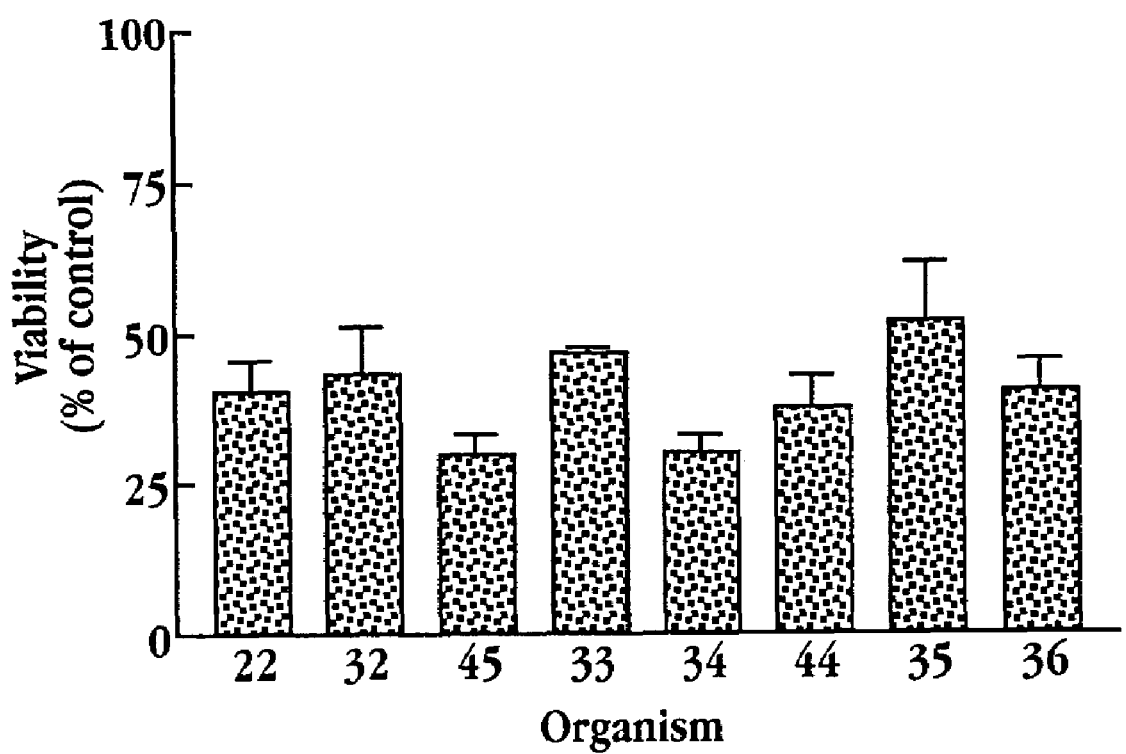
FIG. 6 depicts the results of a study wherein PMO oligomers targeting various different regions of *Enterococcus faecium* 16S rRNA, designated AVI-1-23-22, -32, -45, -33, -34, -44, -35 and -36 (SEQ ID NOs: 92, 102, 115, 103, 104, 114, 105, and 106), indicated in the figure as 22, 23, 45, 33, 34, 44, 35 and 36, respectively, were added at 1 µM to vancomycin-resistant *Enterococcus faecium* (VRE) cultures, with the results presented as percent viability.

FIG. 6 illustrates the effect of a broad spectrum PMO on VRE colony formation. The oligomer designated SEQ ID NO: 114 is considered broad spectrum, targeted to a region conserved in all of the bacteria listed in Table 5A, above. This oligomer targets approximately the same region as that targeted by SEQ ID NO: 23, which is shown in Table 5A. As can be seen from the data in Table 10, this oligomer was similar in effectiveness to a "narrow spectrum" oligomer specific to *Enterococcus*, SEQ ID NO: 115.

Also included were several oligomers specific to 16s rRNA of other organisms (*E. coli*, *S. aureus*, and *P. aeruginosa*). These oligomers had no inhibitory effect on VRE.

TABLE 10

Targeting Study in *Enterococcus faecium*.

| PMO Source | GenBank ACC. No. | Location | Antisense Sequence (5'→3') | SEQ ID | Percent Inhibition | S.E. | n = |
|---|---|---|---|---|---|---|---|
| VRE | Y18294 | 447–466 | GAT GAA CAG TTA CTC TCA TG | 91 | 61.7 | 2.7 | 3 |
| VRE | Y18294 | 1272–1291 | ACT GAG AGA AGC TTT AAG AG | 92 | 59.7 | 5.1 | 6 |
| VRE | Y18294 | 1–20 | GGC ACG CCG CCA GCG TTC G | 102 | 56.7 | 7.8 | 3 |
| VRE | Y18294 | 300–319 | TGT CTC AGT CCC AAT GTG GC | 103 | 53.7 | 1.0 | 3 |
| VRE | Y18294 | 721–740 | GTT ACA GAC CAG AGA GCC GC | 104 | 69.7 | 3.0 | 3 |
| VRE | Y18294 | 1022–1041 | CAC CTG TCA CTT TGC CCC CG | 105 | 47.9 | 10.1 | 3 |
| VRE | Y18294 | 1438–1456 | GGC GGC TGG CTC CAA AAG G | 106 | 58.5 | 3.2 | 3 |
| VRE | Y18294 | 776–795 | GAC TAC CAG GGT ATC TAA TC | 114 | 62.2 | 5.5 | 3 |
| VRE | Y18294 | 194–213 | CAG CGA CAC CCG AAA GCC CC | 115 | 70.1 | 3.3 | 3 |

TABLE 10-continued

Targeting Study in *Enterococcus faecium*.

| PMO Source | GenBank ACC. No. | Location | Antisense Sequence (5'→3') | SEQ ID | Percent Inhibition | S.E. | n = |
|---|---|---|---|---|---|---|---|
| *S. aureus* | | See Table 8 | CTG AGA ACA ACT TTA TGG GA | 94 | 24 | 8.8 | 3 |
| *P. aeruginosa* | | See Table 9 | TCG AGT TGC AGA CTG CGA TC | 96 | 26 | 11.6 | 3 |
| *E. coli* | | See Table 7 | GCA AAG GTA TTA ACT TTA CTC | 17 | 17 | 22.4 | 3 |
| *E. coli* | | See Table 7 | GCA CTT TAT GAG GTC CGC TTG | 19 | 9 | 10 | 3 |
| VRE | Y18294 | 0077–95 | CAC CCG TTC GCC ACT CCT C | 107 | 45.1 | 6.1 | 3 |
| VRE | Y18294 | 0895–914 | TCA ATT CCT TTG AGT TTC AA | 108 | 31.8 | 15.3 | 3 |
| VRE | Y18294 | 1263–1291 | GCA ATC CGC ACT GAG AGA AGG TTT AAG AG | 109 | 39.1 | 11.4 | 6 |
| VRE | Y18294 | 1268–1291 | C CGC ACT GAG AGA AGC TTT AAG AG | 110 | 50.1 | 5.5 | 6 |
| VRE | Y18294 | 1275–1291 | GAG AGA AGC TTT AAG AG | 111 | 61.5 | 3.3 | 6 |
| VRE | Y18294 | 1277–1291 | G AGA AGC TTT AAG AG | 112 | 46.3 | 5 | 6 |
| VRE | Y18294 | 1282–1291 | A AGC TTT AAG AG | 113 | 39.5 | 8.2 | 6 |
| VRE | Y18294 | 1274–1291 | T GAG AGA AGC TTT AAG AG | 121 | 57.2 | 4.8 | 3 |
| VRE | Y18294 | 1273–1291 | CT GAG AGA AGC TTT AAG AG | 122 | 54.4 | 2.7 | 3 |
| VRE | Y18294 | 196–213 | GCG ACA CCC GAA AGC GCC | 123 | 59.0 | 5.3 | 6 |
| VRE | Y18294 | 723–740 | TAC AGA CCA GAG AGC CGC | 124 | 63.3 | 4.9 | 9 |
| VRE | Y18294 | 197–213 | CGA CAC CCG AAA GCG CC | 125 | 63.6 | 3.7 | 9 |
| VRE | Y18294 | 195–213 | A GCG ACA CCC GAA AGC GCC | 126 | 60.6 | 4.8 | 12 |
| VRE | Y18294 | 196–213 | CG ACA CCC GAA AGC GCC A | 127 | 58.9 | 5.6 | 9 |
| VRE | Y18294 | 197–213 | MG AMA MMM GAA AGM GMM | 128 | 60.3 | 4.5 | 9 |
| VRE | Y18294 | 723–740 | TAM AGA MMA GAG AGM MGM | 129 | 56.9 | 3.9 | 9 |
| VRE | Y18294 | 1162–1177 | MMM MAM MTT MTT MMG G | 130 | 56.1 | 3.7 | 9 |
| VRE | Y18294 | 1345–1363 | CAC CGC GGC GTG CTG ATC C | 131 | 64.0 | 3.9 | 6 |
| VRE | Y18294 | 1162–1177 | CCC CAC CTT CCT CCG G | 132 | 70.2 | 1.6 | 3 |
| VRE | Y18294 | 916–933 | CCG CTT GTG CGG GCC CCC | 133 | 66.8 | 4.3 | 3 |
| VRE | Y18294 | 1345–1362 | CAC CGC GGC GTG GTG ATC | 134 | 71.4 | 11.3 | 3 |
| VRE | Y18294 | 1345–1361 | CAC CGC GGC GTG CTG AT | 135 | 57.3 | 3.8 | 3 |
| VRE | Y18294 | 1346–1364 | ACC GCG GCG TGC TGA TCC | 136 | 75.0 | 4.4 | 3 |
| VRE | Y18294 | 1344–1360 | CCG CGG CGT GCT GAT CC | 137 | 66.3 | 3.5 | 3 |
| VRE | Y18294 | 1346–1363 | ACC GCG GCG TGC TGA TC | 138 | 63.8 | 2.2 | 3 |

M represents methyl cytidine.

A dose-response study was also conducted using different concentrations of the oligomer having SEQ ID NO: 92. About 70% inhibition was achieved at 1-10 μM, about 50% at 0.1 μM, about 20% at 0.01 μM, and about 12% at 1 nM.)

(b) Bacterial 23S rRNA Targets

Figure 7:
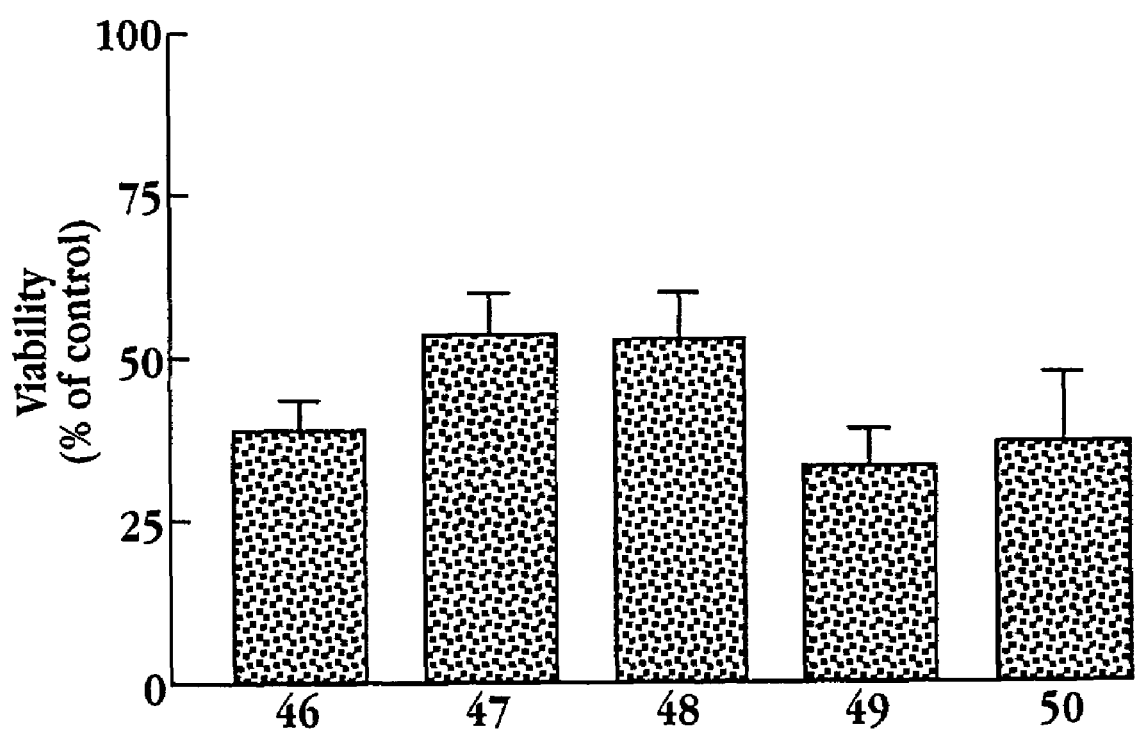
FIG. 7 depicts the results of a study wherein PMO oligomers targeting various different regions of *Enterococcus faecium* 23S rRNA, designated AVI-1-23-46, -47, -48, -49 and -50 (SEQ ID NOs: 116-120), indicated in the figure as 46, 47, 48, 49 and 50, respectively, were added at 1 µM to vancomycin-resistant *Enterococcus faecium* cultures, with the results presented as percent viability.

In a related experiment, also using vancomycin-resistant *Enterococcus feacium* (VRE) as the target bacteria, the effect of PMO antisense oligomers targeting 23S rRNA sequences on bacterial growth was evaluated, using the method described above. In individual assays, antisense PMO's targeting VRE 23S rRNA sequences were added to cultures of VRE and incubated at a concentration of 1 µM for 16 hours. The data in Table 11, below, represented graphically in FIG. 7, shows that antisense targeting of 23S rRNA in VRE was successful in inhibiting bacterial growth. Locations refer to GenBank Acc. No. X79341.

TABLE 11

VRE 23S rRNA Targeting Study

| Ref. No. | Location | Antisense Sequence (5'→3') | SEQ ID NO: | Percent Inhibition | S.E. (N = 3) |
|---|---|---|---|---|---|
| 46 | 20–39 | GTG CCA AGG CAT CCA CCG TG | 116 | 61.9 | 4.6 |
| 47 | 679–698 | CAT ACT CAA ACG CCC TAT TC | 117 | 46.8 | 6.6 |
| 48 | 1462–1480 | CCT TAG CCT CCT GCG TCC C | 118 | 47.6 | 7.5 |
| 49 | 2060–2079 | GGG GTC TTT CCG TCC TGT CG | 119 | 67.0 | 5.7 |
| 50 | 2881–2900 | CGA TCG ATT AGT ATC AGT CC | 120 | 63.0 | 10.5 |

B. Effect of Length of Antisense Oligomer on Inhibition of VRE

The procedure used to obtain the data shown in Table 10, above, was repeated using different-length versions (SEQ ID NOs: 109-113) of the anti-16S rRNA oligomer having SEQ ID NO: 92, ranging from a 12-mer (SEQ ID NO: 113) to a 29-mer (SEQ ID NO: 109). Results are given in Table 12, below.

Figure 8:
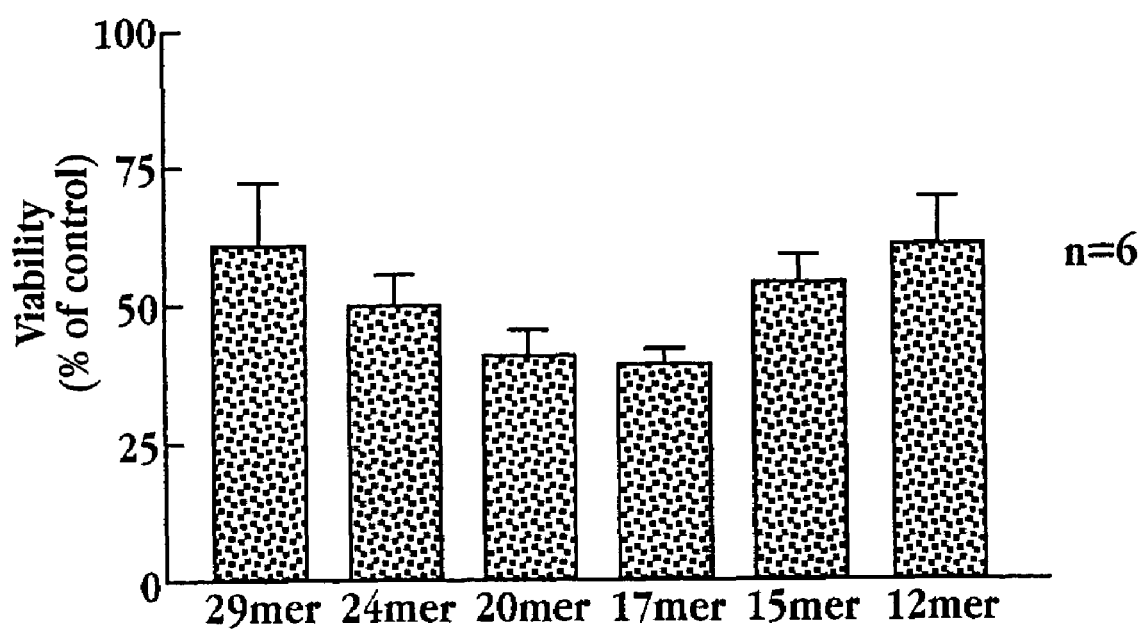
FIG. 8 depicts the results of a study on the effect of 1 µM of PMOs of various lengths targeted against the 16S rRNA of a vancomycin-resistant *Enterococcus faecium* bacterial strain on viability of the bacteria (percent viability, reported as percent of untreated control). The PMO sequences corresponding to the oligomer lengths are shown in Table 12, which illustrates antisense targeting of 16S rRNA in VRE, reported as percent inhibition (100-percent of untreated control)

As shown in Table 12 and FIG. 8, the optimum length in this study was in the 17- to 20-mer range. Further studies confirmed that oligomers with a length of from 17 to 20 nucleotide subunits, and more preferably 17-18 subunits, are generally preferred. The results suggest that shorter oligomers, such as 12-mers, may have insufficient binding affinity, and that longer oligomers, such as the 29-mer, are less easily transported into cells.

TABLE 12

Antisense Targeting of 16S rRNA in VRE

| Ref. No. | length | Antisense sequence (5'→3') | SEQ ID NO | Percent Inhibition | SE | n = |
|---|---|---|---|---|---|---|
| 39 | 29mer | GCA ATC CGC ACT GAG AGA AGC TTT AAG AG | 109 | 29.1 | 11.4 | 6 |
| 40 | 24mer | C CGC ACT GAG AGA AGC TTT AAG AG | 110 | 51.1 | 5.5 | 6 |
| 22 | 20mer | ACT GAG AGA AGC TTT AAG AG | 92 | 59.7 | 5.2 | 6 |
| 41 | 17mer | GAG AGA AGC TTT AAG AG | 111 | 61.5 | 3.3 | 6 |
| 42 | 15mer | G AGA AGC TTT AAG AG | 112 | 46.3 | 5.0 | 6 |
| 43 | 12mer | A AGC TTT AAG AG | 113 | 39.5 | 8.2 | 6 |

C. Antisense PMO Study in VRE

Figure 9:
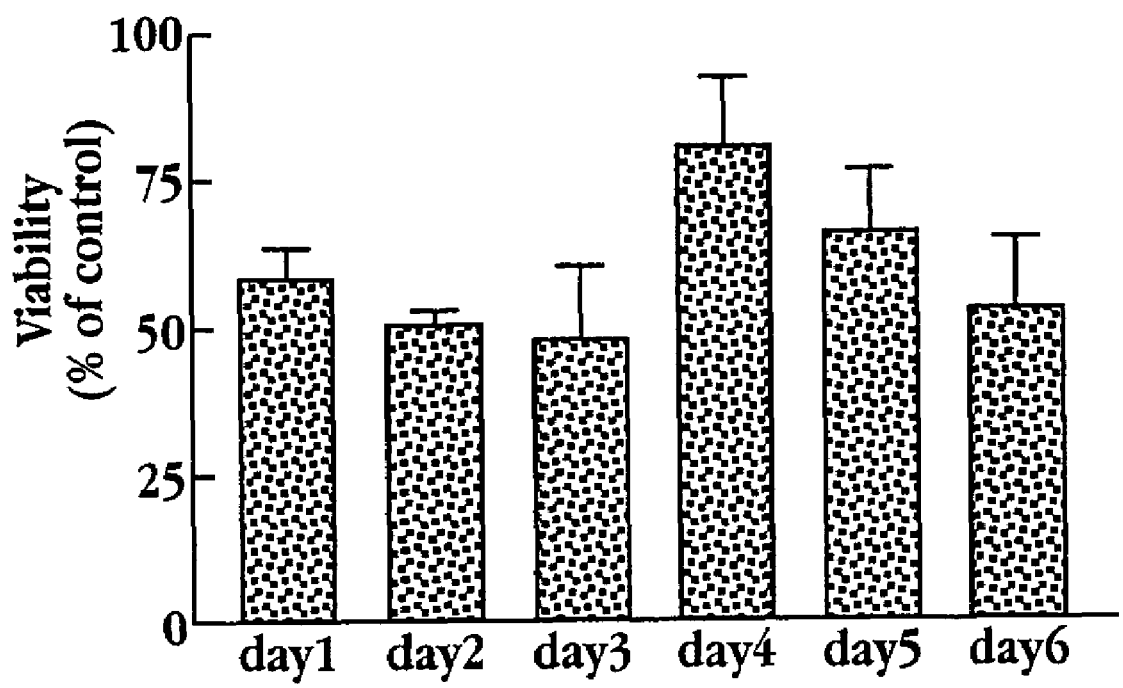
FIG. 9 depicts the results of a study on the effect of 1 µM PMO targeted against *Enterococcus faecium* 16S rRNA, designated VRE-2, AVI 1-23-22 (SEQ ID NO: 92), on bacterial colony formation in VRE, presented as percent viability (percent of control) as determined on days 1 through 6.

The 20-mer anti-16S rRNA antisense oligomer referred to above (SEQ ID NO: 92) was used in a resistance study with VRE. After each day of incubation (concn. 1 µM), three colonies were picked and retreated with oligomer to test for resistance. As shown in Table 13, below, and in FIG. 9, viability increased somewhat at four days but then dropped again at five and six days. Tests carried out to twelve days (data not shown) showed no evidence that resistance to the oligomer had developed.

TABLE 13

Resistance Study with anti-16S rRNA (SEQ ID NO: 92) in VRE

| Day | Percent Inhibition | S.E. (n = 3) |
|---|---|---|
| 1 | 41.8 | 5.2 |
| 2 | 49.6 | 2.7 |
| 3 | 51.8 | 12.3 |
| 4 | 19.2 | 11.9 |
| 5 | 34.1 | 10.9 |
| 6 | 47.2 | 12.0 |

D. Combination Therapy with Antibiotic Drugs

Figure 10A:
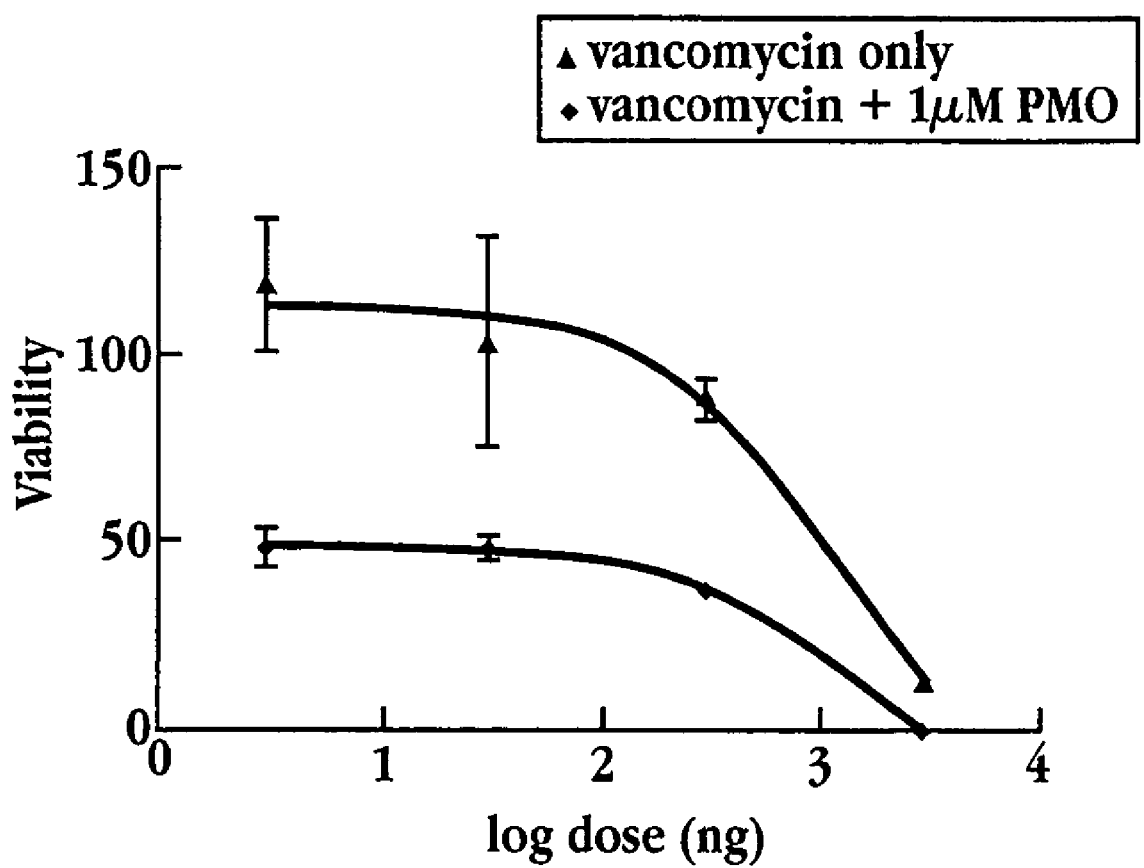
FIGS. 10A-B depict the results of a study on the effect of 1 µM of a PMO targeted against *Enterococcus faecium* 16S rRNA (SEQ ID NO: 92), alone or in combination with (A) 3 µM vancomycin, or (B) 3 µM ampicillin, on growth of VRE, with the results reported as percent viability.

*Enterococcus faecium* was treated with vancomycin alone and in combination with 1.0 µM antisense PMO targeted to VRE 16S rRNA (SEQ ID NO: 92). Inhibition was greatly increased by addition of the PMO, as shown in FIG. 10A, and the organisms were completely eliminated at 3 µM vancomycin and 1 µM PMO. The results show that use of an antisense PMO targeted to VRE 16S rRNA together with vancomycin results in an enhanced anti-bacterial effect relative that of vancomycin alone.

Figure 10B:
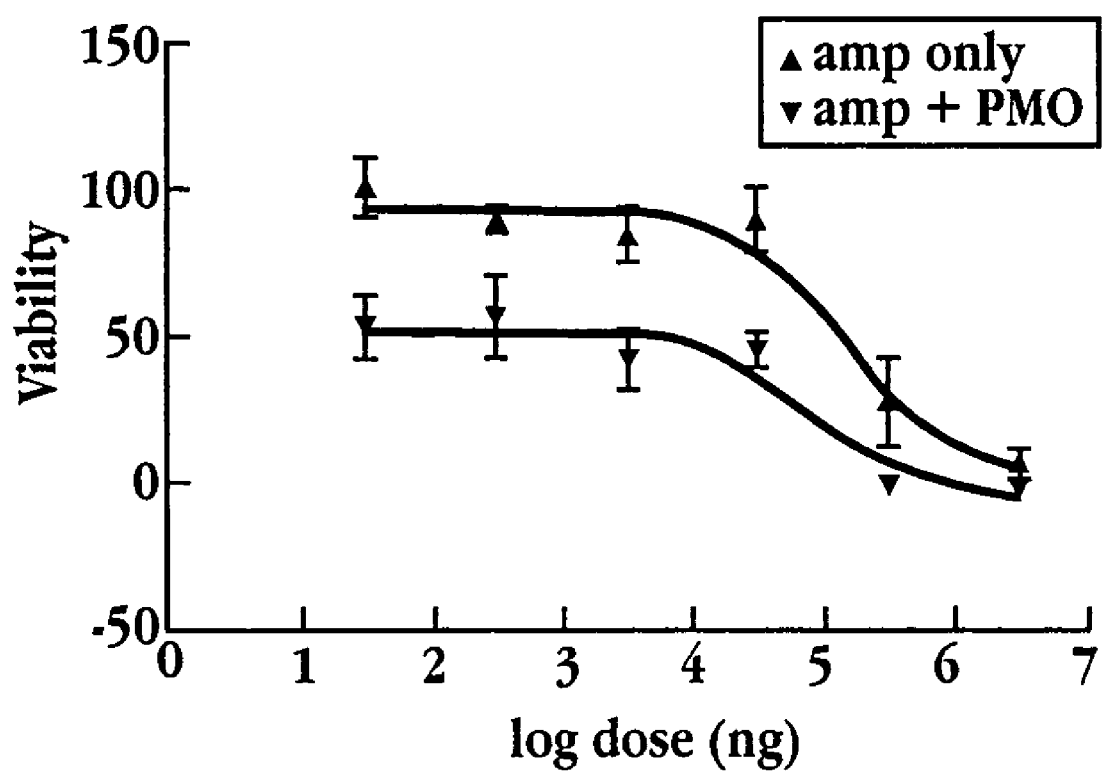

A similar study was conducted with vancomycin resistant *Enterococcus faecium* (VRE), treated with ampicillin combination with 1.0 µM of the same antisense PMO (see FIG. 10B). Again, essentially complete inhibition was achieved by the combination at 3 µM ampicillin. Similar to the results obtained for vancomycin, the combination of an antisense PMO targeted to VRE 16S rRNA and ampicillin resulted in an enhanced anti-bacterial effect.

VII. In Vivo Administration of Antisense Oligomers

In another aspect, the invention is directed to slowing or limiting bacterial infection in vivo in a mammal, and/or decreasing or eliminating detectable symptoms typically associated with infection by that particular bacteria. In general, a therapeutically effective amount of an antisense oligonucleotide-containing pharmaceutical composition is administered to a mammalian subject, in a manner effective to inhibit the activity of a 16S rRNA.

The antisense oligonucleotides of the invention and pharmaceutical compositions containing them are useful for inhibiting bacterial infection in vivo in a mammal, and for inhibiting or arresting the growth of bacteria in the host. In other words, the bacteria may be decreased in number or eliminated, with little or no detrimental effect on the normal growth or development of the host.

In some cases, the antisense oligomer will inhibit the growth of bacteria in general. In other cases, the antisense oligomer will be specific to one or more particular types of bacteria, e.g. a particular genus, species or strain.

It will be understood that the in vivo efficacy of such an antisense oligomer in a subject using the methods of the invention is dependent upon numerous factors including, but not limited to, (1) the target sequence; (2) the duration, dose and frequency of antisense administration; and (3) the general condition of the subject.

The efficacy of an in vivo administered antisense oligomer of the invention on inhibition or elimination of the growth of one or more types of bacteria may be determined by in vitro culture or microscopic examination of a biological sample (tissue, blood, etc.) taken from a subject prior to, during and subsequent to administration of the antisense oligomer. (See, for example, Pari, G. S. et al., *Antimicrob. Agents and Chemotherapy* 39 (5):1157-1161, 1995; Anderson, K P et al., *Antimicrob. Agents and Chemotherapy* 40 (9):2004-2011, 1996.)

A. Treating Subjects

Effective delivery of the antisense oligomer to the target RNA is an important aspect of the methods of the invention. In accordance with the invention, such routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment.

For example, an appropriate route for delivery of an antisense oligomer in the treatment of a bacterial infection of the skin is topical delivery, while delivery of an antisense oligomer in the treatment of a bacterial respiratory infection is by inhalation.

Additional exemplary embodiments include oral delivery of an antisense oligomer directed to bacterial 16S or 23S rRNA for treatment of a urinary tract infection or sepsis and IV delivery for treatment of sepsis.

It is appreciated that methods effective to deliver the oligomer to the site of bacterial infection or to introduce the oligonucleotide into the bloodstream are contemplated.

Transdermal delivery of antisense oligomers may be accomplished by use of a pharmaceutically acceptable carrier adapted for topical administration. One example of morpholino oligomer delivery is described in PCT patent application WO 97/40854, incorporated herein by reference.

In one aspect of the invention, an antisense oligomer directed to bacterial 16S or 23S rRNA is delivered by way of a catheter, microbubbles, a heart valve coated or impregnated with oligomer, a Hickman catheter or a coated stent.

In one preferred embodiment, the oligomer is a morpholino oligomer, contained in a pharmaceutically acceptable carrier, and delivered orally. In a further aspect of this embodiment, a morpholino antisense oligonucleotide is administered at regular intervals for a short time period, e.g., daily for two weeks or less. However, in some cases the antisense oligomer is administered intermittently over a longer period of time.

Typically, one or more doses of antisense oligomer are administered, generally at regular intervals, for a period of about one to two weeks. Preferred doses for oral administration are from about 1 mg oligomer/patient to about 25 mg oligomer/patient (based on a weight of 70 kg). In some cases, doses of greater than 25 mg oligomer/patient may be necessary. For IV administration, the preferred doses are from about 0.5 mg oligomer/patient to about 10 mg oligomer/patient (based on an adult weight of 70 kg).

The antisense compound is generally administered in an amount and manner effective to result in a peak blood concentration of at least 200-400 nM antisense oligomer.

In general, the method comprises administering to a subject, in a suitable pharmaceutical carrier, an amount of an antisense agent effective to inhibit the biological activity of a bacterial 16S or 23S rRNA target sequence of interest.

It follows that a morpholino antisense oligonucleotide composition may be administered in any convenient vehicle which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of the antisense oligonucleotide into cells. (See, e.g., Williams, S. A., *Leukemia* 10 (12):1980-1989, 1996; Lappalainen et al., *Antiviral Res.* 23:119, 1994; Uhlmann et al., ANTISENSE OLIGONUCLEOTIDES: A NEW THERAPEUTIC PRINCIPLES, *Chemical Reviews*, Volume 90, No. 4, pages 544-584, 1990; Gregoriadis, G., Chapter 14, *Liposomes, Drug Carriers in Biology and Medicine*, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu G Y and Wu C H, *J. Biol. Chem.* 262:44294432, 1987.)

Sustained release compositions are also contemplated within the scope of this application. These may include semipermeable polymeric matrices in the form of shaped articles such as films or microcapsules.

In one aspect of the method, the subject is a human subject, typically a subject diagnosed as having a localized or systemic bacterial infection.

In another aspect, the condition of the patient may dictate prophylactic administration of an antisense oligomer of the invention, i.e., a patient who (1) is immunocompromised; (2) is a burn victim; (3) has an indwelling catheter; (4) is about to undergo or has recently undergone surgery, etc.

In another application of the method, the subject is a livestock animal, e.g., a chicken, turkey, pig, cow or goat, etc, and the treatment is either prophylactic or therapeutic.

In addition, the methods of the invention are applicable to treatment of any condition wherein inhibiting or eliminating the growth of bacteria would be effective to result in an improved therapeutic outcome for the subject under treatment.

It will be understood that an effective in vivo treatment regimen using the antisense oligonucleotides of the invention will vary according to the frequency and route of administration, as well as the condition of the subject under treatment (i.e., prophylactic administration versus administration in response to localized or systemic infection). Accordingly, such in vivo therapy will generally require monitoring by tests appropriate to the particular type of bacterial infection under treatment and a corresponding adjustment in the dose or treatment regimen in order to achieve an optimal therapeutic outcome.

B. Monitoring Treatment

The efficacy of a given therapeutic regimen involving the methods described herein may be monitored, e.g., by general indicators of infection, such as complete blood count (CBC), nucleic acid detection methods, immunodiagnostic tests or bacterial culture.

Identification and monitoring of bacterial infection generally involves one or more of (1) nucleic acid detection methods; (2) serological detection methods, i.e., conventional immunoassay; (3) culture methods; and (4) biochemical methods. Such methods may be qualitative or quantitative.

DNA probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). In addition, nucleic amplification tests (e.g., PCR) may be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot.

In general, procedures and/or reagents for immunoassay of bacterial infections are routinely employed by those of skill in the art. In addition, monoclonal antibodies specific to particular bacterial strains or species are often commercially available.

Culture methods may be used to isolate and identify particular types of bacteria, by employing techniques including, but not limited to, aerobic versus anaerobic culture, and growth and morphology under various culture conditions.

Exemplary biochemical tests include Gram stain (Gram, 1884; Gram positive bacteria stain dark blue, and Gram negative stain red), enzymatic analyses (i.e., oxidase, catalase positive for *Pseudomonas aeruginosa*), and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The antisense oligomer treatment regimen may be adjusted (dose, frequency, route, etc.), as indicated, based on the results of immunoassays, other biochemical tests and physiological examination of the subject under treatment.

While the invention has been described with reference to specific methods and embodiments, it will be appreciated that various modifications may be made without departing from the invention.

Materials and Methods

Standard recombinant DNA techniques were employed in all constructions, as described in Ausubel, F M, et al., in CURRENT PROTOCOLS IN MOLECULAR BIOLOGY, John Wiley and Sons, Inc., Media, Pa., 1992 and Sambrook J, et al., in MOLECULAR CLONING: A LABORATORY MANUAL, Cold Spring Harbor Laboratory Press, Cold Spring Harbor, N.Y., Vol. 2, 1989), both of which are expressly incorporated by reference herein.

Plasmid. The plasmid used for studies in support of the present invention was engineered using pCi-Neo mammalian expression vector (Promega), by inserting 36 bases of the c-myc target region along with the coding region for firefly luciferase into the vector in the polylinker downstream from the T7 promoter. The A from the ATG of codon No. 1 of luciferase was removed by in vitro mutagenesis, leaving the ATG that is present in the c-myc sequence in frame with the reporter. The plasmid, pCiNeo(myc)luc6A, also contained the b-lactamase gene coding for antibiotic resistance and was transformed into *Escherichia Coli* DH5.

Bacterial Cultures. In evaluating the effectiveness of antisense oligonucleotides of the invention, approximately 3 ml bacterial cultures were aliquoted into plastic snap cap tubes from a 45 ml starting culture in Luria-Bertani (LB) Broth containing 4.5 mg of Ampicillin and a single bacterial colony taken from a freshly streaked LB agar plate containing 100 g/mL ampicillin. The test oligomer diluted in phosphate buffered saline (PBS) was added to the cultures, incubated at 37° C. for a specific time, e.g., 16 or 26 hours with shaking at 210 rpm, then placed on ice for 15 minutes.

Culture staining microscopy and colony scanning. Bacterial plate counts require that a measured volume of material be added to agar either by the pour plate or spread plate technique. If the original sample has a large number of bacteria, dilutions are prepared and plated. The plates are incubated and the number of colony-forming units (CFU) reflect the viable organisms in the sample. The colonies may be counted manually using a microscope, however, it is preferred that an automatic colony counter be employed (e.g., as offered by Bioscience International, Rockville, Md.). Bacterial cultures are stained in accordance with standard Gram staining protocols. The stained bacterium are visualized using a Nikon Optiphot-2 upright microscope, with images magnified 1000× using the combination of an 100× oil immersion lens and the 10× magnification of the camera. The camera used to capture the images is a Nikon N8008S. The images are taken using bright field microscopy with a 4 second exposure on a setting 5 light output. A preferred film was Kodak Gold 400 ASA. After developing, the images are scanned using a Microtek Scan Maker 4, then cropped using Adobe PhotoShop.

Sequence Listing Table

| Description | SEQ ID NO. |
|---|---|
| *E. coli* GenBank Accession No: X80725 | 1 |
| *Salmonella thyphimurium* GenBank Accession No: U88545 | 2 |
| *Pseudomonas aeruginosa* GenBank Accession No: AF170358 | 3 |
| *Vibrio cholera* GenBank Accession No: AF118021 | 4 |
| *Staphylococcus aureus* GenBank Accession No: Y15856 | 6 |
| *Mycobacterium tuberculosis* GenBank Accession No: X52917 | 7 |
| *Helicobacter pylori* GenBank Accession No: M88157 | 8 |
| *Streptococcus pneumoniae* GenBank Accession No: AF003930 | 9 |
| *Treponema palladium* GenBank Accession No: AJ010951 | 10 |
| *Chlamydia trachomatis* GenBank Accession No: D85722 | 11 |
| *Bartonella henselae* GenBank Accession No: X89208 | 12 |
| *Hemophilis Influenza* GenBank Accession No: M35019 | 13 |
| *Shigella dysenterae* GenBank Accession No: X96966 | 14 |
| 0-1-23-15 (BS-1; Table 2A)<br>5'-GGA CTA CGA CGC ACT TTA TGA G-3' (22-mer) | 15 |
| 0-1-23-16 (BS-2; Table 2A)<br>5'-GGT CCG CTT GCT CTC GCG AGG-3' (21-mer) | 16 |
| 0-1-23-17 (NS-1; Table 2A)<br>5'-GCA AAG GTA TTA ACT TTA CTC-3' (21-mer) | 17 |
| 0-1-23-18 (NS-2; Table 2A)<br>5'-GCT GCG GTT ATT AAC CAC AAC-3' (21-mer) | 18 |
| 0-1-23-9 (*E. coli* 16S)<br>5'-GCA CTT TAT GAG GTC CGC TTG-3' (21-mer) | 19 |
| TGCTGCCTCCCGTAGGAGTCT | Table 2A-broad | 21 |
| ATTACCGCGGCTGCTGGCACG | Table 2A-broad | 22 |
| ACCAGGGTATCTAATCCTGTT | Table 2A-broad | 23 |
| CACATGCTCCACCGCTTGTGC | Table 2B-broad | 24 |
| TTGCGGGACTTAACCCAACAT | Table 2B-broad | 25 |
| CGCGGCTGCTGGCACGTAGTT | Table 3-Gram positive | 27 |
| ACTTAACCCAACATCTCACGA | Table 3-Gram positive | 28 |
| TTTACGCCCAGTAATTCCGA | Table 4-Gram negative | 29 |
| ACTCCCATGGTGTGACGGGCGG | Table 4-Gram negative | 30 |
| AATCTGAGCCATGATCAAACT | Table 2A | 31 |
| CCCTCTTTGTGCTTGCGACGT | Table 2A | 32 |
| ACCCCCCTCTACGAGACTCAA | Table 2A | 33 |

-continued

| Description | | SEQ ID NO. |
|---|---|---|
| CCACGCCTCAAGGGCACAACC | Table 2A | 34 |
| TCTCATCTCTGAAAACTTCCG | Table 2A | 35 |
| CATGATCAAACTCTTCAATTT | Table 2A | 36 |
| CCCTCTTTGGTCTTGCGACGT | Table 2A | 37 |
| TACCCCCCTCTACGAGACTCA | Table 2A | 38 |
| GCCACGCCTCAAGGGCACAAC | Table 2A | 39 |
| CAGAGAGCAAGCCCTCTTCAT | Table 2A | 40 |
| CCTGCTTTCTCCCGTAGGACG | Table 2A | 41 |
| CACCACCCTCTGCCATACTCT | Table 2A | 42 |
| CTAAGATCTCAAGGATCCCAA | Table 2A | 43 |
| GGCCTGCCGCCAGCGTTCAAT | Table 2A | 44 |
| CCCTCTTTGGTCCGTAAACAT | Table 2A | 45 |
| CCCCCTCTACAAGACTGTAGC | Table 2A | 46 |
| ACGACTRTAGGTCACAACCTC | Table 2A | 47 |
| AGGATCAAACTCTTATGTTCA | Table 2B | 48 |
| CCTGCTTTCCCTCTCAAGACG | Table 2B | 49 |
| CACCTCCCTCTGACACACTCG | Table 2B | 50 |
| CCAAGCAATCAAGTTGCCCAA | Table 2B | 51 |
| CCAGCGTTCATCCTGAGCCAG | Table 2B | 52 |
| GAACCATGCGGTTCAAAATAT | Table 2B | 53 |
| CTTTCCTCTTCTGCACTCAAG | Table 2B | 54 |
| GGGGCGGAAACCCCCTAACAC | Table 2B | 55 |
| GCATGTGTTAAGCACGCCGCC | Table 2B | 56 |
| AAGACATGCATCCCGTGGTCC | Table 2B | 57 |
| CAGTCTCCCCTGCAGTACTCT | Table 2B | 58 |
| GATCCCAAGGAAGGAAACCCA | Table 2B | 59 |
| CAGGATCAAACTCTCCATAAA | Table 2B | 60 |
| AAATCTTTCCCCCGTAGGAGT | Table 2B | 61 |
| CACCTACCTCTCCCACACTCT | Table 2B | 62 |
| TGGAGAGACTAAGCCCTCCAA | Table 2B | 63 |
| CGTCCTGAGCCAGGATCAAAT | Table 2B | 64 |
| ATGTCATGCAACATCCACTCT | Table 2B | 65 |
| ACTCTCCCCTCTTGCACTCAA | Table 2B | 66 |
| AAACCCCGGAAAGGGTCTAAC | Table 2B | 67 |
| TCTGAGCCATGATCAAACTCT | Table 2B | 68 |
| ACCCCTTATGAAGCACTGAGT | Table 2B | 69 |
| AGTTTCCCTTCCGTAATTCAA | Table 2B | 70 |
| CACTGAAGCTCTTGCCCCAAC | Table 2B | 71 |

-continued

| Description | | SEQ ID NO. |
|---|---|---|
| GAACCAAGATCAAATTCTCAG | Table 2C | 72 |
| GTTACTCGGATGCCCAAATAT | Table 2C | 73 |
| CCTTTTCTCCATCTACCCTCT | Table 2C | 74 |
| GGATGGGGTTGAGACCATCCA | Table 2C | 75 |
| AGCGTTCATCCTGAGCCAGGA | Table 2C | 76 |
| AAATCTTTCTCCAGTAGGACG | Table 2C | 77 |
| CACTCACCTCTTCCATACTCA | Table 2C | 78 |
| ACTGAGCAGTAAACCACCCAA | Table 2C | 79 |
| CATGATCAAACTCTTCAATTN | Table 2C | 80 |
| CACTTTCATCTTCCGATAATA | Table 2C | 81 |
| CCTCCCTAAAGTACTCTAGTT | Table 2C | 82 |
| CAGAGTTAAACCCCAACCCCC | Table 2C | 83 |
| GCCAGCGTTCAATCTGAGCCA | Table 2C | 84 |
| CCCTCTTTGGTCTTGCGACGT | Table 2C | 85 |
| TACCCCCCTCTACGAGACTCA | Table 2C | 86 |
| GCCACGCCTCAAGGGCACAAC | Table 2C | 87 |
| CCTCGTATCTCTACAAGGTTC | Table 2C | 88 |
| CCC CAT CAT TAT GAG TGA TGT GC | AVI-1-23-19 | 89 |
| TCA TTA TGA G GTG ACC CCA | AVI-1-23-20 | 90 |
| GAT GAA CAG TTA CTC TCA TC | AVI-1-23-21 | 91 |
| ACT GAG AGA AGC TTT AAG AG | AVI-1-23-22 | 92 |
| ATG TGC ACA GTT ACT TAC AC | AVI-1-23-23 | 93 |
| CTG AGA ACA ACT TTA TGG GA | AVI-1-23-24 | 94 |
| TTA TTC TGT TGG TAA CGT CA | AVI-1-23-25 | 95 |
| CG AGT TGC AGA CTG CGA TC | AVI-1-23-26 | 96 |
| ATC TGA GCC ATG ATC AAA CT | AVI-1-23-27 | 97 |
| TGT CTC AGT TCC AGT GTT GC | AVI-1-23-28 | 98 |
| GTC TTC GTC CAG GGG GCC GC | AVI-1-23-29 | 99 |
| CAC CTG TCT CAC GGT TCC CG | AVI-1-23-30 | 100 |
| CGC CCT CCC GAA GTT AAG CT | AVI-1-23-31 | 101 |
| GGC ACG CCG CCA GCG TTC G | AVI-1-23-32 Table 10 | 102 |
| TGT CTC AGT CCC AAT GTG GC | AVI-1-23-33 Table 10 | 103 |
| GTT ACA GAC CAG AGA GCC GC | AVI-1-23-34 Table 10 | 104 |
| CAC CTG TCA CTT TGC CCC CG | AVI-1-23-35 Table 10 | 105 |
| GGC GGC TGG CTC CAA AAG G | AVI-1-23-36 Table 10 | 106 |
| CAC CCG TTC GCC ACT CCT C | AVI-1-23-37 Table 10 | 107 |
| TCA ATT CCT TTG AGT TTC AA | AVI-1-23-38 Table 10 | 108 |

| Description | | SEQ ID NO. |
|---|---|---|
| GCA ATC CGC ACT GAG AGA AGC TTT AAG AG | AVI-1-23-39 Table 10 | 109 |
| C CGC ACT GAG AGA AGC TTT AAG AG | AVI-1-23-40 Table 10 | 110 |
| GAG AGA AGC TTT AAG AG | AVI-1-23-41 Table 10 | 111 |
| G AGA AGC TTT AAG AG | AVI-1-23-42 Table 10 | 112 |
| A AGC TTT AAG AG | AVI-1-23-43 Table 10 | 113 |
| GAC TAC CAG GGT ATC TAA TC | AVI-1-23-44 Table 10 | 114 |
| CAG CGA CAC CCG AAA GCC CC | AVI-1-23-45 Table 10 | 115 |
| GTG CCA AGG CAT CCA CCG TG | AVI-1-23-46 Table 11 | 116 |
| CAT ACT CAA ACG CCC TAT TC | AVI-1-23-47 Table 11 | 117 |
| CCT TAG CCT CCT GCG TCC C | AVI-1-23-48 Table 11 | 118 |
| GGG GTC TTT CCG TCC TGT CG | AVI-1-23-49 Table 11 | 119 |
| CGA TCG ATT AGT ATC ACT CC | AVI-1-23-50 Table 11 | 120 |
| T GAG AGA AGC TTT AAG AG | AVI-1-23-63 Table 10 | 121 |
| CT GAG AGA AGC TTT AAG AG | AVI-1-23-66 Table 10 | 122 |
| GCG ACA CCC GAA AGC GCC | AVI-1-23-67 Table 10 | 123 |
| TAC AGA CCA GAG AGC CGC | AVI-1-23-68 Table 10 | 124 |
| CGA CAC CCG AAA GCG CC | AVI-1-23-69 Table 10 | 125 |
| A GCG ACA CCC GAA AGC GCC | AVI-1-23-70 Table 10 | 126 |
| CG ACA CCC GAA AGC GCC A | AVI-1-23-71 Table 10 | 127 |
| MG AMA MMM GAA AGM GMM | AVI-1-23-72 Table 10 | 128 |
| TAM AGA MMA GAG AGM MGM | AVI-1-23-73 Table 10 | 129 |
| MMM MAM MTT MTT MMG G | AVI-1-23-74 Table 10 | 130 |
| CAC CGC GGC GTG CTG ATC C | AVI-1-23-75 Table 10 | 131 |
| CCC CAC CTT CCT CCG G | AVI-1-23-76 Table 10 | 132 |
| CCG CTT GTG CGG GCC CCC | AVI-1-23-77 Table 10 | 133 |
| CAC CGC GGC GTG CTG ATC | AVI-1-23-78 Table 10 | 134 |
| CAC CGC GGC GTG CTG AT | AVI-1-23-79 Table 10 | 135 |
| ACC GCG GCG TGC TGA TCC | AVI-1-23-80 Table 10 | 136 |
| CCG CGG CGT GCT GAT CC | AVI-1-23-81 Table 10 | 137 |
| ACC GCG GCG TGC TGA TC | AVI-1-23-82 Table 10 | 138 |
| 5'-ACG TTG AGG GGC ATC GTC GC-3' | AVI 1-22-126 AS to c-myc | 139 |

It is claimed:

1. A method of treating an infection in a human or mammalian animal subject, caused by *Escherichia coli, Salmonella thyphimurium, Pseudomonas aeruginosa, Vibrio cholera, Neisseria gonorrhoea, Helicobacter pylori, Treponema palladium, Chlamydia trachomatis, Bartonella henselae, Hemophilis influenza* or *Shigella dysenterae*, comprising
administering to the subject, in a pharmaceutically effective amount, a substantially uncharged morpholino antisense oligomer containing from 10 to 40 nucleotide subunits, each of said subunits comprising a morpholino ring supporting a base-pairing moiety effective to bind by Watson-Crick base pairing to a respective nucleotide base, said base-pairing moieties including a targeting nucleic acid sequence of at least 10 nucleotides in length contained in SEQ ID NO:30, which is able to stably hybridize to a bacterial 16S rRNA from the infecting bacterium, wherein
adjacent subunits are linked together by phosphorous-containing linkages, one to three atoms long, joining the morpholino nitrogen of one subunit to the 5' exocyclic carbon of an adjacent subunit, and the ratio of uncharged linkages to charged linkages in the oligomer is at least 4:1.

2. The method of claim 1, wherein said oligomer is able to hybridize with the bacterial 16S rRNA at a Tm substantially greater than 37° C.

3. The method of claim 2, wherein the uncharged linkages in the oligomer are phosphorodiamidate linkages, having the structure below, where $X=NR_2$, R is hydrogen or methyl, $Y_1=O$, $Z=O$, and $P_i$ is a purine or pyrimidine base pairing moiety effective to bind, by base specific hydrogen bonding, to a base in a polynucleotide.

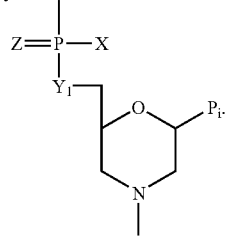

4. The method of claim 1, wherein the antisense oligomer is administered in an amount and manner effective to result in a peak blood concentration of at least 200-400 nM antisense oligomer.

5. The method of claim 1, for treating bacterial infections of the skin, wherein said administering is by a topical route.

6. The method of claim 1, for use in treating a bacterial respiratory infection, wherein said administering is by inhalation.

* * * * *

SEQUENCE LISTING

<160> NUMBER OF SEQ ID NOS: 139

<210> SEQ ID NO 1
<211> LENGTH: 1450
<212> TYPE: DNA
<213> ORGANISM: Escherichia coli

```
<220> FEATURE:
<221> NAME/KEY: misc_feature
<222> LOCATION: (1)...(1450)
<223> OTHER INFORMATION: n = A,T,C or G

<400> SEQUENCE: 1
agtttgatca tggctcagat tgaacgctgg cggcaggcct aacacatgca agtcgaacgg      60
taacaggaag cagcttgctg ctttgctgac gagtggcgga cgggtgagta atgtctggga     120
aactgcctga tggagggggga taactactgg aaacggtagc taataccgca taacgtcgca    180
agcacaaaga gggggacctt agggcctctt gccatcggat gtgcccagat gggattagct     240
agtaggtggg gtaacggctc acctaggcga cgatccctag ctggtctgag aggatgacca     300
gcaacactgg aactgagaca cggtccagac tcctacggga ggcagcagtg gggaatattg     360
cacaatgggc gcaagcctga tgcagccatg cngcgtgtat gaagaaggcc ttcgggttgt     420
aaagtacttt cagcggggag gaagggagta agttaatac ctttgctcat tgacgttacc      480
cgcagaagaa gcaccggcta actccgtgcc agcagccgcg gtaatacgga gggtgcaagc     540
gttaatcgga attactgggc gtaaagcgca cgcaggcggt ttgttaagtc agatgtgaaa     600
tccccgggct caacctggga actgcatctg atactggcaa gcttgagtct cgtagagggg     660
ggtagaattc caggtgtagc ggtgaaatgc gtagagatct ggaggaatac cggtggcgaa     720
ggcggccccc tggacgaaga ctgacgctca ggtgcgaaag cgtggggagc aaacaggatt     780 agatacctg gtagtccacg ccgtaaacga tgtcgacttg gaggttgtgc ccttgaggcg      840
tggcttccgg anntaacgcg ttaagtcgac cgcctgggga gtacgccgc aaggttaaaa      900 ctcaaatgaa ttgacggggg ccgcacaagc ggtggagcat gtggtttaat tcgatgcaac     960
gcgaagaacc ttacctggtc ttgacatcca cggaagtttt cagagatgag aatgtgcctt    1020
cgggaaccgt gagacaggtg ctgcatggct gtcgtcagct cgtgttgtga aatgttgggt    1080
taagtcccgc aacgagcgca acccttatcc tttgttgcca gcggtccggc cgggaactca    1140
aaggagactg ccagtgataa actggaggaa ggtggggatg acgtcaagtc atcatggccc    1200
ttacgaccag ggctacacac gtgctacaat ggcgcataca agagaagcg acctcgcgag     1260 agcaagcgga cctcataaag tgcgtcgtag tccggattgg agtctgcaac tcgactccat    1320
gaagtcggaa tcgctagtaa tcgtggatca gaatgccacg gtgaatacgt tcccgggcct    1380
tgtacacacc gcccgtcaca ccatgggagt gggttgcaaa agaagtaggt agcttaactt    1440
cgggagggcg                                                           1450

<210> SEQ ID NO 2
<211> LENGTH: 1541
<212> TYPE: DNA
<213> ORGANISM: Salmonella thyphimurium

<400> SEQUENCE: 2
aaattgaaga gtttgatcat ggctcagatt gaacgctggc ggcaggccta acacatgcaa      60
gtcgaacggt aacaggaagc agcttgctct ttgctgacga gtggcggacg ggtgagtaat     120
gtctgggaaa ctgcctgatg gagggggata actactggaa acgtggcta ataccgcata     180 acgtcgcaag accaaagagg gggaccttcg ggcctcttgc catcggatgt gcccagatgg     240
gattagctag taggtggggt aacggctcac ctaggcgacg atccctagct ggtctgagag     300
gatgaccagc cacactgaag ctgaagcacg gtccagactc ctacgggagg cagcagtggg     360
gaatattgca caatgggcgc aagcctgatg cagccatgcc gcgtgtatga agaaggcctt     420
```

-continued

```
cgggttgtaa agtactttca gcggggagga aggtgttgtg gttaataacc gcagcaattg    480
acgttacccg cagaagaagc accggctaac tccgtgccag cagccgcggt aatacggagg    540
gtgcaagcgt taatcggaat tactgggcgt aaagcgcacg caggcggttt gttaagtcag    600
atgtgaaatc cccgggctca acctgggaac tgcatctgat actggcaagc ttgagtctcg    660
tagaggggg tagaattcca ggtgtagcgg tgaaatgcgt agagatctgg aggaataccg    720
gtggcgaagg cggcccctg gacgaagact gacgctcagg tgcgaaagcg tggggagcaa    780
acaggattag ataccctggt agtccacgcc gtaaacgatc tctacttgga ggttgtgccc    840
ttgaggcgtg gcttccggag ctaacgcgtt aagtagagtg cttggggagt acggccgcaa    900
ggttaaaact caaatgaatt gacggggggcc cgcacaagcg gtggagcatg tggtttaatt    960
cgatgcaacg cgaagaacct tacctggtct tgacatccac agaactttcc agagatgaga   1020
ttgtgccttc gggaactgtg agacaggtgc tgcatggctg tcgtcagctc gtgttgtgaa   1080
atgttgggtt aagtcccgca acgagcgcaa cccttatcct tgttgccag cggtccggcc   1140
gggaactcaa aggagactgc cagtgataaa ctggaggaag tgggggatga cgtcaagtca   1200
tcatggccct tacgaccagg gctacacacg tgctacaatg gcgcatacaa agagaagcga   1260
cctcgcgaga gcaagcggac ctcataaagt gcgtcgtagt ccggattgga gtctgcaact   1320
cgactccatg aagtcggaat cgctagtaat cgtggatcag aatgccacgg tgaatacgtt   1380
cccgggcctt gtacacaccg cccgtcacac catgggagtg ggttgcaaaa gaagtaggta   1440
gcttaacctt cgggagggcg cttaccactt tgtgattcat gactggggtg aagtcgtaac   1500
aaggtaaccg taggggaacc tgcggttgga tcacctcctt a                       1541
```

<210> SEQ ID NO 3
<211> LENGTH: 1467
<212> TYPE: DNA
<213> ORGANISM: Pseudomonas aeruginosa

<400> SEQUENCE: 3

```
atgaagaggg cttgctctct gattcagcgg cggacgggtg agtaatgcct aggaatctgc     60
ctgatagtgg gggacaacgt ttcgaaagga acgctaatac cgcatacgtc ctacgggaga    120
aagcagggga ccttcgggcc ttgcgctatc agatgagcct aggtcggatt agctagttgg    180
tgaggtaacg gctcaccaag cgacgatcc gtaactggtc tgagaggatg atcagtcaca    240
ctggaactga gacacggtcc agactcctac gggaggcagc agtggggaat attggacaat    300
gggcgaaagc ctgatccagc catgccgcgt gtgtgaagaa ggtcttcgga ttgtaaagca    360
cttaagttg ggaggaaggg cattaaccta atacgttagt gttttgacgt taccgacaga    420
ataagcaccg gctaacttcg tgccagcagc cgcggtaata cgaagggtgc aagcgttaat    480
cggaattact gggcgtaaag cgcgcgtagg tggtttgtta agttgaatgt gaaagccccg    540
ggctcaacct gggaactgca tccaaaactg gcaagctaga gtatggcaga gggtggtgga    600
atttcctgtg tagcggtgaa atgcgtagat ataggaagga acaccagtgg cgaaggcgac    660
cacctgggct aatactgaca ctgaggtgcg aaagcgtggg gagcaaacag gattagatac    720
cctggtagtc cacgccgtaa acgatgtcga ctagccgttg ggatccttga gatcttagtg    780
gcgcagctaa cgcattaagt cgaccgcctg gggagtacgg ccgctaggtt aaaactctaa    840
tgaattgacg ggggcccgca caagcggtgg agcatgtggt ttaattcgaa gcaacgcgaa    900
gaaccttacc aggccttgac atgcagagaa ctttccagag atggattggt gccttcggga    960
actctgacac aggtgctgca tggctgtcgt cagctcgtgt cgtgagatgt tgggttaagt   1020
```

-continued

```
cccgtaacga gcgcaaccct tgtccttagt taccagcacg ttaaggtggg cactctaagg        1080
agactgccgg tgacaaaccg gaggaaggtg gggatgacgt caagtcatca tggcccttac        1140
ggcctgggct acacacgtgc tacaatggtc ggtacaaagg gttgccaagc cgcgaggtgg        1200
agctaatccc ataaaaccga tcgtagtccg gatcgcagtc tgcaactcga ctgcgtgaag        1260
tcggaatcgc tagtaatcgt gaatcagaat gtcacggtga atacgttccc gggccttgta        1320
cacaccgccc gtcacaccat gggagtgggt tgctccagaa gtagctagtc taaccttcgg        1380
ggggacggtt accacggagg tattcatgac tggggtgaag tcgtaacaag gtagccgtag        1440
gggaacctgc ggctggatca cctcctt                                            1467
```

<210> SEQ ID NO 4
<211> LENGTH: 1500
<212> TYPE: DNA
<213> ORGANISM: Vibrio cholera

<400> SEQUENCE: 4

```
attgaacgct ggcggcaggc ctaacacatg caagtcgagc ggtaacattt caaaagcttg         60
cttttgaaga tgacgagcgg cggacgggtg agtaatggct gggaacctgc cctgacgtgg        120
gggataacag ttggaaacga ctgctaatac cgcatgatgt ttacggacca agagggggga        180
tyttcggacy tytcgcgtcg ggatgggccc agttgggatt agctagttgg tgaggtaatg        240
gctcaccaag gcgacgatcc ctagctggtt tgagaggatg atcagccaca ctggaactga        300
gacacggtcc agactcctac gggaggcagc agtggggaat attgcacaat gggcgcaagc        360
ctgatgcagc catgccgcgt gtgtgaagaa ggccttcggg ttgtaaagca ctttcagcag        420
tgaggaaggt tggtgcgtta atagcgtatc aatttgacgt tagctgcaga agaagcaccg        480
gctaactccg tgccagcagc cgcggtaata cggagggtgc gagcgttaat cggaattact        540
gggcgtaaag cgcatgcagg cggtttgtta agcaagatgt gaaagccccg gctcaacctg        600 ggaaccgca ttttgaactg gcaggctaga gtcttgtaga gggggggtaga atttcaggtg        660 tagcggtgaa atgcgtagag atctgaagga ataccggtgg cgaaggcggc ccctggaca         720 aagactgacg ctcagatgcg aaagcgtggg gagcaaacag gattagatac cctggtagtc        780
cacgctgtaa acgatgtcta cttggaggtt gtgacctara gtcgtggctt tcggagctaa        840
cgcgttaagt agaccgcctg gggagtacgg tcgcaagatt aaaactcaaa tgaattgacg        900
ggggcccgca caagcggtgg agcatgtggt ttaattcgat gcaacgcgaa gaaccttacc        960
tactcttgac atccagagaa gccgaaagag atttggtgt gccttcggga actctgagac        1020
aggtgctgca tggctgtcgt cagctcgtgt tgtgaaatgt tgggttaagt cccgcaacga       1080
gcgcaaccct tatccttgtt tgccagcgag taatgtcggg aactccaggg agactgccgg       1140
tgataaaccg gaggaaggtg gggacgacgt caagtcatca tggcccttac gagtagggct       1200
acacacgtgc tacaatggca tatacagagg cagcgaggc cgcgaggtgg agcgaatccc       1260
agaaagtatg tcgtagtccg gatcggagtc tgcaactcga ctccgtgaag tcggaatcgc       1320
tagtaatcgt gaatcagaat gtcacggtga atacgttccc gggccttgta cacaccgccc       1380
gtcacaccat gggagtgggc tgcaccagaa gtagatagc taaccttcgg gagggcgttt        1440
accacggtgt ggttcatgac tggggtgaag tcgtaacaag gtagccctag ggaacctgg        1500
```

<210> SEQ ID NO 5
<211> LENGTH: 1544
<212> TYPE: DNA

<213> ORGANISM: Neisseria gonorrhoea

<400> SEQUENCE: 5

```
tgaacataag agtttgatcc tggctcagat tgaacgctgg cggcatgctt tacacatgca      60
agtcggacgg cagcacaggg aagcttgctt ctcgggtggc gagtggcgaa cgggtgagta     120
acatatcgga acgtaccggg tagcggggga taactgatcg aaagatcagc taataccgca     180
tacgtcttga gagggaaagc aggggacctt cgggccttgc gctatccgag cggccgatat     240
ctgattagct ggttggcggg gtaaaggccc accaaggcga cgatcagtag cgggtctgag     300
aggatgatcc gccacactgg gactgagaca cggcccagac tcctacggga ggcagcagtg     360
gggaattttg gacaatgggc gcaagcctga tccagccatg ccgcgtgtct gaagaaggcc     420
ttcgggttgt aaaggacttt tgtcagggaa gaaaaggctg ttgccaatat cggcggccga     480
tgacggtacc tgaagaataa gcaccggcta actacgtgcc agcagccgcg gtaatacgta     540
gggtgcgagc gttaatcgga attactgggc gtaaagcggg cgcagacggt tacttaagca     600
ggatgtgaaa tccccgggct caacccggga actgcgttct gaactgggtg actcgagtgt     660
gtcagaggga ggtggaattc cacgtgtagc agtgaaatgc gtagagatgt ggaggaatac     720
cgatggcgaa ggcagcctcc tgggataaca ctgacgttca tgtccgaaag cgtgggtagc     780
aaacaggatt agataccctg gtagtccacg ccctaaacga tgtcaattag ctgttgggca     840
acttgattgc ttggtagcgt agctaacgcg tgaaattgac cgcctgggga gtacggtcgc     900
aagattaaaa ctcaaaggaa ttgacgggga cccgcacaag cggtggatga tgtggattaa     960
ttcgatgcaa cgcgaagaac cttacctggt tttgacatgt gcggaatcct ccggagacgg    1020
aggagtgcct tcgggagccg taacacaggt gctgcatggc tgtcgtcagc tcgtgtcgtg    1080
agatgttggg ttaagtcccg caacgagcgc aacccttgtc attagttgcc atcattcggt    1140
tgggcactct aatgagactg ccggtgacaa gccggaggaa ggtggggatg acgtcaagtc    1200
ctcatggccc ttatgaccag ggcttcacac gtcatacaat ggtcggtaca gagggtagcc    1260
aagccgcgag gcggagccaa tctcacaaaa ccgatcgtag tccggattgc actctgcaac    1320
tcgagtgcat gaagtcggaa tcgctagtaa tcgcaggtca gcatactgcg gtgaatacgt    1380
tcccgggtct tgtacacacc gcccgtcaca ccatgggagt gggggatacc agaagtaggt    1440
agggtaaccg caaggagtcc gcttaccacg gtatgcttca tgactggggt gaagtcgtaa    1500
caaggtagcc gtaggggaac tgcggctgg atcacctcct ttct                      1544
```

<210> SEQ ID NO 6
<211> LENGTH: 1484
<212> TYPE: DNA
<213> ORGANISM: Staphylococcus aureus

<400> SEQUENCE: 6

```
ctggctcagg atgaacgctg gcggcgtgcc taatacatgc aagtcgagcg aacggacgag      60
aagcttgctt ctctgatgtt agcggcggac gggtgagtaa cacgtggata acctacctat     120
aagactggga taacttcggg aaaccggagc taataccaga taatattttg aaccgcatgg     180
ttcaaaagtg aaagacggtc ttgctgtcac ttatagatgg atccgcgctg cattagctag     240
ttggtaaggt aacggcttac caaggcaacg atgcatagcc gacctgagag ggtgatcgkc     300
cacactggaa ctgagacacg gtccagactc ctacgggagg cagcagtagg gaatcttccg     360
caatgggcga aagcctgacg gagcaacgcc gcgtgagtga tgaaggtctt cggatcgtaa     420
aactctgtta ttagggaaga acatatgtgt aagtaactgt gcacatcttg acggtaccta     480
```

```
atcagaaagc cacggctaac tacgtgccag cagccgcggt aatacgtagg tggcaagcgt    540
tatccggaat tattgggcgt aaagcgcgcg taggcggttt ttyaagtctg atgtgaaagc    600
ccacggctca accgtggagg gtcattggaa actggaaaac ttgagtgcag aagaggaaag    660
tggaattcca tgtgtagcgg tgaaatgcgc agagatatgg aggaacacca gtggcgaagg    720
cgactttctg gtctgtaact gacgctgatg tgcgaaagcg tggggatcaa acaggattag    780
ataccctggt agtccacgcc gtaaacgatg agtgctargt gttaggggt ttccgcccct     840 tagtgctgca gctaacgcat taagcactcc gcctgggag tacgaccgca aggttgaaac     900
tcaaaggaat tgacggggac ccgcacaagc ggtggagcat gtggtttaat tcgaagcaac    960
gcgaagaacc ttaccaaatc ttgacatcct ttgacaactc tagagataga gccttcccct   1020 tcggggggaca aagtgacagg tggtgcatgg ttgtcgtcag ctcgtgtcgt gagatgttgg   1080
gttaagtccc gcaacgagcg caaccettaa gcttagttgc catcattaag ttgggcactc   1140
taagttgact gccggtgaca aaccggagga aggtggggat gacgtcaaat catcatgccc   1200
cttatgattt gggctacaca cgtgctacaa tggacaatac aaagggcagc gaaaccgcga   1260
ggtcaagcaa atcccataaa gttgttctca gttcggattg tagtctgcaa ctcgactaca   1320
tgaagctgga atcgctagta atcgtagatc agcattctac ggtgaatacg ttcccgggtc   1380
ttgtacacac cgcccgtcac accacgagag tttgtaacac ccgaagccgg tggagtaacc   1440
ttttaggagc tagccgtcga aggtgggaca aatgattggg gtga                    1484

<210> SEQ ID NO 7
<211> LENGTH: 1464
<212> TYPE: DNA
<213> ORGANISM: Mycobacterium tuberculosis

<400> SEQUENCE: 7
ggcggcgtgc ttaacacatg caagtcgaac ggaaaggtct cttcggagat actcgagtgg     60
cgaacgggtg agtaacacgt gggtgatctg ccctgcactt cgggataagc ctgggaaact    120
gggtctaata ccggatagga ccacgggatg catgtcttgt ggtggaaagc gctttagcgg    180
tgtgggatga gcccgcggcc tatcagcttg ttggtggggt gacggcctac caaggcgacg    240
acgggtagcc ggcctgagag ggtgtccggc cacactggga ctgagatacg gcccagactc    300
ctacgggagg cagcagtggg gaatattgca caatgggcgc aagcctgatg cagcgacgcc    360
gcgtggggga tgacggcctt cgggttgtaa acctctttca ccatcgacga aggtccgggt    420
tctctcggat tgacggtagg tggagaagaa gcaccggcca actacgtgcc agcagccgcg    480
gtaatacgta gggtgcgagc gttgtccgga attactgggc gtaaagagct cgtaggtggt    540
ttgtcgcgtt gttcgtgaaa tctcacggct taactgtgag cgtgcgggcg atacgggcag    600
actagagtac tgcaggggag actggaattc ctggtgtagc ggtggaatgc gcagatatca    660
ggaggaacac cggtggcgaa ggcgggtctc tgggcagtaa ctgacgctga ggagcgaaag    720 cgtgggagc gaacaggatt agataccctg gtagtccacg ccgtaaacgg tgggtactag    780
gtgtgggttt ccttccttgg gatccgtgcc gtagctaacg cattaagtac cccgcctggg    840
gagtacggcc gcaaggctaa aactcaaagg aattgacggg ggcccgcaca agcggcggag    900
catgtggatt aattcgatgc aacgcgaaga accttacctg gtttgacat gcacaggacg    960 cgtctagaga taggcgttcc cttgtggcct gtgtgcaggt ggtgcatggc tgtcgtcagc   1020
tcgtgtcgtg agatgttggg ttaagtcccg caacgagcgc aacccttgtc tcatgttgcc   1080
```

-continued

```
agcacgtaat ggtggggact cgtgagagac tgccggggtc aactcggagg aaggtgggga    1140
tgacgtcaag tcatcatgcc ccttatgtcc agggcttcac acatgctaca atggccggta    1200
caaagggctg cgatgccgcg aggttaagcg aatccttaaa agccggtctc agttcggatc    1260
ggggtctgca actcgacccc gtgaagtcgg agtcgctagt aatcgcagat cagcaacgct    1320
gcggtgaata cgttcccggg ccttgtacac accgcccgtc acgtcatgaa agtcggtaac    1380
acccgaagcc agtggcctaa ccctcgggag ggagctgtcg aagtgggat cggcgattgg     1440 gacgaagtcg taacaaggta gccg                                           1464
```

<210> SEQ ID NO 8
<211> LENGTH: 1450
<212> TYPE: DNA
<213> ORGANISM: Helicobacter pylori
<220> FEATURE:
<221> NAME/KEY: misc_feature
<222> LOCATION: (1)...(1450)
<223> OTHER INFORMATION: n = A,T,C or G

<400> SEQUENCE: 8

```
tttatggaga gtttgatcct ggctcagagt gaacgctggc ggcgtgccta atacatgcaa     60
gtcgaacgat gaagcttcta gcttgctaga gtgctgatta gtggcgcacg ggtgagtaac    120
gcataggtca tgtgcctctt agtttgggat agccattgga aacgatgatt aataccagat    180
actcctacgg gggaaagatt tatcgctaag agatcagcct atgtcctatc agcttgttgg    240
taaggtaatg gcttaccaag gctatgacgg gtatccggcc tgagagggtg aacggacaca    300
ctggaactga gacacggtcc agactcctac gggaggcagc agtagggaat attgctcaat    360
gggggaaacc ctgaagcagc aacgccgcgt ggaggatgaa ggttttagga ttgtaaactc    420
cttttgttag agaagataat gacggtatct aacgaataag caccggctaa ctccgtgcca    480
gcagccgcgg taatacggag ggtgcaagcg ttactcggaa tcactgggcg taaagagcgc    540
gtaggcggga tagtcagtca ggtgtgaaat cctatggctt aaccatagaa ctgcatttga    600
aactactatt ctagagtgtg ggagaggtag gtggaattct tggtgtaggg gtaaaatccg    660
tagagatcaa gaggaatact cattgcgaag gcgacctgct ggaacattac tgacgctgat    720
tgcgctaaag cgtggggagc aaacaggatt agataccctg gtagtccacg ccctaaacga    780
tggatgctag ttgttggagg gcttagtctc tccagtaatg cagctaacgc attaagcatc    840
ccgcctgggg agtacggtcg caagattaaa actcaaagga atagacgggg acccgcacaa    900
gcggtggagc angtggttta attcgannnn acacgaagaa ccttacctag gcttgacatt    960
gagagaatcc gctagaaata gtggagtgtc tagcttgcta gaccttgaaa acaggtgctg    1020
cacggctgtc gtcagctcgt gtcgtgagat gttgggttaa gtcccgcaac gagcgcaacc    1080
ccntttctta gttgctaaca ggttatgctg agaactctaa ggatactgcc tccgtaagga    1140
ggaggaaggt ggggacgacg tcaagtcatc atgcccctta cgcctagggc tacacacgtg    1200
ctacaatggg gtgcacaaag agaagcaata ctgtgaagtg gagccaatct tcaaaacacc    1260
tctcagttcg gattgtaggc tgcaactcgc ctgcatgaag ctggaatcgc tagtaatcgc    1320
aaatcagcca tgttgcggtg aatacgttcc cgggtcttgt actcaccgcc cgtcacacca    1380
tgggagttgt gtttgcctta agtcaggatg ctaaattggc tactgcccac ggcacacaca    1440
gcgactgggg                                                           1450
```

<210> SEQ ID NO 9
<211> LENGTH: 1515

<212> TYPE: DNA
<213> ORGANISM: Streptococcus pneumoniae

<400> SEQUENCE: 9

| | | | | | |
|---|---|---|---|---|---|
| atttgatcct | ggctcaggac | gaacgctggc | ggcgtgccta | atacatgcaa | gtagaacgct | 60 |
| gaaggaggag | cttgcttctc | tggatgagtt | gcgaacgggt | gagtaacgcg | taggtaacct | 120 |
| gcctggtagc | gggggataac | tattggaaac | gatagctaat | accgcataag | agtggatgtt | 180 |
| gcatgacatt | tgcttaaaag | gtgcacttgc | atcactacca | gatggacctg | cgttgtatta | 240 |
| gctagttggt | ggggtaacgg | ctcaccaagg | cgacgataca | tagccgacct | gagagggtga | 300 |
| tcggccacac | tgggactgag | acacgkccca | gactcctacg | ggaggcagca | gtagggaatc | 360 |
| ttcggcaatg | gacggaagtc | tgaccgagca | acgccgcgtg | agtgaagaag | gttttcggat | 420 |
| cgtaaagctc | tgttgtaaga | agaacgag | tgtgagagtg | gaaagttcac | actgtgacgg | 480 |
| tatcttacca | gaaagggacg | gctaactacg | tgccagcagc | cgcggtaata | cgtaggtccc | 540 |
| gagcgttgtc | cggatttatt | gggcgtaaag | cgagcgcagg | cggttagata | agtctgaagt | 600 |
| taaaggctgt | ggcttaacca | tagtaggctt | tggaaactgt | ttaacttgag | tgcaagaggg | 660 |
| gagagtggaa | ttccatgtgt | agcggtgaaa | tgcgtagata | tatggaggaa | caccggtggc | 720 |
| gaaagcggct | ctctggcttg | taactgacgc | tgaggctcga | aagcgtgggg | agcaaacagg | 780 |
| attagatacc | ctggtagtcc | acgctgtaaa | cgatgagtgc | taggtgttag | acccttccg | 840 |
| gggtttagtg | ccgtagctaa | cgcattaagc | actccgcctg | gggagtacga | ccgcaaggtt | 900 |
| gaaactcaaa | ggaattgacg | ggggcccgca | caagcggtgg | agcatgtggt | ttaattcgaa | 960 |
| gcaacgcgaa | gaaccttacc | aggtcttgac | atccctctga | ccgctctaga | gatagagttt | 1020 |
| tccttcggga | cagaggtgac | aggtggtgca | tggttgtcgt | cagctcgtgt | cgtgagatgt | 1080 |
| tgggttaagt | cccgcaacga | gcgcaacccc | tattgttagt | tgccatcatt | cagttgggca | 1140 |
| ctctagcgag | actgccggta | ataaaccgga | ggaaggtggg | gatgacgtca | aatcatcatg | 1200 |
| ccccttatga | cctgggctac | acacgtgcta | caatggctgg | tacaacgagt | cgcaagccgg | 1260 |
| tgacggcaag | ctaatctctt | aaagccagtc | tcagttcgga | ttgtaggctg | caactcgcct | 1320 |
| acatgaagtc | ggaatcgcta | gtaatcgcgg | atcagcacgc | cgcggtgaat | acgttcccgg | 1380 |
| gccttgtaca | caccgcccgt | cacaccacga | gagtttgtaa | cacccgaagt | cggtgaggta | 1440 |
| accgtaagga | gccagccgcc | taaggtggga | tagatgattg | gggtgaagtc | gtaacaaggt | 1500 |
| cagccgtttg | ggaga | | | | | 1515 |

<210> SEQ ID NO 10
<211> LENGTH: 1544
<212> TYPE: DNA
<213> ORGANISM: Treponema palladium

<400> SEQUENCE: 10

| | | | | | |
|---|---|---|---|---|---|
| agagtttgat | catggctcag | aacgaacgct | ggcggcgcgt | cttaagcatg | caagtcgaac | 60 |
| ggcaagagag | gagcttgctt | ctctcctaga | gtggcggact | ggtgaggaac | acgtgggtaa | 120 |
| tctacccta | agatggggat | agctgctaga | aatagcaggt | aataccgaat | atactcagtg | 180 |
| cttcataagg | ggtattgagg | aaaggaagct | acggcttcgc | ttgaggatga | gcttgcgtcc | 240 |
| cattagctag | ttggtgaggt | aaaggcccac | caaggcgacg | atgggtatcc | ggcctgagag | 300 |
| ggtgatcrga | cacattggga | ctgagatacg | gcccaaactc | ctacggggagg | cagcagctaa | 360 |
| gaatattccg | caatggacgg | aagtctgacg | gagcgacgcc | gcgtggatga | agaaggctga | 420 |

-continued

```
aaagttgtaa aatccttttg ttgatgaaga ataagggtga gagggaatgc tcatctgatg    480
acggtaatcg acgaataagc cccggctaat tacgtgccag cagccgcggt aacacgtaag    540
gggcgagcgt tgttcggaat tatttgggcgt aaagggcatg taggcggtta tgtaagcctg   600
atgtgaaatc ctggggctta accccagaat agcattgggt actgtgtaac ttgaattacg    660
gaagggaaac tggaattcca agtgtagggg tggaatctgt agatatttgg aagaacaccg    720
gtggcgaagg cgggtttctg gccgataatt gacgctgaga tgcgaaagtg tggggatcga    780
acaggattag ataccctggt agtccacacc gtaaacgatg tacactaggt gttggggcaa    840
gagcttcagt gccaaagcaa acgcgataag tgtaccgcct ggggagtatg cccgcaaggg    900
tgaaactcaa aggaattgac ggggcccgc acaagcggtg gagcatgtgg tttaattcga    960
tggtacgcga ggaaccttac ctgggtttga catctagtag aaggtcttag agataaggcc   1020
gggtagcaat accctgctag acaggtgctg catggctgtc gtcagctcgt gccgtgaggt   1080
gttgggttaa gtcccgcaat gagcgcaacc cctactgcca gttactaaca ggtaaagctt   1140
gaggactctg gcggaactgc cgatgacaaa tcggaggaag tggggatga cgtcaagtca    1200 tcatggccct tatgtccagg gctacacacg tgctacaatg gttgctacaa agcgaagcaa   1260
gaccgtaagg tggagcaagc cgcaaaaaag caatcgtagt tcggattgaa gtctgaaact   1320
cgacttcatg aagttggaat cgctagtaat cgcgcatcag cacggcgcgg tgaatacgtt   1380
cccgggcctt gtacacaccg cccgtcacac catccgagtt gggggtaccc gaagtcgctt   1440
gtctaacctg caaaggagga cggtgccgaa ggtacgcttg gtaaggaggg tgaagtcgta   1500
acaaggtagc cgtaccggaa ggtgcggctg gatcacctcc ttaa                    1544
```

<210> SEQ ID NO 11
<211> LENGTH: 1548
<212> TYPE: DNA
<213> ORGANISM: Chlamydia trachomatis

<400> SEQUENCE: 11

```
ctgagaattt gatcttggtt cagattgaac gctggcggcg tggatgaggc atgcaagtcg     60
aacggagcaa ttgtttcggc aattgtttag tggcggaagg gttagtaatg catagataat    120
ttgtccttaa cttgggaata acggttggaa acggccgcta ataccgaatg tggcgatatt    180
tgggcatccg agtaacgtta aagaagggga tcttaggacc tttcggttaa gggagagtct    240
atgtgatatc agctagttgg tggggtaaag gcctaccaag gctatgacgt ctaggcggat    300
tgagagattg gccgccaaca ctgggactga gacactgccc agactcctac gggaggctgc    360
agtcgagaat ctttcgcaat ggacggaagt ctgacgaagc gacgccgcgt gtgtgatgaa    420
ggctctaggg ttgtaaagca ctttcgcttg gaataagag aagacggtta ataccgctg     480 gatttgagcg taccaggtaa agaagcaccg gctaactccg tgccagcagc tgcggtaata    540
cggagggtgc tagcgttaat cggatttatt ggcgtaaag gccgtgtagg cggaaaggta    600
agttagttgt caaagatcgg ggctcaaccc cgagtcggca tctaatacta tttttctaga    660
gggtagatgg agaaaaggga atttcacgtg tagcggtgaa atgcgtagat atgtggaaga    720
acaccagtgg cgaaggcgct tttctaattt ataccgacg ctaaggcgcg aaagcaaggg    780
gagcaaacag gattagatac cctggtagtc cttgccgtaa acgatgcata cttgatgtgg    840
atggtctcaa ccccatccgt gtcggagcta acgcgttaag tatgccgcct gaggagtaca    900
ctcgcaaggg tgaaactcaa aagaattgac ggggcccgc acaagcagtg gagcatgtgg    960
tttaattcga tgcaacgcga aggaccttac ctgggtttga catgtatatg accgcggcag   1020
```

-continued

```
aaatgtcgtt ttccgcaagg acatatacac aggtgctgca tggctgtcgt cagctcgtgc    1080
cgtgaggtgt tgggttaagt cccgcaacga gcgcaaccct tatcgttagt tgccagcact    1140
tagggtggga actctaacga gactgcctgg gttaaccagg aggaaggcga ggatgacgtc    1200
aagtcagcat ggcccttatg cccagggcga cacacgtgct acaatggcca gtacagaagg    1260
tagcaagatc gtgagatgga gcaaatcctc aaagctggcc ccagttcgga ttgtagtctg    1320
caactcgact acatgaagtc ggaattgcta gtaatgcgct gtcagccata acgccgtgaa    1380
tacgttcccg ggccttgtac acaccgcccg tcacatcatg ggagttggtt ttaccttaag    1440
tcgttgactc aacccgcaag gagagaggcg cccaaggtga ggctgatgac taggatgaag    1500
tcgtaacaag gtagccctac cggaaggtgg ggctggatca cctcctttt               1548
```

<210> SEQ ID NO 12
<211> LENGTH: 1466
<212> TYPE: DNA
<213> ORGANISM: Bartonella henselae
<220> FEATURE:
<221> NAME/KEY: misc_feature
<222> LOCATION: (1)...(1466)
<223> OTHER INFORMATION: n = A,T,C or G

<400> SEQUENCE: 12

```
tcctggctca ggatgaacgc tggcggcagg cttaacacat gcaagtcgag cgcactcatt      60
tagagtgagc ggcagacggg tgagtaacgc gtgggaatct accctttcct acggaataac     120
acagagaaat ttgtgctaat accgtatacg tcctactgga gaaagattta tcggagaagg     180
atgagcccgc gttggattag ctagttggtg aggtaaaggc tcaccaaggc gacgatccat     240
agctggtctg agaggatgat cagccacact gggactgaga cacggcccag actcctacgg     300
gaggcagcag tggggaatat tggacaatgg gggcaaccct gatccagcca tgccgcgtga     360
gtgatgaagg ccctagggtt gtaaagctct ttcaccggtg aagataatga cggtaaccgg     420
agaagaagcc ccggctaact tcgtgccagc agccgcggta atacgaaggg ggctagcgtt     480
gttcggattt actgggcgta aagcgcatgt aggcggatat ttaagtcaga ggtgaaatcc     540
cagggctcaa ccctggaact gcctttgata ctggatatct tgagtatgga agaggtgagt     600
ggaattccga gtgtagaggt aaaattcgta gatattcgga ggaacaccag tggcgaaggc     660
ggctcactgg tccattactg acgctgaggt gcgaaagcgt ggggagcaaa caggattaga     720
taccctggta gtccacgccg taaacgatga atgttagccg ttgggtggtt tactgctcag     780
tggcgcacgt aacgcattaa acattccgcc tggggagtac ggtcgcaaga ttaaaactca     840
aaggaattga cggggcccg cacaagcggt ggagcatgtg gtttaattcg aagcaacgcg     900
cagaacctta ccagcccttg acatcccgat cgcgggaagt ggagacaccc tccttcagtt     960
cggctggatc ggagacaggt gctgcatggc tgtcgtcagc tcgtgtcgtg agatgttggg    1020
ttaagtcccg caacgagcgc aaccctcgcc cttagttgcc agcattcagt tgggcactct    1080
agggggactg ccggtgataa gccgagagga aggtggggat gacgtcaagt cctcatggcc    1140
cttacgggct gggctacaca cgtgctacaa tggtggtgac agtgggcagc gagatcgcaa    1200
ggtcgagcta atctccaaaa gccatctcag ttcggattgc actctgcaac tcgagtgcat    1260
gaagttggaa tcgctagtaa tcgtggatca gcatgctacg gtgaatacgt ncccgggcct    1320
tgtacacacc gcccgtcaca ccatgggagt tggttttacc cgaaggtgct gtgctaaccg    1380
caaggaggca ggtaaccacg gtagggtcag cgactggggt gaagtcgtaa caaggtagcc    1440
```

-continued

```
gtagggaacc tgcggctgga tcacct                                         1466
```

<210> SEQ ID NO 13
<211> LENGTH: 1487
<212> TYPE: DNA
<213> ORGANISM: Hemophilis influenza
<220> FEATURE:
<221> NAME/KEY: misc_feature
<222> LOCATION: (1)...(1487)
<223> OTHER INFORMATION: n = A,T,C or G

<400> SEQUENCE: 13

```
naattgaaga gttttgatcat ggctcagatt gaacgctggc ggcaggctta acacatgcaa     60
gtcgaacggt agcaggagaa agcttgcttt cttgctgacg agtggcggac gggtgagtaa    120
tgcttgggaa tctggcttat ggaggggggat aacgacggga aactgtcgct aataccgcgt    180
attatcggaa gatgaaagtg cgggactgag aggccgcatg ccataggatg agcccaagtg    240
ggattaggta gttggtgggg taaatgccta ccaagcctgc gatctctagc tggtctgaga    300
ggatgaccag ccacactgga actgagacac ggtccagact cctacgggag gcagcagtgg    360
ggaatattgc gcnatggggg gaaccctgac gcagccatgc cgcgtgaatg aagaaggcct    420
tcgggttgta aagttctttc ggtattgagg aaggttgatg tgttaatagc acatcaaatt    480
gacgttaaat acagaagaag caccggctaa ctccgtgcca gcagccgcgg taatacggag    540
ngtgcgagcg ttaatcggaa taactgggcg taaagggcac gcaggcggtt atttaagtga    600
ggtgtgaaag ccccgggctt aacctgggna ttgcatttca gactgggtaa ctagagtact    660
ttagggaggg gtagaattcc acgtgtagcg gtgaaatgcg tagagatgtg gaggaatacc    720
gaaggcgaag gcagccccctt gggaatgtac tgacgctcat gtgcgaaagc gtgggagca    780
aacaggatta gataccctgg tagtccacgc tgtaaacgct gtcgatttgg gggttggggt    840
ttaactctgg cacccgtagc taacgtgata aatcgaccgc ctggggagta cggccgcaag    900
gttaaaactc aaatgaattg acggggggccn gcacaagcgg tggagcatgt ggtttaattc    960
gatgcaacgc gaagaaccctt acctactctt gacatcctaa gaagagctca gagatgagct   1020
tgtgccttcg ggaacttaga gacaggtgct gcatggctgt cgtcagctcg tgttgtgaaa   1080
tgttgggtta agtcccgcaa cgagcgcaac ccttatcctt tgttgccagc gacttggtcg   1140
ggaactcaaa ggagactgcc agtgataaac tggaggaagg tngggatgac gtcaagtcat   1200
catggcccctt acgagtaggg ctacacacgt gctacaatgg cgtatacaga gggaagcgaa   1260
gctgcgaggt ggagcgaatc tcataaagta cgtctaagtc cggattggag tctgcaactc   1320
gactccatga agtcggaatc gctagtaatc gcgaatcaga atgtcgcggt gaatacgttc   1380
ccgggcnttg tacacaccgc ccgtcacacc atgggagtgg gttgtaccag aagtagatag   1440
cttaaccttt tggagggcgt ttaccacggt atgattcatg actgggg               1487
```

<210> SEQ ID NO 14
<211> LENGTH: 1487
<212> TYPE: DNA
<213> ORGANISM: Shigella dysenterae

<400> SEQUENCE: 14

```
tggctcagat tgaacgctgg cggcaggcct aacacatgca agtcgaacgg taacagaaag     60
cagcttgctg tttgctgacg agtggcggac gggtgagtaa tgtctgggaa actgcctgat    120
ggaggggggat aactactgga aacggtagct aataccgcat aacgtcgcaa gaccaaagag    180
ggggaccttc gggcctcttg ccatcggatg tgcccagatg ggattagcta gtaggtgggg    240
```

```
taacggctca cctaggcgac gatccctagc tggtctgaga ggatgaccag ccacactgga      300
actgagacac ggtccagact cctacgggag gcagcagtgg ggaatattgc acaatgggcg      360
caagcctgat gcagccatgc cgcgtgtatg aagaaggcct tcgggttgta aagtactttc      420
agcggggagg aagggagtaa agttaatacc tttgctcatt gacgttaccc gcagaagaag      480
caccggctaa ctccgtgcca gcagccgcgg taatacggag ggtgcaagcg ttaatcggaa      540
ttactgggcg taaagcgcac gcaggcggtt tgttaagtca gatgtgaaat ccccgggctc      600
aacctgggaa ctgcatctga tactggcaag cttgagtctc gtagaggggg gtagaattcc      660
aggtgtagcg gtgaaatgcg tagagatctg gaggaatacc ggtggcgaag gcggccccct      720
ggacgaaaac tgacgctcag gtgcgaaagc gtggggagca acaggatta gataccctgg       780 tagtccacgc cgtaaacgat gtcgacttgg aggttgtgcc cttgaggcgt ggcttccgga      840
gctaacgcgt taagtcgacc gcctggggag tacggccgca aggttaaaac tcaaatgaat      900 tgacggggc ccgcacaagc ggtggagcat gtggtttaat tcgatgcaac gcgaagaacc       960
ttacctggtc ttgacatcca cagaaccttg tagagatacg agggtgcctt cgggaactgt     1020
gagacaggtg ctgcatggct gtcgtcagct cgtgttgtga atgttgggt taagtcccgc      1080 aacgagcgca acccttatcc tttgttgcca gcggtccggc cgggaactca aggagactg      1140 ccagtgataa actggaggaa ggtggggatg acgtcaagtc atcatggccc ttacgaccag     1200
ggctacacac gtgctacaat ggcgcataca agagaagcg acctcgcgag agcaagcgga      1260
cctcataaag tgcgtcgtag tccggattgg agtctgcaac tcgactccat gaagtcggaa     1320
tcgctagtaa tcgtggatca gaatgtcacg gtgaatacgt tcccgggcct tgtacacacc     1380
gcccgtcaca ccatgggagt gggttgcaaa agaagtaggt agcttaacct tcgggagggc     1440
gcttaccact ttgtgattca tgactggggt gaagtcgtaa caaggta                   1487

<210> SEQ ID NO 15
<211> LENGTH: 22
<212> TYPE: DNA
<213> ORGANISM: Artificial Sequence
<220> FEATURE:
<223> OTHER INFORMATION: antisense oligomer

<400> SEQUENCE: 15
ggactacgac gcactttatg ag                                                22

<210> SEQ ID NO 16
<211> LENGTH: 21
<212> TYPE: DNA
<213> ORGANISM: Artificial Sequence
<220> FEATURE:
<223> OTHER INFORMATION: antisense oligomer

<400> SEQUENCE: 16
ggtccgcttg ctctcgcgag g                                                 21

<210> SEQ ID NO 17
<211> LENGTH: 21
<212> TYPE: DNA
<213> ORGANISM: Artificial Sequence
<220> FEATURE:
<223> OTHER INFORMATION: antisense oligomer

<400> SEQUENCE: 17
gcaaaggtat taactttact c                                                 21
```

<210> SEQ ID NO 18
<211> LENGTH: 21
<212> TYPE: DNA
<213> ORGANISM: Artificial Sequence
<220> FEATURE:
<223> OTHER INFORMATION: antisense oligomer

<400> SEQUENCE: 18
gctgcggtta ttaaccacaa c                                    21

<210> SEQ ID NO 19
<211> LENGTH: 21
<212> TYPE: DNA
<213> ORGANISM: Artificial Sequence
<220> FEATURE:
<223> OTHER INFORMATION: antisense oligomer

<400> SEQUENCE: 19
gcactttatg aggtccgctt g                                    21

<210> SEQ ID NO 20
<211> LENGTH:
<212> TYPE:
<213> ORGANISM:
<220> FEATURE:
<223> OTHER INFORMATION: No sequence is present

<400> SEQUENCE: 20

000

<210> SEQ ID NO 21
<211> LENGTH: 21
<212> TYPE: DNA
<213> ORGANISM: Artificial Sequence
<220> FEATURE:
<223> OTHER INFORMATION: antisense oligomer

<400> SEQUENCE: 21
tgctgcctcc cgtaggagtc t                                    21

<210> SEQ ID NO 22
<211> LENGTH: 21
<212> TYPE: DNA
<213> ORGANISM: Artificial Sequence
<220> FEATURE:
<223> OTHER INFORMATION: antisense oligomer

<400> SEQUENCE: 22
attaccgcgg ctgctggcac g                                    21

<210> SEQ ID NO 23
<211> LENGTH: 21
<212> TYPE: DNA
<213> ORGANISM: Artificial Sequence
<220> FEATURE:
<223> OTHER INFORMATION: antisense oligomer

<400> SEQUENCE: 23
accagggtat ctaatcctgt t                                    21

<210> SEQ ID NO 24
<211> LENGTH: 21
<212> TYPE: DNA
<213> ORGANISM: Artificial Sequence
<220> FEATURE:
<223> OTHER INFORMATION: antisense oligomer

```
<400> SEQUENCE: 24
cacatgctcc accgcttgtg c                                              21

<210> SEQ ID NO 25
<211> LENGTH: 21
<212> TYPE: DNA
<213> ORGANISM: Artificial Sequence
<220> FEATURE:
<223> OTHER INFORMATION: antisense oligomer

<400> SEQUENCE: 25
ttgcgggact taacccaaca t                                              21

<210> SEQ ID NO 26
<211> LENGTH:
<212> TYPE:
<213> ORGANISM:
<220> FEATURE:
<223> OTHER INFORMATION: No sequence is present

<400> SEQUENCE: 26

000

<210> SEQ ID NO 27
<211> LENGTH: 21
<212> TYPE: DNA
<213> ORGANISM: Artificial Sequence
<220> FEATURE:
<223> OTHER INFORMATION: antisense oligomer

<400> SEQUENCE: 27
cgcggctgct ggcacgtagt t                                              21

<210> SEQ ID NO 28
<211> LENGTH: 21
<212> TYPE: DNA
<213> ORGANISM: Artificial Sequence
<220> FEATURE:
<223> OTHER INFORMATION: antisense oligomer

<400> SEQUENCE: 28
acttaaccca acatctcacg a                                              21

<210> SEQ ID NO 29
<211> LENGTH: 20
<212> TYPE: DNA
<213> ORGANISM: Artificial Sequence
<220> FEATURE:
<223> OTHER INFORMATION: antisense oligomer

<400> SEQUENCE: 29
tttacgccca gtaattccga                                                20

<210> SEQ ID NO 30
<211> LENGTH: 22
<212> TYPE: DNA
<213> ORGANISM: Artificial Sequence
<220> FEATURE:
<223> OTHER INFORMATION: antisense oligomer

<400> SEQUENCE: 30
actcccatgg tgtgacgggc gg                                             22

<210> SEQ ID NO 31
```

```
<211> LENGTH: 21
<212> TYPE: DNA
<213> ORGANISM: Artificial Sequence
<220> FEATURE:
<223> OTHER INFORMATION: antisense oligomer

<400> SEQUENCE: 31
aatctgagcc atgatcaaac t                                              21

<210> SEQ ID NO 32
<211> LENGTH: 21
<212> TYPE: DNA
<213> ORGANISM: Artificial Sequence
<220> FEATURE:
<223> OTHER INFORMATION: antisense oligomer

<400> SEQUENCE: 32
ccctctttgt gcttgcgacg t                                              21

<210> SEQ ID NO 33
<211> LENGTH: 21
<212> TYPE: DNA
<213> ORGANISM: Artificial Sequence
<220> FEATURE:
<223> OTHER INFORMATION: antisense oligomer

<400> SEQUENCE: 33
acccccctct acgagactca a                                              21

<210> SEQ ID NO 34
<211> LENGTH: 21
<212> TYPE: DNA
<213> ORGANISM: Artificial Sequence
<220> FEATURE:
<223> OTHER INFORMATION: antisense oligomer

<400> SEQUENCE: 34
ccacgcctca agggcacaac c                                              21

<210> SEQ ID NO 35
<211> LENGTH: 21
<212> TYPE: DNA
<213> ORGANISM: Artificial Sequence
<220> FEATURE:
<223> OTHER INFORMATION: antisense oligomer

<400> SEQUENCE: 35
tctcatctct gaaaacttcc g                                              21

<210> SEQ ID NO 36
<211> LENGTH: 21
<212> TYPE: DNA
<213> ORGANISM: Artificial Sequence
<220> FEATURE:
<223> OTHER INFORMATION: antisense oligomer

<400> SEQUENCE: 36
catgatcaaa ctcttcaatt t                                              21

<210> SEQ ID NO 37
<211> LENGTH: 21
<212> TYPE: DNA
<213> ORGANISM: Artificial Sequence
<220> FEATURE:
<223> OTHER INFORMATION: antisense oligomer

<400> SEQUENCE: 37
```
ccctctttgg tcttgcgacg t                                                    21

<210> SEQ ID NO 38
<211> LENGTH: 21
<212> TYPE: DNA
<213> ORGANISM: Artificial Sequence
<220> FEATURE:
<223> OTHER INFORMATION: antisense oligomer

<400> SEQUENCE: 38
tacccccctc tacgagactc a                                                    21

<210> SEQ ID NO 39
<211> LENGTH: 21
<212> TYPE: DNA
<213> ORGANISM: Artificial Sequence
<220> FEATURE:
<223> OTHER INFORMATION: antisense oligomer

<400> SEQUENCE: 39
gccacgcctc aagggcacaa c                                                    21

<210> SEQ ID NO 40
<211> LENGTH: 21
<212> TYPE: DNA
<213> ORGANISM: Artificial Sequence
<220> FEATURE:
<223> OTHER INFORMATION: antisense oligomer

<400> SEQUENCE: 40
cagagagcaa gccctcttca t                                                    21

<210> SEQ ID NO 41
<211> LENGTH: 21
<212> TYPE: DNA
<213> ORGANISM: Artificial Sequence
<220> FEATURE:
<223> OTHER INFORMATION: antisense oligomer

<400> SEQUENCE: 41
cctgctttct cccgtaggac g                                                    21

<210> SEQ ID NO 42
<211> LENGTH: 21
<212> TYPE: DNA
<213> ORGANISM: Artificial Sequence
<220> FEATURE:
<223> OTHER INFORMATION: antisense oligomer

<400> SEQUENCE: 42
caccaccctc tgccatactc t                                                    21

<210> SEQ ID NO 43
<211> LENGTH: 21
<212> TYPE: DNA
<213> ORGANISM: Artificial Sequence
<220> FEATURE:
<223> OTHER INFORMATION: antisense oligomer

<400> SEQUENCE: 43
ctaagatctc aaggatccca a                                                    21

<210> SEQ ID NO 44
<211> LENGTH: 21
<212> TYPE: DNA

```
<213> ORGANISM: Artificial Sequence
<220> FEATURE:
<223> OTHER INFORMATION: antisense oligomer

<400> SEQUENCE: 44
ggcctgccgc cagcgttcaa t                                              21

<210> SEQ ID NO 45
<211> LENGTH: 21
<212> TYPE: DNA
<213> ORGANISM: Artificial Sequence
<220> FEATURE:
<223> OTHER INFORMATION: antisense oligomer

<400> SEQUENCE: 45
ccctctttgg tccgtaaaca t                                              21

<210> SEQ ID NO 46
<211> LENGTH: 21
<212> TYPE: DNA
<213> ORGANISM: Artificial Sequence
<220> FEATURE:
<223> OTHER INFORMATION: antisense oligomer

<400> SEQUENCE: 46 cccccctctac aagactctag c                                             21

<210> SEQ ID NO 47
<211> LENGTH: 21
<212> TYPE: DNA
<213> ORGANISM: Artificial Sequence
<220> FEATURE:
<223> OTHER INFORMATION: antisense oligomer

<400> SEQUENCE: 47
acgactytag gtcacaacct c                                              21

<210> SEQ ID NO 48
<211> LENGTH: 21
<212> TYPE: DNA
<213> ORGANISM: Artificial Sequence
<220> FEATURE:
<223> OTHER INFORMATION: antisense oligomer

<400> SEQUENCE: 48
aggatcaaac tcttatgttc a                                              21

<210> SEQ ID NO 49
<211> LENGTH: 21
<212> TYPE: DNA
<213> ORGANISM: Artificial Sequence
<220> FEATURE:
<223> OTHER INFORMATION: antisense oligomer

<400> SEQUENCE: 49
cctgctttcc ctctcaagac g                                              21

<210> SEQ ID NO 50
<211> LENGTH: 21
<212> TYPE: DNA
<213> ORGANISM: Artificial Sequence
<220> FEATURE:
<223> OTHER INFORMATION: antisense oligomer

<400> SEQUENCE: 50
cacctccctc tgacacactc g                                              21
```

<210> SEQ ID NO 51
<211> LENGTH: 21
<212> TYPE: DNA
<213> ORGANISM: Artificial Sequence
<220> FEATURE:
<223> OTHER INFORMATION: antisense oligomer

<400> SEQUENCE: 51
ccaagcaatc aagttgccca a                                              21

<210> SEQ ID NO 52
<211> LENGTH: 21
<212> TYPE: DNA
<213> ORGANISM: Artificial Sequence
<220> FEATURE:
<223> OTHER INFORMATION: antisense oligomer

<400> SEQUENCE: 52
ccagcgttca tcctgagcca g                                              21

<210> SEQ ID NO 53
<211> LENGTH: 21
<212> TYPE: DNA
<213> ORGANISM: Artificial Sequence
<220> FEATURE:
<223> OTHER INFORMATION: antisense oligomer

<400> SEQUENCE: 53
gaaccatgcg gttcaaaata t                                              21

<210> SEQ ID NO 54
<211> LENGTH: 21
<212> TYPE: DNA
<213> ORGANISM: Artificial Sequence
<220> FEATURE:
<223> OTHER INFORMATION: antisense oligomer

<400> SEQUENCE: 54
ctttcctctt ctgcactcaa g                                              21

<210> SEQ ID NO 55
<211> LENGTH: 21
<212> TYPE: DNA
<213> ORGANISM: Artificial Sequence
<220> FEATURE:
<223> OTHER INFORMATION: antisense oligomer

<400> SEQUENCE: 55
ggggcggaaa cccccctaaca c                                             21

<210> SEQ ID NO 56
<211> LENGTH: 21
<212> TYPE: DNA
<213> ORGANISM: Artificial Sequence
<220> FEATURE:
<223> OTHER INFORMATION: antisense oligomer

<400> SEQUENCE: 56
gcatgtgtta agcacgccgc c                                              21

<210> SEQ ID NO 57
<211> LENGTH: 21
<212> TYPE: DNA
<213> ORGANISM: Artificial Sequence
<220> FEATURE:

```
<223> OTHER INFORMATION: antisense oligomer

<400> SEQUENCE: 57
aagacatgca tcccgtggtc c                                              21

<210> SEQ ID NO 58
<211> LENGTH: 21
<212> TYPE: DNA
<213> ORGANISM: Artificial Sequence
<220> FEATURE:
<223> OTHER INFORMATION: antisense oligomer

<400> SEQUENCE: 58
cagtctcccc tgcagtactc t                                              21

<210> SEQ ID NO 59
<211> LENGTH: 21
<212> TYPE: DNA
<213> ORGANISM: Artificial Sequence
<220> FEATURE:
<223> OTHER INFORMATION: antisense oligomer

<400> SEQUENCE: 59
gatcccaagg aaggaaaccc a                                              21

<210> SEQ ID NO 60
<211> LENGTH: 21
<212> TYPE: DNA
<213> ORGANISM: Artificial Sequence
<220> FEATURE:
<223> OTHER INFORMATION: antisense oligomer

<400> SEQUENCE: 60
caggatcaaa ctctccataa a                                              21

<210> SEQ ID NO 61
<211> LENGTH: 21
<212> TYPE: DNA
<213> ORGANISM: Artificial Sequence
<220> FEATURE:
<223> OTHER INFORMATION: antisense oligomer

<400> SEQUENCE: 61
aaatctttcc cccgtaggag t                                              21

<210> SEQ ID NO 62
<211> LENGTH: 21
<212> TYPE: DNA
<213> ORGANISM: Artificial Sequence
<220> FEATURE:
<223> OTHER INFORMATION: antisense oligomer

<400> SEQUENCE: 62
cacctacctc tcccacactc t                                              21

<210> SEQ ID NO 63
<211> LENGTH: 21
<212> TYPE: DNA
<213> ORGANISM: Artificial Sequence
<220> FEATURE:
<223> OTHER INFORMATION: antisense oligomer

<400> SEQUENCE: 63
tggagagact aagccctcca a                                              21
```

```
<210> SEQ ID NO 64
<211> LENGTH: 21
<212> TYPE: DNA
<213> ORGANISM: Artificial Sequence
<220> FEATURE:
<223> OTHER INFORMATION: antisense oligomer

<400> SEQUENCE: 64
cgtcctgagc caggatcaaa t                                              21

<210> SEQ ID NO 65
<211> LENGTH: 21
<212> TYPE: DNA
<213> ORGANISM: Artificial Sequence
<220> FEATURE:
<223> OTHER INFORMATION: antisense oligomer

<400> SEQUENCE: 65
atgtcatgca acatccactc t                                              21

<210> SEQ ID NO 66
<211> LENGTH: 21
<212> TYPE: DNA
<213> ORGANISM: Artificial Sequence
<220> FEATURE:
<223> OTHER INFORMATION: antisense oligomer

<400> SEQUENCE: 66
actctcccct cttgcactca a                                              21

<210> SEQ ID NO 67
<211> LENGTH: 21
<212> TYPE: DNA
<213> ORGANISM: Artificial Sequence
<220> FEATURE:
<223> OTHER INFORMATION: antisense oligomer

<400> SEQUENCE: 67
aaaccccgga aagggtctaa c                                              21

<210> SEQ ID NO 68
<211> LENGTH: 21
<212> TYPE: DNA
<213> ORGANISM: Artificial Sequence
<220> FEATURE:
<223> OTHER INFORMATION: antisense oligomer

<400> SEQUENCE: 68
tctgagccat gatcaaactc t                                              21

<210> SEQ ID NO 69
<211> LENGTH: 21
<212> TYPE: DNA
<213> ORGANISM: Artificial Sequence
<220> FEATURE:
<223> OTHER INFORMATION: antisense oligomer

<400> SEQUENCE: 69
accccttatg aagcactgag t                                              21

<210> SEQ ID NO 70
<211> LENGTH: 21
<212> TYPE: DNA
<213> ORGANISM: Artificial Sequence
<220> FEATURE:
<223> OTHER INFORMATION: antisense oligomer
```

```
<400> SEQUENCE: 70
agtttccctt ccgtaattca a                                              21

<210> SEQ ID NO 71
<211> LENGTH: 21
<212> TYPE: DNA
<213> ORGANISM: Artificial Sequence
<220> FEATURE:
<223> OTHER INFORMATION: antisense oligomer

<400> SEQUENCE: 71
cactgaagct cttgccccaa c                                              21

<210> SEQ ID NO 72
<211> LENGTH: 21
<212> TYPE: DNA
<213> ORGANISM: Artificial Sequence
<220> FEATURE:
<223> OTHER INFORMATION: antisense oligomer

<400> SEQUENCE: 72
gaaccaagat caaattctca g                                              21

<210> SEQ ID NO 73
<211> LENGTH: 21
<212> TYPE: DNA
<213> ORGANISM: Artificial Sequence
<220> FEATURE:
<223> OTHER INFORMATION: antisense oligomer

<400> SEQUENCE: 73
gttactcgga tgcccaaata t                                              21

<210> SEQ ID NO 74
<211> LENGTH: 21
<212> TYPE: DNA
<213> ORGANISM: Artificial Sequence
<220> FEATURE:
<223> OTHER INFORMATION: antisense oligomer

<400> SEQUENCE: 74 cctttctctcc atctaccctc t                                             21

<210> SEQ ID NO 75
<211> LENGTH: 21
<212> TYPE: DNA
<213> ORGANISM: Artificial Sequence
<220> FEATURE:
<223> OTHER INFORMATION: antisense oligomer

<400> SEQUENCE: 75
ggatggggtt gagaccatcc a                                              21

<210> SEQ ID NO 76
<211> LENGTH: 21
<212> TYPE: DNA
<213> ORGANISM: Artificial Sequence
<220> FEATURE:
<223> OTHER INFORMATION: antisense oligomer

<400> SEQUENCE: 76
agcgttcatc ctgagccagg a                                              21

<210> SEQ ID NO 77
<211> LENGTH: 21
```

```
<212> TYPE: DNA
<213> ORGANISM: Artificial Sequence
<220> FEATURE:
<223> OTHER INFORMATION: antisense oligomer

<400> SEQUENCE: 77
aaatctttct ccagtaggac g                                              21

<210> SEQ ID NO 78
<211> LENGTH: 21
<212> TYPE: DNA
<213> ORGANISM: Artificial Sequence
<220> FEATURE:
<223> OTHER INFORMATION: antisense oligomer

<400> SEQUENCE: 78
cactcacctc ttccatactc a                                              21

<210> SEQ ID NO 79
<211> LENGTH: 21
<212> TYPE: DNA
<213> ORGANISM: Artificial Sequence
<220> FEATURE:
<223> OTHER INFORMATION: antisense oligomer

<400> SEQUENCE: 79
actgagcagt aaaccaccca a                                              21

<210> SEQ ID NO 80
<211> LENGTH: 21
<212> TYPE: DNA
<213> ORGANISM: Artificial Sequence
<220> FEATURE:
<223> OTHER INFORMATION: antisense oligomer
<220> FEATURE:
<221> NAME/KEY: misc_feature
<222> LOCATION: (1)...(21)
<223> OTHER INFORMATION: n = A,T,C or G

<400> SEQUENCE: 80
catgatcaaa ctcttcaatt n                                              21

<210> SEQ ID NO 81
<211> LENGTH: 21
<212> TYPE: DNA
<213> ORGANISM: Artificial Sequence
<220> FEATURE:
<223> OTHER INFORMATION: antisense oligomer

<400> SEQUENCE: 81
cactttcatc ttccgataat a                                              21

<210> SEQ ID NO 82
<211> LENGTH: 21
<212> TYPE: DNA
<213> ORGANISM: Artificial Sequence
<220> FEATURE:
<223> OTHER INFORMATION: antisense oligomer

<400> SEQUENCE: 82
cctccctaaa gtactctagt t                                              21

<210> SEQ ID NO 83
<211> LENGTH: 21
<212> TYPE: DNA
<213> ORGANISM: Artificial Sequence
<220> FEATURE:
```

<223> OTHER INFORMATION: antisense oligomer

<400> SEQUENCE: 83
cagagttaaa ccccaacccc c                                    21

<210> SEQ ID NO 84
<211> LENGTH: 21
<212> TYPE: DNA
<213> ORGANISM: Artificial Sequence
<220> FEATURE:
<223> OTHER INFORMATION: antisense oligomer

<400> SEQUENCE: 84
gccagcgttc aatctgagcc a                                    21

<210> SEQ ID NO 85
<211> LENGTH: 21
<212> TYPE: DNA
<213> ORGANISM: Artificial Sequence
<220> FEATURE:
<223> OTHER INFORMATION: antisense oligomer

<400> SEQUENCE: 85
ccctctttgg tcttgcgacg t                                    21

<210> SEQ ID NO 86
<211> LENGTH: 21
<212> TYPE: DNA
<213> ORGANISM: Artificial Sequence
<220> FEATURE:
<223> OTHER INFORMATION: antisense oligomer

<400> SEQUENCE: 86 taccccctc tacgagactc a                                     21

<210> SEQ ID NO 87
<211> LENGTH: 21
<212> TYPE: DNA
<213> ORGANISM: Artificial Sequence
<220> FEATURE:
<223> OTHER INFORMATION: antisense oligomer

<400> SEQUENCE: 87
gccacgcctc aagggcacaa c                                    21

<210> SEQ ID NO 88
<211> LENGTH: 21
<212> TYPE: DNA
<213> ORGANISM: Artificial Sequence
<220> FEATURE:
<223> OTHER INFORMATION: antisense oligomer

<400> SEQUENCE: 88
cctcgtatct ctacaaggtt c                                    21

<210> SEQ ID NO 89
<211> LENGTH: 23
<212> TYPE: DNA
<213> ORGANISM: Artificial Sequence
<220> FEATURE:
<223> OTHER INFORMATION: antisense oligomer

<400> SEQUENCE: 89
ccccatcatt atgagtgatg tgc                                  23

<210> SEQ ID NO 90
<211> LENGTH: 19
<212> TYPE: DNA
<213> ORGANISM: Artificial Sequence
<220> FEATURE:
<223> OTHER INFORMATION: antisense oligomer

<400> SEQUENCE: 90
tcattatgag gtgacccca                                                19

<210> SEQ ID NO 91
<211> LENGTH: 20
<212> TYPE: DNA
<213> ORGANISM: Artificial Sequence
<220> FEATURE:
<223> OTHER INFORMATION: antisense oligomer

<400> SEQUENCE: 91
gatgaacagt tactctcatc                                               20

<210> SEQ ID NO 92
<211> LENGTH: 20
<212> TYPE: DNA
<213> ORGANISM: Artificial Sequence
<220> FEATURE:
<223> OTHER INFORMATION: antisense oligomer

<400> SEQUENCE: 92
actgagagaa gctttaagag                                               20

<210> SEQ ID NO 93
<211> LENGTH: 20
<212> TYPE: DNA
<213> ORGANISM: Artificial Sequence
<220> FEATURE:
<223> OTHER INFORMATION: antisense oligomer

<400> SEQUENCE: 93
atgtgcacag ttacttacac                                               20

<210> SEQ ID NO 94
<211> LENGTH: 20
<212> TYPE: DNA
<213> ORGANISM: Artificial Sequence
<220> FEATURE:
<223> OTHER INFORMATION: antisense oligomer

<400> SEQUENCE: 94
ctgagaacaa ctttatggga                                               20

<210> SEQ ID NO 95
<211> LENGTH: 20
<212> TYPE: DNA
<213> ORGANISM: Artificial Sequence
<220> FEATURE:
<223> OTHER INFORMATION: antisense oligomer

<400> SEQUENCE: 95
ttattctgtt ggtaacgtca                                               20

<210> SEQ ID NO 96
<211> LENGTH: 19
<212> TYPE: DNA
<213> ORGANISM: Artificial Sequence
<220> FEATURE:
<223> OTHER INFORMATION: antisense oligomer

```
<400> SEQUENCE: 96
cgagttgcag actgcgatc                                                    19

<210> SEQ ID NO 97
<211> LENGTH: 20
<212> TYPE: DNA
<213> ORGANISM: Artificial Sequence
<220> FEATURE:
<223> OTHER INFORMATION: antisense oligomer

<400> SEQUENCE: 97
atctgagcca tgatcaaact                                                   20

<210> SEQ ID NO 98
<211> LENGTH: 20
<212> TYPE: DNA
<213> ORGANISM: Artificial Sequence
<220> FEATURE:
<223> OTHER INFORMATION: antisense oligomer

<400> SEQUENCE: 98
tgtctcagtt ccagtgttgc                                                   20

<210> SEQ ID NO 99
<211> LENGTH: 20
<212> TYPE: DNA
<213> ORGANISM: Artificial Sequence
<220> FEATURE:
<223> OTHER INFORMATION: antisense oligomer

<400> SEQUENCE: 99
gtcttcgtcc aggggccgc                                                    20

<210> SEQ ID NO 100
<211> LENGTH: 20
<212> TYPE: DNA
<213> ORGANISM: Artificial Sequence
<220> FEATURE:
<223> OTHER INFORMATION: antisense oligomer

<400> SEQUENCE: 100
cacctgtctc acggttcccg                                                   20

<210> SEQ ID NO 101
<211> LENGTH: 20
<212> TYPE: DNA
<213> ORGANISM: Artificial Sequence
<220> FEATURE:
<223> OTHER INFORMATION: antisense oligomer

<400> SEQUENCE: 101
cgccctcccg aagttaagct                                                   20

<210> SEQ ID NO 102
<211> LENGTH: 19
<212> TYPE: DNA
<213> ORGANISM: Artificial Sequence
<220> FEATURE:
<223> OTHER INFORMATION: antisense oligomer

<400> SEQUENCE: 102
ggcacgccgc cagcgttcg                                                    19

<210> SEQ ID NO 103
<211> LENGTH: 20
```

```
<212> TYPE: DNA
<213> ORGANISM: Artificial Sequence
<220> FEATURE:
<223> OTHER INFORMATION: antisense oligomer

<400> SEQUENCE: 103
tgtctcagtc ccaatgtggc                                              20

<210> SEQ ID NO 104
<211> LENGTH: 20
<212> TYPE: DNA
<213> ORGANISM: Artificial Sequence
<220> FEATURE:
<223> OTHER INFORMATION: antisense oligomer

<400> SEQUENCE: 104
gttacagacc agagagccgc                                              20

<210> SEQ ID NO 105
<211> LENGTH: 20
<212> TYPE: DNA
<213> ORGANISM: Artificial Sequence
<220> FEATURE:
<223> OTHER INFORMATION: antisense oligomer

<400> SEQUENCE: 105
cacctgtcac tttgcccccg                                              20

<210> SEQ ID NO 106
<211> LENGTH: 19
<212> TYPE: DNA
<213> ORGANISM: Artificial Sequence
<220> FEATURE:
<223> OTHER INFORMATION: antisense oligomer

<400> SEQUENCE: 106
ggcggctggc tccaaaagg                                               19

<210> SEQ ID NO 107
<211> LENGTH: 19
<212> TYPE: DNA
<213> ORGANISM: Artificial Sequence
<220> FEATURE:
<223> OTHER INFORMATION: antisense oligomer

<400> SEQUENCE: 107
cacccgttcg ccactcctc                                               19

<210> SEQ ID NO 108
<211> LENGTH: 20
<212> TYPE: DNA
<213> ORGANISM: Artificial Sequence
<220> FEATURE:
<223> OTHER INFORMATION: antisense oligomer

<400> SEQUENCE: 108
tcaattcctt tgagtttcaa                                              20

<210> SEQ ID NO 109
<211> LENGTH: 29
<212> TYPE: DNA
<213> ORGANISM: Artificial Sequence
<220> FEATURE:
<223> OTHER INFORMATION: antisense oligomer

<400> SEQUENCE: 109
```
gcaatccgaa ctgagagaag ctttaagag                29

<210> SEQ ID NO 110
<211> LENGTH: 24
<212> TYPE: DNA
<213> ORGANISM: Artificial Sequence
<220> FEATURE:
<223> OTHER INFORMATION: antisense oligomer

<400> SEQUENCE: 110
ccgaactgag agaagcttta agag                     24

<210> SEQ ID NO 111
<211> LENGTH: 17
<212> TYPE: DNA
<213> ORGANISM: Artificial Sequence
<220> FEATURE:
<223> OTHER INFORMATION: antisense oligomer

<400> SEQUENCE: 111
gagagaagct ttaagag                             17

<210> SEQ ID NO 112
<211> LENGTH: 15
<212> TYPE: DNA
<213> ORGANISM: Artificial Sequence
<220> FEATURE:
<223> OTHER INFORMATION: antisense oligomer

<400> SEQUENCE: 112
gagaagcttt aagag                               15

<210> SEQ ID NO 113
<211> LENGTH: 12
<212> TYPE: DNA
<213> ORGANISM: Artificial Sequence
<220> FEATURE:
<223> OTHER INFORMATION: antisense oligomer

<400> SEQUENCE: 113
aagctttaag ag                                  12

<210> SEQ ID NO 114
<211> LENGTH: 20
<212> TYPE: DNA
<213> ORGANISM: Artificial Sequence
<220> FEATURE:
<223> OTHER INFORMATION: antisense oligomer

<400> SEQUENCE: 114
gactaccagg gtatctaatc                          20

<210> SEQ ID NO 115
<211> LENGTH: 20
<212> TYPE: DNA
<213> ORGANISM: Artificial Sequence
<220> FEATURE:
<223> OTHER INFORMATION: antisense oligomer

<400> SEQUENCE: 115
cagcgacacc cgaaagcgcc                          20

<210> SEQ ID NO 116
<211> LENGTH: 20
<212> TYPE: DNA
<213> ORGANISM: Artificial Sequence

```
<220> FEATURE:
<223> OTHER INFORMATION: antisense oligomer

<400> SEQUENCE: 116
gtgccaaggc atccaccgtg                                                    20

<210> SEQ ID NO 117
<211> LENGTH: 20
<212> TYPE: DNA
<213> ORGANISM: Artificial Sequence
<220> FEATURE:
<223> OTHER INFORMATION: antisense oligomer

<400> SEQUENCE: 117
catactcaaa cgccctattc                                                    20

<210> SEQ ID NO 118
<211> LENGTH: 19
<212> TYPE: DNA
<213> ORGANISM: Artificial Sequence
<220> FEATURE:
<223> OTHER INFORMATION: antisense oligomer

<400> SEQUENCE: 118
ccttagcctc ctgcgtccc                                                     19

<210> SEQ ID NO 119
<211> LENGTH: 20
<212> TYPE: DNA
<213> ORGANISM: Artificial Sequence
<220> FEATURE:
<223> OTHER INFORMATION: antisense oligomer

<400> SEQUENCE: 119
ggggtctttc cgtcctgtcg                                                    20

<210> SEQ ID NO 120
<211> LENGTH: 20
<212> TYPE: DNA
<213> ORGANISM: Artificial Sequence
<220> FEATURE:
<223> OTHER INFORMATION: antisense oligomer

<400> SEQUENCE: 120
cgatcgatta gtatcagtcc                                                    20

<210> SEQ ID NO 121
<211> LENGTH: 18
<212> TYPE: DNA
<213> ORGANISM: Artificial Sequence
<220> FEATURE:
<223> OTHER INFORMATION: antisense oligomer

<400> SEQUENCE: 121
tgagagaagc tttaagag                                                      18

<210> SEQ ID NO 122
<211> LENGTH: 19
<212> TYPE: DNA
<213> ORGANISM: Artificial Sequence
<220> FEATURE:
<223> OTHER INFORMATION: antisense oligomer

<400> SEQUENCE: 122
ctgagagaag ctttaagag                                                     19
```

<210> SEQ ID NO 123
<211> LENGTH: 18
<212> TYPE: DNA
<213> ORGANISM: Artificial Sequence
<220> FEATURE:
<223> OTHER INFORMATION: antisense oligomer

<400> SEQUENCE: 123
gcgacacccg aaagcgcc                                                    18

<210> SEQ ID NO 124
<211> LENGTH: 18
<212> TYPE: DNA
<213> ORGANISM: Artificial Sequence
<220> FEATURE:
<223> OTHER INFORMATION: antisense oligomer

<400> SEQUENCE: 124
tacagaccag agagccgc                                                    18

<210> SEQ ID NO 125
<211> LENGTH: 17
<212> TYPE: DNA
<213> ORGANISM: Artificial Sequence
<220> FEATURE:
<223> OTHER INFORMATION: antisense oligomer

<400> SEQUENCE: 125
cgacacccga aagcgcc                                                     17

<210> SEQ ID NO 126
<211> LENGTH: 19
<212> TYPE: DNA
<213> ORGANISM: Artificial Sequence
<220> FEATURE:
<223> OTHER INFORMATION: antisense oligomer

<400> SEQUENCE: 126
agcgacaccc gaaagcgcc                                                   19

<210> SEQ ID NO 127
<211> LENGTH: 18
<212> TYPE: DNA
<213> ORGANISM: Artificial Sequence
<220> FEATURE:
<223> OTHER INFORMATION: antisense oligomer

<400> SEQUENCE: 127
cgacacccga aagcgcct                                                    18

<210> SEQ ID NO 128
<211> LENGTH: 17
<212> TYPE: DNA
<213> ORGANISM: Artificial Sequence
<220> FEATURE:
<223> OTHER INFORMATION: antisense oligomer

<400> SEQUENCE: 128
mgamammmga aagmgmm                                                     17

<210> SEQ ID NO 129
<211> LENGTH: 18
<212> TYPE: DNA
<213> ORGANISM: Artificial Sequence
<220> FEATURE:
<223> OTHER INFORMATION: antisense oligomer

<400> SEQUENCE: 129
tamagammag agagmmgm                                                    18

<210> SEQ ID NO 130
<211> LENGTH: 16
<212> TYPE: DNA
<213> ORGANISM: Artificial Sequence
<220> FEATURE:
<223> OTHER INFORMATION: antisense oligomer

<400> SEQUENCE: 130
mmmmammttm mtmmgg                                                      16

<210> SEQ ID NO 131
<211> LENGTH: 19
<212> TYPE: DNA
<213> ORGANISM: Artificial Sequence
<220> FEATURE:
<223> OTHER INFORMATION: antisense oligomer

<400> SEQUENCE: 131
caccgcggcg tgctgatcc                                                   19

<210> SEQ ID NO 132
<211> LENGTH: 16
<212> TYPE: DNA
<213> ORGANISM: Artificial Sequence
<220> FEATURE:
<223> OTHER INFORMATION: antisense oligomer

<400> SEQUENCE: 132
ccccaccttc ctccgg                                                      16

<210> SEQ ID NO 133
<211> LENGTH: 18
<212> TYPE: DNA
<213> ORGANISM: Artificial Sequence
<220> FEATURE:
<223> OTHER INFORMATION: antisense oligomer

<400> SEQUENCE: 133
ccgcttgtgc gggccccc                                                    18

<210> SEQ ID NO 134
<211> LENGTH: 18
<212> TYPE: DNA
<213> ORGANISM: Artificial Sequence
<220> FEATURE:
<223> OTHER INFORMATION: antisense oligomer

<400> SEQUENCE: 134
caccgcggcg tgctgatc                                                    18

<210> SEQ ID NO 135
<211> LENGTH: 17
<212> TYPE: DNA
<213> ORGANISM: Artificial Sequence
<220> FEATURE:
<223> OTHER INFORMATION: antisense oligomer

<400> SEQUENCE: 135
caccgcggcg tgctgat                                                     17

<210> SEQ ID NO 136

```
<211> LENGTH: 18
<212> TYPE: DNA
<213> ORGANISM: Artificial Sequence
<220> FEATURE:
<223> OTHER INFORMATION: antisense oligomer

<400> SEQUENCE: 136
accgcggcgt gctgatcc                                                    18

<210> SEQ ID NO 137
<211> LENGTH: 17
<212> TYPE: DNA
<213> ORGANISM: Artificial Sequence
<220> FEATURE:
<223> OTHER INFORMATION: antisense oligomer

<400> SEQUENCE: 137
ccgcggcgtg ctgatcc                                                     17

<210> SEQ ID NO 138
<211> LENGTH: 17
<212> TYPE: DNA
<213> ORGANISM: Artificial Sequence
<220> FEATURE:
<223> OTHER INFORMATION: antisense oligomer

<400> SEQUENCE: 138
accgcggcgt gctgatc                                                     17

<210> SEQ ID NO 139
<211> LENGTH: 20
<212> TYPE: DNA
<213> ORGANISM: Artificial Sequence
<220> FEATURE:
<223> OTHER INFORMATION: antisense oligomer

<400> SEQUENCE: 139
acgttgaggg gcatcgtcgc                                                  20
```